(12) United States Patent
Silbersweig et al.

(10) Patent No.: US 10,586,326 B2
(45) Date of Patent: Mar. 10, 2020

(54) SYSTEMS AND METHODS FOR GENERATING BIOMARKERS BASED ON MULTIVARIATE CLASSIFICATION OF FUNCTIONAL IMAGING AND ASSOCIATED DATA

(71) Applicant: The Brigham and Women's Hospital, Inc., Boston, MA (US)

(72) Inventors: David Silbersweig, Chestnut Hills, MA (US); Emily Stern, Chestnut Hills, MA (US); Hong Pan, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 15/642,522

(22) Filed: Jul. 6, 2017

(65) Prior Publication Data
US 2017/0309022 A1 Oct. 26, 2017

Related U.S. Application Data

(63) Continuation of application No. 14/800,212, filed on Jul. 15, 2015, now Pat. No. 9,773,308.
(Continued)

(51) Int. Cl.
*G06T 7/00* (2017.01)
*G16H 50/20* (2018.01)
(Continued)

(52) U.S. Cl.
CPC .......... *G06T 7/0012* (2013.01); *G06T 11/206* (2013.01); *G06T 11/60* (2013.01);
(Continued)

(58) Field of Classification Search
CPC ..... G06T 7/0012; G06T 11/60; G06T 11/206; G06T 2207/20084; G06T 2207/30016;
(Continued)

(56) References Cited

U.S. PATENT DOCUMENTS

| 9,773,308 B2 | 9/2017 | Silbersweig et al. |
| 2011/0123100 A1 * | 5/2011 | Carroll ................. G06N 5/003 382/155 |

(Continued)

OTHER PUBLICATIONS

Duchesnay, et al., Feature Selection and Classification of Imbalanced Datasets—Application to PET Images of Children with Autistic Spectrum Disorders, NeuroImage, 2011, 57:1003-1014.
(Continued)

*Primary Examiner* — Jon Chang
(74) *Attorney, Agent, or Firm* — Quarles & Brady LLP

(57) ABSTRACT

Systems and methods for generating biomarkers associated with neuropsychiatric disorders, neurodevelopmental disorders, neurobehavioral disorders, or other neurological disorders are described. In general, the biomarkers are generated based on correlations between functional imaging data and clinical acquired from a subject, as computed using a multivariate classifier. Functional imaging data may include functional magnetic resonance images, or activation maps generated from such images. Clinical data generally includes data associated with a clinical or behavioral characterization of the subject. The biomarkers can be used to monitor or otherwise assess a treatment response; to provide diagnostic information, such as subtyping or classifying a disorder; to provide prognostic information, such as a prediction of treatment response or outcome; or to indicate functional or anatomical targets for treatments.

20 Claims, 34 Drawing Sheets
(28 of 34 Drawing Sheet(s) Filed in Color)

Related U.S. Application Data

(60) Provisional application No. 62/024,540, filed on Jul. 15, 2014.

(51) Int. Cl.
  *G06K 9/62* (2006.01)
  *G06T 11/60* (2006.01)
  *G06T 11/20* (2006.01)
  *G16H 50/50* (2018.01)

(52) U.S. Cl.
  CPC ............. *G16H 50/20* (2018.01); *G16H 50/50* (2018.01); *G06K 9/6293* (2013.01); *G06K 2209/05* (2013.01); *G06T 2207/20084* (2013.01); *G06T 2207/30016* (2013.01)

(58) Field of Classification Search
  CPC ......... G06K 2209/05; G06K 2209/051; G06K 9/6267; G06K 9/6293; G06F 19/3437; G06F 19/345; G06F 19/00; G16H 50/20; G16H 50/50
  See application file for complete search history.

(56) References Cited

U.S. PATENT DOCUMENTS

| | | |
|---|---|---|
| 2015/0018664 A1 | 1/2015 | Pereira et al. |
| 2016/0025828 A1 | 1/2016 | Jiang et al. |
| 2017/0123028 A1* | 5/2017 | Hammer .............. A61B 5/0042 |

OTHER PUBLICATIONS

Hinrichs, et al., Predictive Markers for AD in a Multi-Modality Framework: An Analysis of MCI Progression in the ADNI Population, NeuroImage, 2011, 55:574-589.

Kim, et al., Integration of Structural and Functional MRI Features Improves Mild Cognitive Impairment (MCI) Detection, IEEE International Workshop on Pattern Recognition in NeuroImaging, 2011, pp. 5-8.

Zhang, et al. Multimodal Classification of Alzheimer's Disease and Mild Cognitive Impairment, NeuroImage, 2011, 55:856-867.

Wikipedia, Definition of Mahalanobis Distance, 2014, 4 pages.

PCT International Search Report and Written Opinion, PCT/US2015/040539, dated Oct. 6, 2015.

\* cited by examiner

| Study/Measures | | Depression | Bipolar | BPD | Panic | PTSD_GAD | PMDD | Schizo | WTC | Epilepsy/Depression |
|---|---|---|---|---|---|---|---|---|---|---|
| | fMRI (Total: 442 Unique Individuals/556 Scanning Sessions) | N=22; 12P/10H | N=16; 13P/10H | N=47; 26P/7TM/14H | N=13 | N=134; 69PTSD/3GAD/12TC/37H | N=57; 35P/22H | N=61; 42P/22H | N=52; 27Dir/20Indir/5InBtwn | N=30; 18P/12H |
| Functional Imaging Data | Neutral Words | Y | Y | Y | Y | Y | Y | Y | | Y |
| | Negative Words | Y | Y | Y | Y | Y | Y | Y | | Y |
| | Positive Words | Y | Y | Y | Y | Y | Y | Y | | Y |
| | Neutral Pictures | | | | | | | | Y | |
| | Negative Pictures | | | | | | | | Y | |
| | Positive Pictures | | | | | | | | Y | |
| | Affective Face Paradigm | | | | Y | Y | | | | Y |
| | Fear Conditioning | | | Y | | | Y | Y | | |
| | Inhibitory Control | | | Y | | | Y | | | |
| | Resting BOLD | | Y | Y | Y | Y | Y | Y | Y | Y |
| | Structural MRI | Y | Y | Y | Y | Y | Y | Y | Y | Y |
| Behavioral Data | In-Scanner Behavior | Y | Y | Y | Y | Y | Y | Y | Y | Y |
| | Post-Scan Behavior | Y | Y | Y | Y | Y | Y | Y | Y | Y |
| Physiological Data | Cardiac | Y | Y | Y | Y | Y | Y | Y | Y | |
| | Respiratory | Y | Y | Y | Y | Y | Y | Y | Y | |
| | Galvanic Skin Response | | | | Y | Y | | | | |
| | Cortisol Measures | | | | Y | Y | | | | |
| Clinical Data | Beck Depression Inventory (BDI) | Y | | | Y | Y | Y | | Y | Y |
| | COPE | | | | Y | Y | | | Y | |
| | Hamilton-D | Y | | | Y | Y | | | | |
| | STAI | Y | | | Y | Y | | | Y | Y |
| | State Trait Anger Expression Inventory (STAXI) | | | Y | | Y | | | Y | |

P: Patients
H: Healthy Controls
TM: Tempermentally-Matched Controls
PTSD: Post-Traumatic Stress Disorder
GAD: Generalized Anxiety Disorder
BPD: Borderline Personality Disorder
TC: Trauma Controls
PMDD: Premenstrual Dysphoric Disorder
Schizo: Schizophrenia
WTC: World Trade Center (Dir=Directly Exposed; Indir=Indirectly Exposed; InBtwn=Intermediate Exposure)
Epilepsy/Depression: Epilepsy and Depression

FIG. 1B

| | Study/Measures | Depression | Panic | PTSD, GAD | Epilepsy/Depression |
|---|---|---|---|---|---|
| | fMRI (Total 186 Unique Individuals/Scanning Sessions) | N=22; 12P/10H | N=13 | N=134; 69PTSD/3GAD/12TC/37H | N=30; 18P/12H |
| Functional Imaging Data | Neutral Words | Y | Y | Y | Y |
| | Negative Words | Y | Y | Y | Y |
| | Positive Words | Y | Y | Y | Y |
| | Structural MRI | Y | Y | Y | Y |
| Behavioral Data | In-Scanner Behavior | Y | Y | Y | Y |
| | Post-Scan Behavior | Y | Y | Y | Y |
| Physiological Data | Cardiac | Y | Y | Y | Y |
| | Respiratory | Y | Y | Y | Y |
| Clinical Data | Beck Depression Inventory (BDI) | Y | Y | Y | Y |
| | STAI | Y | Y | Y | Y |

P: Patients
H: Healthy Controls
TM: Tempermentally-Matched Controls
PTSD: Post-Traumatic Stress Disorder
GAD: Generalized Anxiety Disorder
BPD: Borderline Personality Disorder
TC: Trauma Controls
Epilepsy/Depression: Epilepsy and Depression

FIG. 1C

○ "DISORDER" GROUP
● "HEALTHY" GROUP

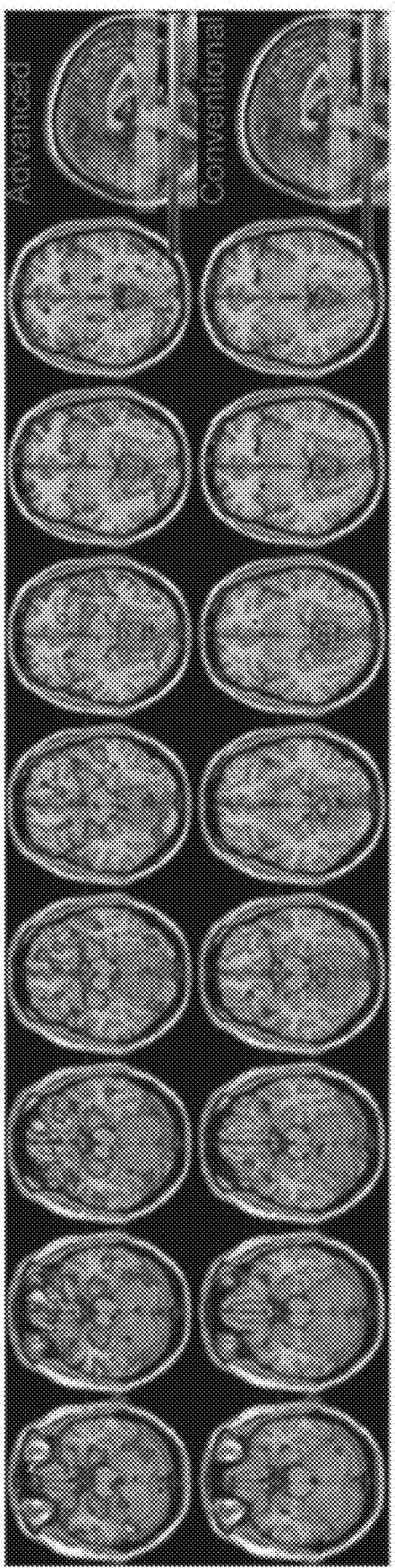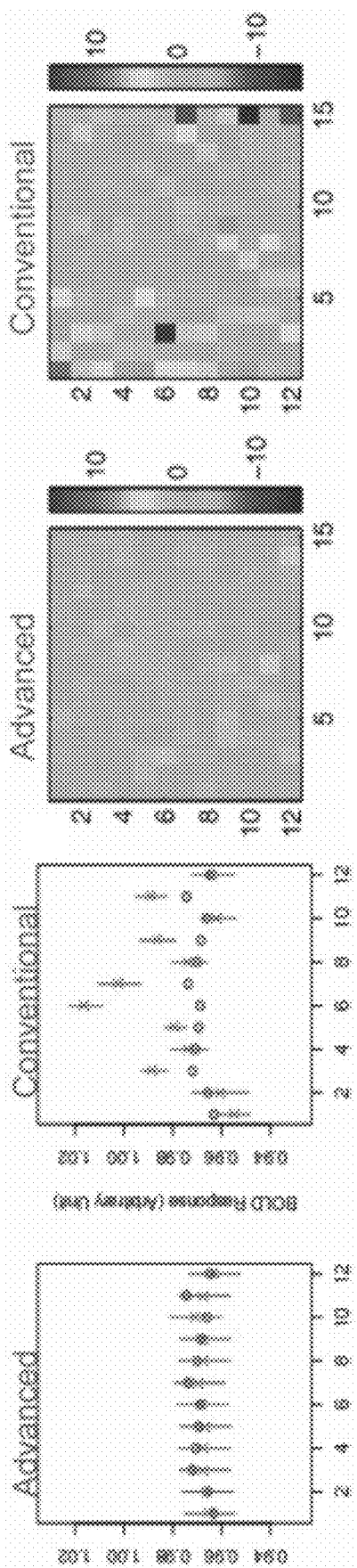
FIG. 9A
FIG. 9B
FIG. 9C

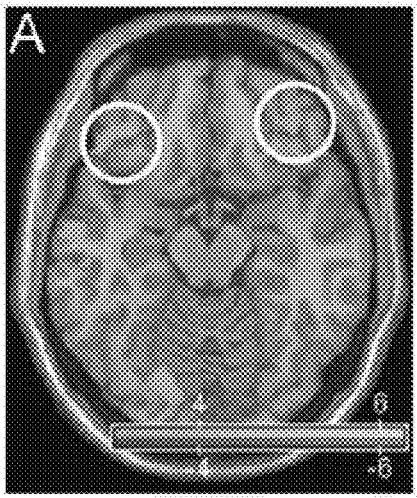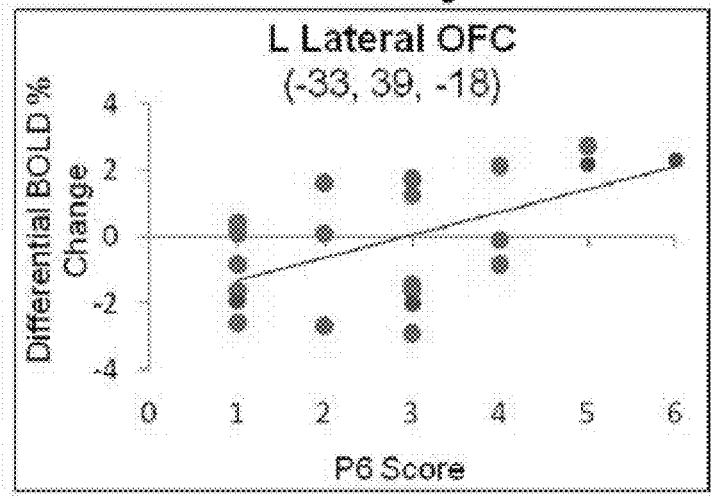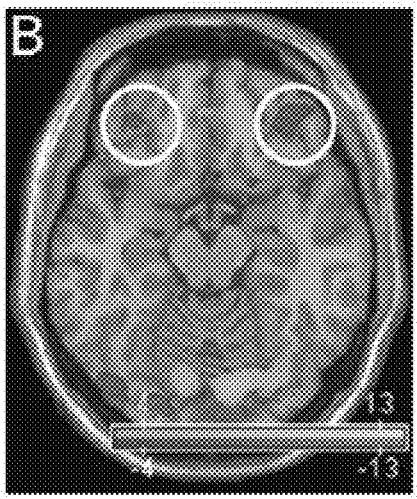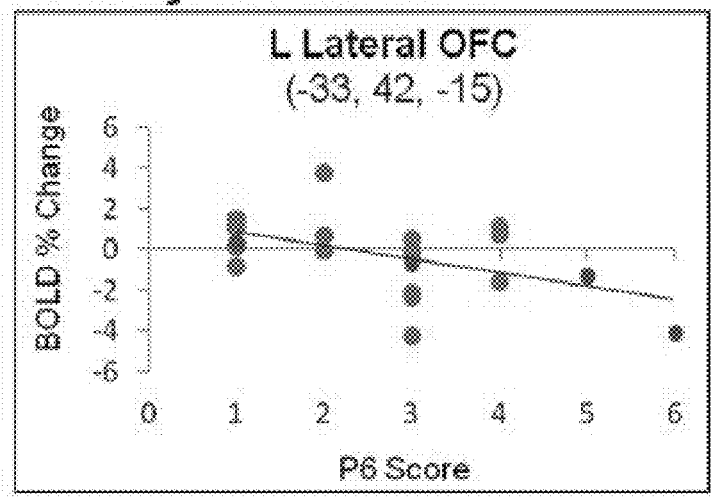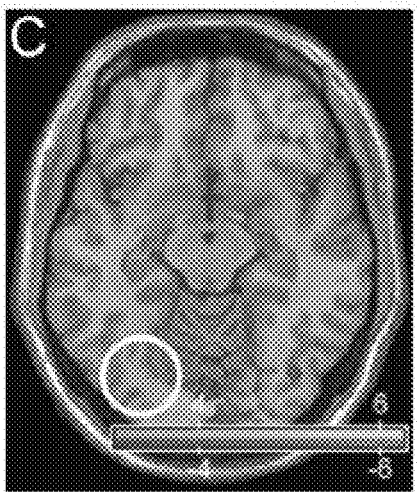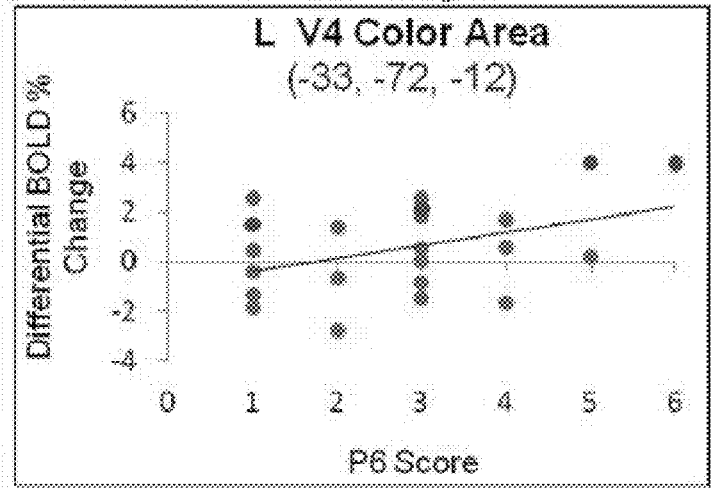
FIGS. 13A–13C

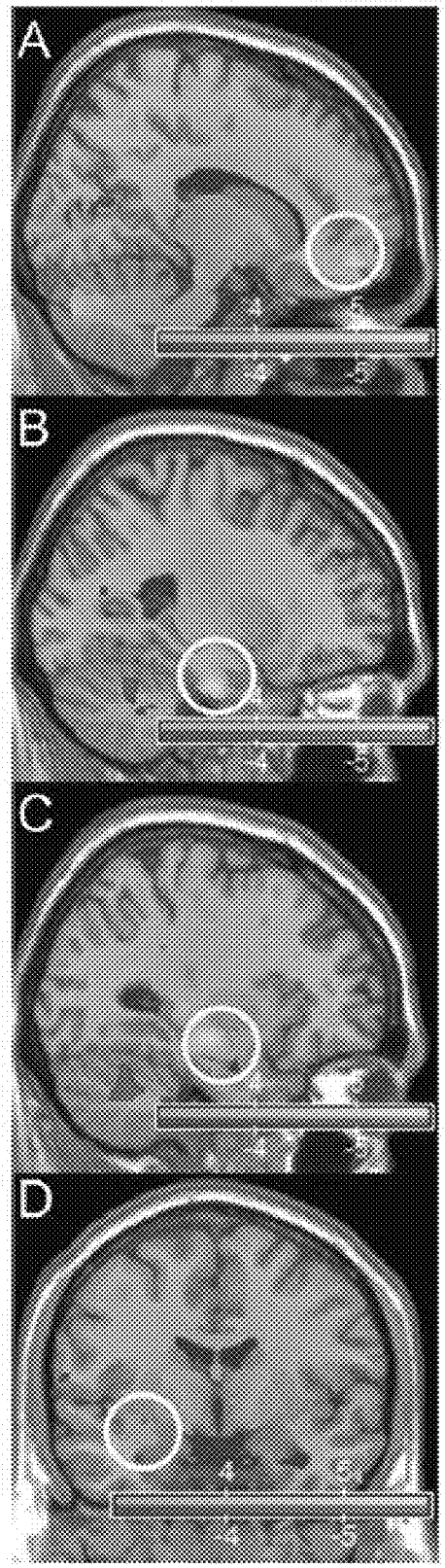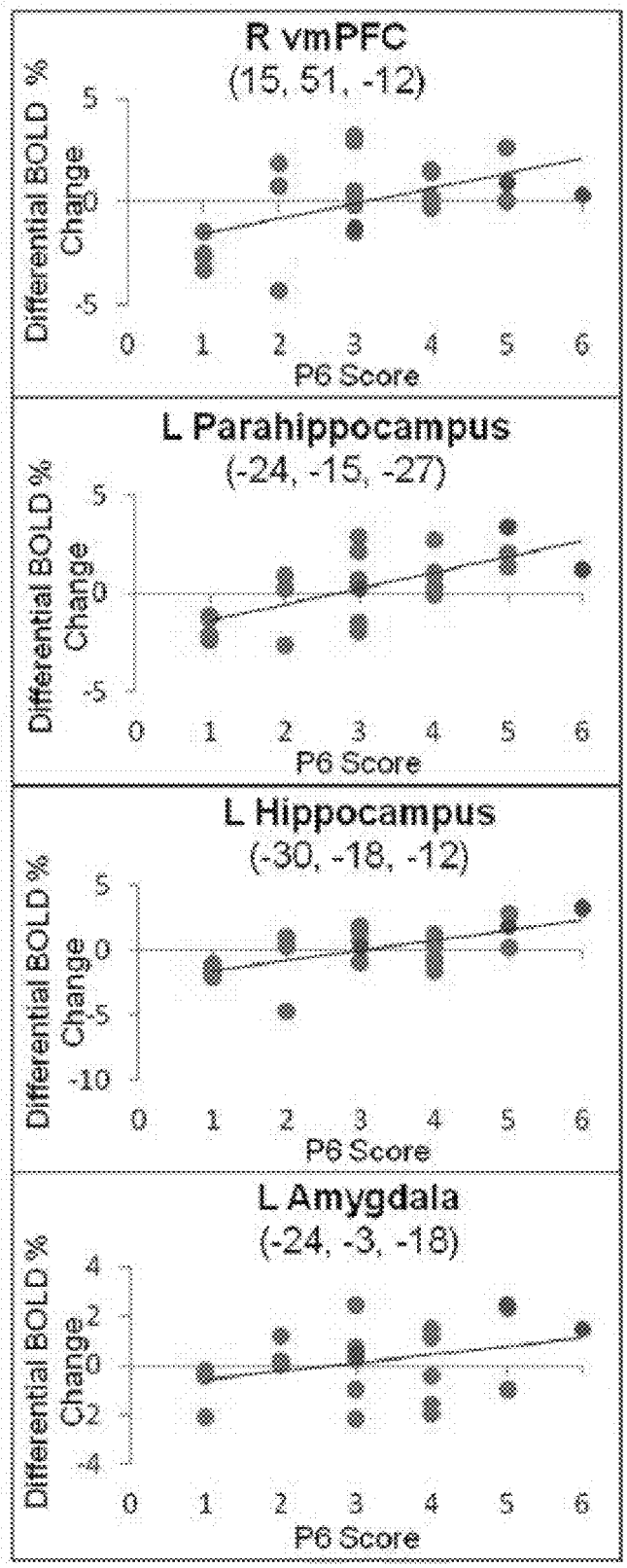
FIGS. 16A–16D

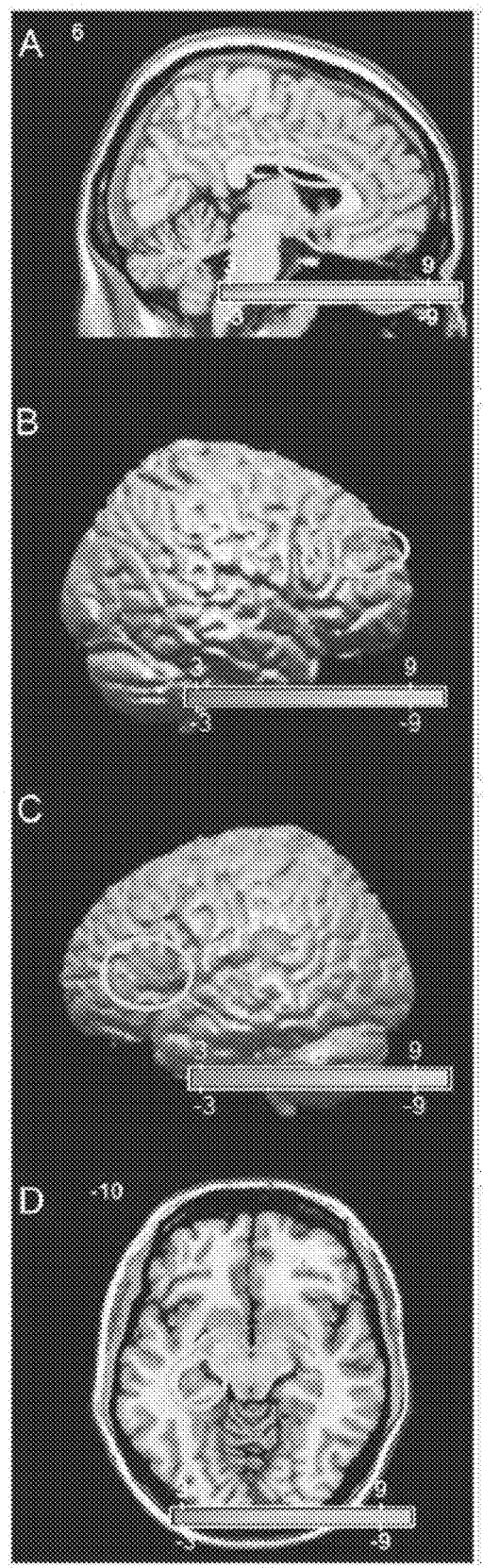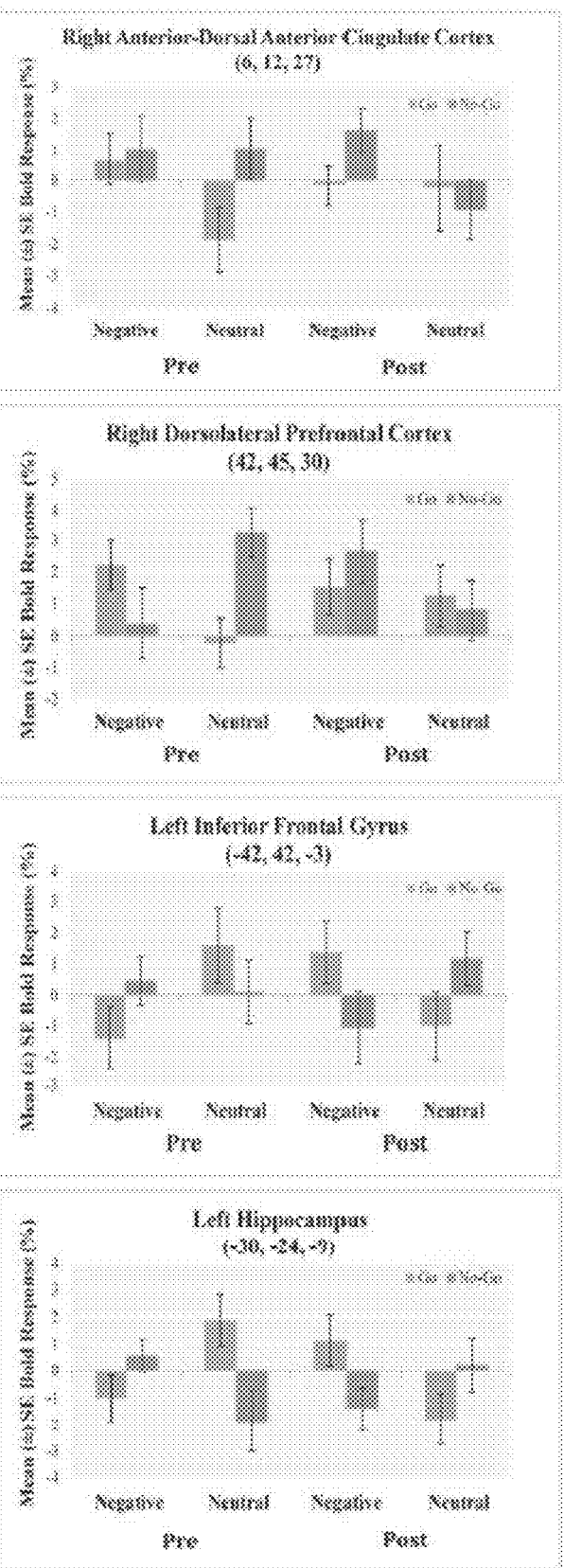
FIG. 20A–20D

SYSTEMS AND METHODS FOR GENERATING BIOMARKERS BASED ON MULTIVARIATE CLASSIFICATION OF FUNCTIONAL IMAGING AND ASSOCIATED DATA

CROSS-REFERENCE TO RELATED APPLICATIONS

This application is a continuation of U.S. patent application Ser. No. 14/800,212 filed Jul. 15, 2015, which claims the benefit of U.S. Provisional Patent Application 62/024,540, filed Jul. 15, 2014, all of which is incorporated herein by reference.

BACKGROUND OF THE INVENTION

The field of the invention is systems and methods for generating biomarkers from functional imaging data and associated clinical data. More particularly, the invention relates to systems and methods for generating biomarkers associated with neuropsychiatric, neurodevelopmental, neurobehavioral, or other neurological disorders.

Magnetic resonance imaging ("MRI") and other non-invasive techniques such as functional magnetic resonance imaging ("fMRI"), electroencephalogram ("EEG"), magnetoencephalography ("MEG"), positron emission tomography ("PET"), infrared ("IR") imaging, single photon emission computed tomography ("SPECT"), and computed tomography ("CT") have been proposed to directly examine a combination of brain regions that have been implicated in various brain functions, including dysfunction pertaining to psychiatric conditions and illnesses.

The relationship of these techniques is such that many of these technologies can be combined to assess multiple levels of function. To investigate brain function at multiple scales, however, distinct methodologies to perform measurements, archive them, and process and analyze them to provide distinct and useful correlations, are necessary.

SUMMARY OF THE INVENTION

The present invention overcomes the aforementioned drawbacks by providing a computer-implemented method for generating a biomarker associated with a neuropsychiatric, neurodevelopmental, neurobehavioral, or other neurological disorder. Functional imaging data acquired from a subject's brain and clinical data associated with the subject are provided to a computer system. The computer system then generates a biomarker associated with the neuropsychiatric, neurodevelopmental, neurobehavioral, or other neurological disorder by computing a correlation between the functional imaging data and the clinical data using a multivariate classifier. In some instances, additional data associated with system-level biological measures of the subject can also be provided to the computer system and used for generating the biomarker. As one example, this additional data can include other imaging data, physiological data, genetic data, or epigenetic data.

In some embodiments, a matrix having rows that correspond to regions in the subject's brain and having columns that correspond to the functional imaging data and the clinical data is formed, and the correlation between the functional imaging data and the clinical data is computed based on inputting the matrix to the multivariate classifier. In some instances, dimensionality reduction or feature extraction can be performed on the matrix before inputting the matrix to the multivariate classifier.

In some embodiments, the biomarker generated by the computer system includes covariance patterns based on the correlation between the functional imaging data and the clinical data computed by the computer system using the multivariate classifier.

In some other embodiments, the biomarker generated by the computer system includes co-varying traits based on the correlation between the functional imaging data and the clinical data computed by the computer system using the multivariate classifier.

In still other embodiments, the biomarker generated by the computer system includes an interregional correlation matrix based on output of the multivariate classifier, or includes an association matrix based on output of the multivariate classifier.

In some embodiments, the multivariate classifier is based on a principal component analysis and the biomarker includes a group level spatial component image output from the principal component analysis. In some instances, the biomarker may also include a loading score computed by the computer system from the group level spatial component images.

In some other embodiments, the multivariate classifier is based on a thresholding correlation analysis, and the biomarker includes a group level interregional correlation map output from the thresholding correlation analysis.

In some other embodiments, the multivariate classifier is based on a hierarchical clustering analysis, and the biomarker includes a cluster map that depicts clusters or networks of brain regions with similar activation levels across subsets of valenced conditions. In some instances, the biomarker may also include linearly separable co-varying patterns identified with the computer system in the cluster map.

In some other embodiments, the multivariate classifier is based on a machine learning algorithm, and the biomarker includes a report that indicates clusters of brain regions defined by brain-wide activity and connectivity levels across valenced conditions. In some instances, the machine learning algorithm can be trained on a database that includes at least one of functional imaging data, other imaging data, physiological data, clinical data, genetic data, and epigenetic data associated with the neuropsychiatric, neurodevelopmental, neurobehavioral, or other neurological disorder.

In some other embodiments, the multivariate classifier is based on an algorithm that estimates graph theory-based network organizational measures, and the biomarker indicates topological features in functional connectivity patterns across dimensional domains.

In some embodiments, the functional imaging data can include functional magnetic resonance images acquired from the subject while the subject was performing a functional task, or functional magnetic resonance images acquired from the subject while the subject was in a resting state. The functional imaging data can include activation maps that depict neuronal activation patterns associated with the functional task or the resting state, or such activation maps can be generated from the respective functional magnetic resonance images.

In some other embodiments, activation maps can be generated using a multi-level mixed-effects statistical model. In some instances, the multi-level mixed-effects statistical model can include a nested random-effects structure. In some other instances, the multi-level mixed-effects statistical model can include an intra-subject power variance function and an autoregressive correlation structure.

It is another aspect of the invention to provide a computer-implemented method for generating a biomarker that indicates a target for treating a neuropsychiatric, neurodevelopmental, neurobehavioral, or other neurological disorder. Functional imaging data acquired from a subject's brain, clinical data associated with the subject, and additional data associated with system-level biological measures of the subject are all provided to a computer system. The computer system then generates a biomarker that indicates a target for treating a neuropsychiatric, neurodevelopmental, neurobehavioral, or other neurological disorder by computing a correlation between the functional imaging data, the clinical data, and the additional data using a multivariate classifier.

In some embodiments, the biomarker is generated by mapping the correlation to a multidimensional parametric space, in which data points mapped to a similar region of the multidimensional parametric space correspond to similar neural signatures and symptoms associated with the neuropsychiatric, neurodevelopmental, neurobehavioral, or other neurological disorder. The multidimensional parametric space may include dimensions corresponding to the functional imaging data, the clinical data, and the additional data.

In some other embodiments, the biomarker indicates a functional target for treatment, in which the functional target represents symptoms correlated with the neuropsychiatric, neurodevelopmental, neurobehavioral, or other neurological disorder. The functional target may also further represent patterns of neuronal activation correlated with the symptoms and the neuropsychiatric, neurodevelopmental, neurobehavioral, or other neurological disorder.

In some other embodiments, the biomarker indicates an anatomical target for treatment, in which the anatomical target represents brain regions associated with symptoms correlated with the neuropsychiatric, neurodevelopmental, neurobehavioral, or other neurological disorder.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1B and 1C represent examples of data that can be stored in a database that can be interrogated in accordance with some embodiments of the present invention;

FIG. 9A illustrates a comparison of advanced (top row) versus conventional (bottom row) data analysis methods from an fMRI study investigating the systems-level neuropathophysiology of premenstrual dysphoric disorder ("PMDD");

FIG. 9B illustrates coverage probabilities, based on 95% confidence intervals, for the observed values using the advanced and conventional statistical analysis methods;

FIG. 9C illustrates a mean estimation bias measured via a cross-validation z-score;

FIGS. 13A-13C illustrate lateral orbitofrontal cortex and V4 color area activations correlated to persecutory delusion severity in the instructed-fear/safety paradigm;

FIGS. 16A-16D illustrate frontolimbic activations correlated to persecutory delusion severity in the threat word versus neutral word contrast;

FIGS. 20A-20D illustrate a three-way interaction between negative (versus neutral) emotional words and no-go (versus Go) conditions [(post-treatment scan vs. pre-treatment scan)×(negative vs. neutral)×(no-go vs. go)];

DETAILED DESCRIPTION OF THE INVENTION

Figure 1A:
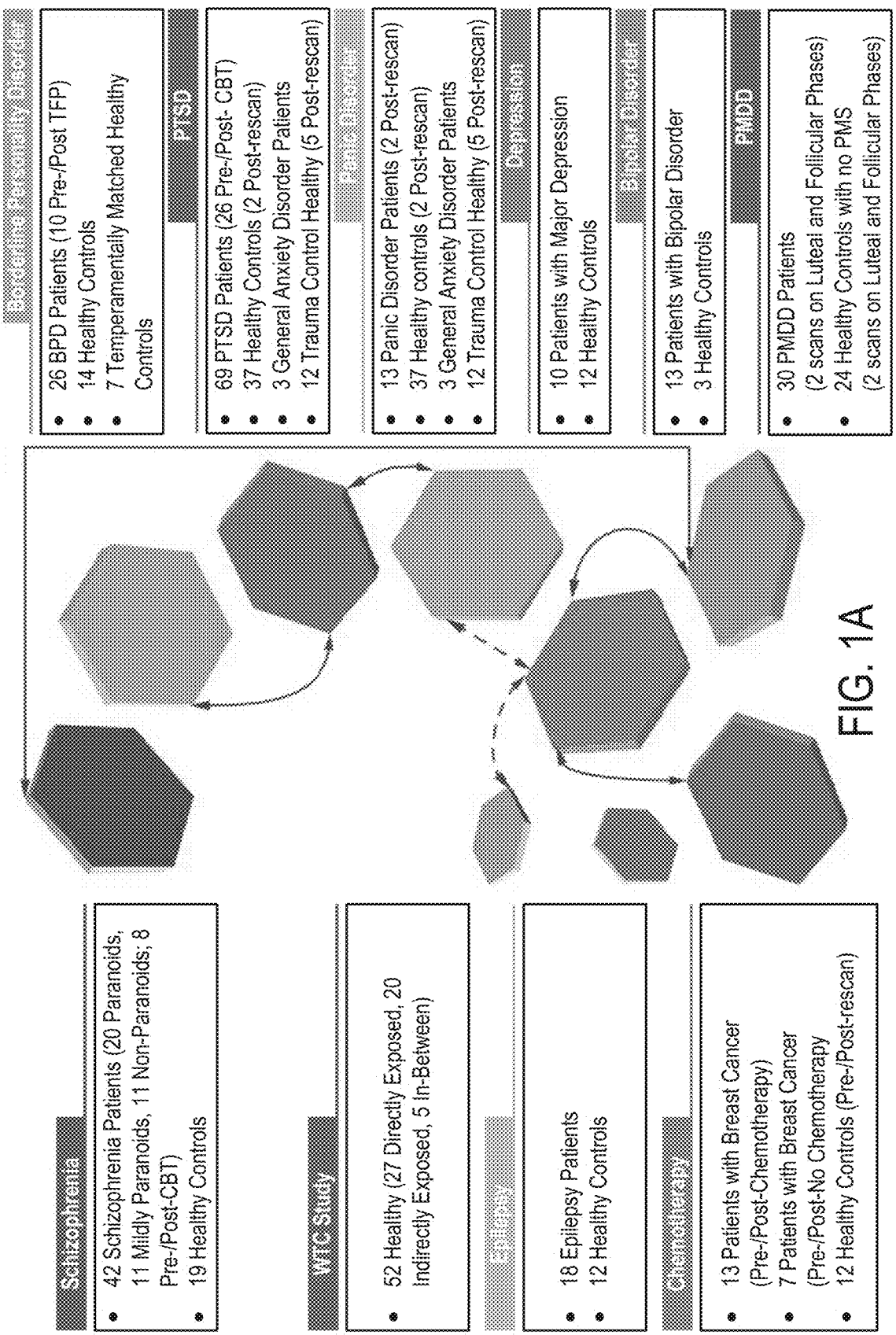
FIG. 1A illustrates a summary of an example database of functional imaging data that has been acquired for multiple patient populations, and illustrates a potential schema of how the disorders noted in the database may relate to one another, given symptomatology and comorbidities.

Described here are systems and methods for generating biomarkers associated with neuropsychiatric disorders, neurodevelopmental disorders, neurobehavioral disorders, or other neurological disorders. In some embodiments, the biomarkers are generated based on functional imaging data and clinical data acquired from a subject. Functional imaging data may include functional magnetic resonance images, or activation maps generated from such images. In some other embodiments, the biomarkers are generated based also on additional data associated with the subject. Examples of additional data include other imaging data, physiological data, genetic data, and epigenetic data.

Examples of neuropsychiatric, neurodevelopmental, neurobehavioral, or other neurological disorders for which biomarkers can be generated include, but are not limited to, the following disorders: schizophrenia, including psychosis; anxiety disorders, including panic disorder, post-traumatic stress disorder, and anxiety in the wake of the World Trade Center disaster; mood and other affective disorders, including major depression, geriatric depression, and bipolar disorder; mood disorders in epilepsy; personality disorders, such as borderline personality disorder; cognitive changes associated with chemotherapy; sex differences in brain function in health and disease (e.g., premenstrual dysphoric disorder); and traumatic brain injury. The biomarkers can also be generated in association with normal cognitive and emotional function.

In general, "biomarker" can refer to a measurable indicator of a neurological state or condition, whether of a normal or healthy neurological state or condition, or of a state or condition related to a neuropsychiatric disorder, a neurodevelopmental disorder, a neurobehavioral disorder, or other neurological disorder, or with symptoms associated with such disorders. The biomarkers described here are generally based on functional imaging data and clinical data, but can also be based on other imaging data, physiological data, genetic data, and epigenetic data.

In some instances, a biomarker can include a digital image that can provide a measurable indicator of a neurological state or condition. As one example, a biomarker may include a digital image that depicts covariance patterns based on correlations between functional imaging data and clinical data, whether for a group or an individual. As another example, the biomarker may include a digital image that depicts co-varying traits based on a correlation between functional imaging data and clinical data, whether for a group or an individual. As another example, a biomarker may include a representation of correlated data in a multi-dimensional (e.g., two-dimensional or greater) parametric space. Such representations can include classifier maps, which depict correlated data as points in the multi-dimensional space.

In some other instances, a biomarker can include qualitative or quantitative characteristics, indices, or metrics. As one example, a biomarker can include a center-of-mass calculated for a group of correlated data classified as belonging to a particular group in a multidimensional space. As another example, a biomarker can include a distance metric calculated for correlated data for an individual, measured relative to a center-of-mass or other point in a classifier map.

In general, "functional imaging data" can refer to images or data acquired using functional magnetic resonance imaging ("fMRI") techniques, such as fMRI techniques that acquire images that depict a blood-oxygen level dependent ("BOLD") contrast. Preferably, functional imaging data is acquired by imaging the subject's brain, but in some examples may include imaging other portions of the subject's central nervous system, such as the spinal cord.

Functional magnetic resonance images and data can be acquired during a resting state (i.e., resting state data) or during the performance of one or more functional tasks (i.e., activation-based data). The functional imaging data can also include functional maps of brain activity that are generated from functional magnetic resonance images or data. These "activation maps" can include activation-based maps, in which the neuronal activation is associated with neuronal activity induced in response to the performance of a functional task. The neuronal activation maps can also include resting-state maps, in which the neuronal activation is associated with neuronal activity occurring when the subject is resting or otherwise not performing a particular functional task.

"Other imaging data" can include structural or anatomical images or data acquired with magnetic resonance imaging ("MRI") and other medical imaging modalities. Other imaging data can also include quantitative images or parametric maps that are produced based on images or data acquired with MRI or other medical imaging modalities.

In some instances, other imaging data can include images and parametric maps based on diffusion-weighted imaging of the subject's brain or spinal cord. For example, the other imaging data can include images or parametric maps generated using diffusion tensor imaging ("DTI") or the like. This other imaging data can therefore also include tractographic maps generated based on diffusion-weighted imaging of the subject's brain or spinal cord.

In some instances, other imaging data can also refer to images and data acquired using nuclear medicine, such as via positron emission tomography ("PET") or single photon emission computed tomography ("SPECT"). Images or data acquired with PET or SPECT can include images or data acquired from a subject who has been administered a radiotracer. Radiotracers generally include chemical compounds labeled with a radioisotope. Examples of radioisotopes that can be used include fluorine-18, oxygen-15, and carbon-11, which can be used to label agents to measure metabolism, blood flow, and blood volume, respectively.

In some other instances, the other imaging data can include imaging data that provides information about a subject's neurochemistry. As one example, this type of other imaging data can include images or data acquired using magnetic resonance spectroscopy, which can provide information about metabolite and other neurochemical concentrations in the brain. As another example, information about a subject's neurochemistry can be provided via PET or SPECT, using an appropriate radiotracer.

"Physiological data" generally includes data obtained by measuring one or more aspects of a subject's physiology. Examples of physiological data can include measurements of a subject's blood chemistry, including measurements of cortisol or other hormones; measurements of a subject's skin conductance response; respiratory data; and electrophysiological data, which can include electrocardiography ("ECG"), electroencephalography ("EEG"), magnetoencephalography ("MEG"), and electromyography ("EMG") measurements.

In some embodiments, physiological data can include data acquired using personal fitness trackers or other mobile devices (e.g., smart phones) that incorporate one or more sensors including heart rate sensors, pedometers, accelerometers, temperature sensors, and so on.

"Clinical data" generally includes data about the subject that is obtained from a clinician, including data associated with a clinical assessment, a clinical characterization, or both. In some instances, clinical data can include clinical ratings and clinical scores. As one example, a clinical score can include a score based on a Positive and Negative Syndrome Scale ("PANSS") score, which is a medical scale used for measuring symptom severity of patients with schizophrenia. In some other instances, clinical data can include behavioral data that generally indicates a behavior of the subject. As one example, behavioral data can include eye tracking. As another example, behavioral data can include monitoring the subject's behavior during the performance of a functional task during functional magnetic resonance imaging ("fMRI").

"Genetic data" generally includes data associated with genetic influences on a subject's gene expression. As an example, genetic data can include allelic variants or single nucleotide polymorphisms to identify imaging endophenotypes associated with clinical features. Such data can serve as predictors of differential treatment response.

"Epigenetic data" generally includes data associated with non-genetic influences on a subject's gene expression. As an example, epigenetic data can include fluid biomarkers, such as those obtained with metabolomics, proteomics, lipidomics, and immunomics.

In general, the biomarkers generated by the systems and methods described here can indicate or otherwise define neural signatures associated with particular neuropsychiatric disorders, neurodevelopmental disorders, neurobehavioral disorders, or other neurological disorders. Thus, it is one aspect of the invention to provide systems and methods that utilize functional brain imaging across a range of neuropsychiatric, neurodevelopmental, neurobehavioral, or other neurological disorders for biomarker development. The biomarkers identified can include functional MRI ("fMRI") profiles and activation maps that correlate with specific psychiatric disease states, inmood, psychotic, personality, anxiety, and other neuropsychiatric, neurodevelopmental, neurobehavioral, or other neurological disorders.

In some embodiments, the generation of these biomarkers includes detailed clinical phenotyping, resulting in granular assessment of symptom states, which are incorporated with the functional imaging data. These biomarkers can generally provide a foundation for the development of non-invasive diagnostics and targeted therapeutics in neuropsychiatric, neurodevelopmental, neurobehavioral, and other neurological disorders. In some instance, the biomarkers can provide risk and resilience profiling that can guide early intervention and prevention; mechanistic illness subtyping that can guide individualized therapeutic selection, such as pharmacologic, brain stimulation, or psychotherapeutic therapies; the evaluation of new interventions; and the prediction of clinical response and outcome. Embodiments thus have utility in diagnostic and prognostic applications, identification of druggable targets to aid in therapeutic development or drug repurposing, and identification of biomarkers to evaluate existing therapeutics and to predict treatment response.

In some aspects, the biomarkers can provide diagnostic information for mechanism-based diagnostics. These biomarkers can be used for identifying and tracking pathophysiological mechanisms, pathways of disease, and pathways of symptom expression. These biomarkers can also be used to provide biologically-based disease classification and subtyping. Using biomarkers generated in this manner, early disease detection can be achieved, and trajectory-altering interventions can be determined and assessed.

In some other aspects, the biomarkers can provide information useful for targeted therapeutics. These biomarkers can be used to identify targets for treatment, and for predicting and tracking treatment response. Advantageously, these biomarkers can be generated across a wide spectrum of neuropsychiatric, neurodevelopmental, and neurobehavioral symptoms.

Aspects of the invention thus include developing and applying new and existing methods of imaging for the detection, localization, and characterization of final common pathways of major neuropsychiatric, neurodevelopmental, neurobehavioral, or other neurological disorder expression, as a foundation for clinical advances.

As one example, fronto-limbic-subcortical circuits that are involved in fear/stress, control, volition, and reward systems, can be probed across a range of psychiatric disorders. These neural circuits correspond closely to circuitry described in the Negative Valence Systems Domain of the NIMH Research Domain Criteria ("RDoC") project. Similar symptomatology and neural circuitry can be assessed using the same, or similar, neuropsychological imaging probes across major psychiatric DSM ("Diagnostic and Statistical Manual of Mental Disorders") diagnoses, thereby identifying neurobiological substrates that can provide a framework for more effective diagnosis and treatment.

FIG. 1A summarizes an example database of functional imaging data that has been acquired for multiple patient populations. FIG. 1A also illustrates a potential schema of how the disorders noted in FIG. 1A may relate to one another, given symptomatology and comorbidities. Preferably, the functional imaging data is acquired using types and combinations of advanced neuroimaging probes and analytics, utilized within and across the spectrum of neuropsychiatric, neurodevelopmental, neurobehavioral, and other neurological disorders. As one example, the neuroimaging probes can include functional tasks and protocols that assess a collection of emotional and behavioral states, as well as resting state activity.

The functional imaging data described in FIG. 1A can be stored in a database that also contains a collection of clinically-linked imaging data and knowledge matrices that can be interrogated. As an example, the database can also include associated imaging data, physiological data, clinical data, genetic data, or epigenetic data. A collection of analytical methods can be used to interrogate this database, enabling the user to obtain the desired biomarker output. Examples of data that can be stored in such databases are represented in FIGS. 1B and 1C.

Thus, in some embodiments, systems that can be used for generating biomarkers in accordance with various aspects of the invention can include a comprehensive collection of methodological approaches that provide a finely tuned fMRI data acquisition environment optimized for neuropsychiatric, neurodevelopmental, neurobehavioral, or other neurological disorders. This comprehensive collection of methodological approaches is both clinically feasible and researcher-friendly, and also enables effective translational research projects and clinical trials in a timely fashion.

The collection of methodological approaches can include hardware and software components, such as fMRI acquisition protocols and specialized pulse sequences, an optimized fMRI instrumentation environment, utilization of specific neuropsychological probes during imaging, and processing and analytical methods used to identify pertinent functional brain maps and associated informatics in patient populations.

Figure 2:
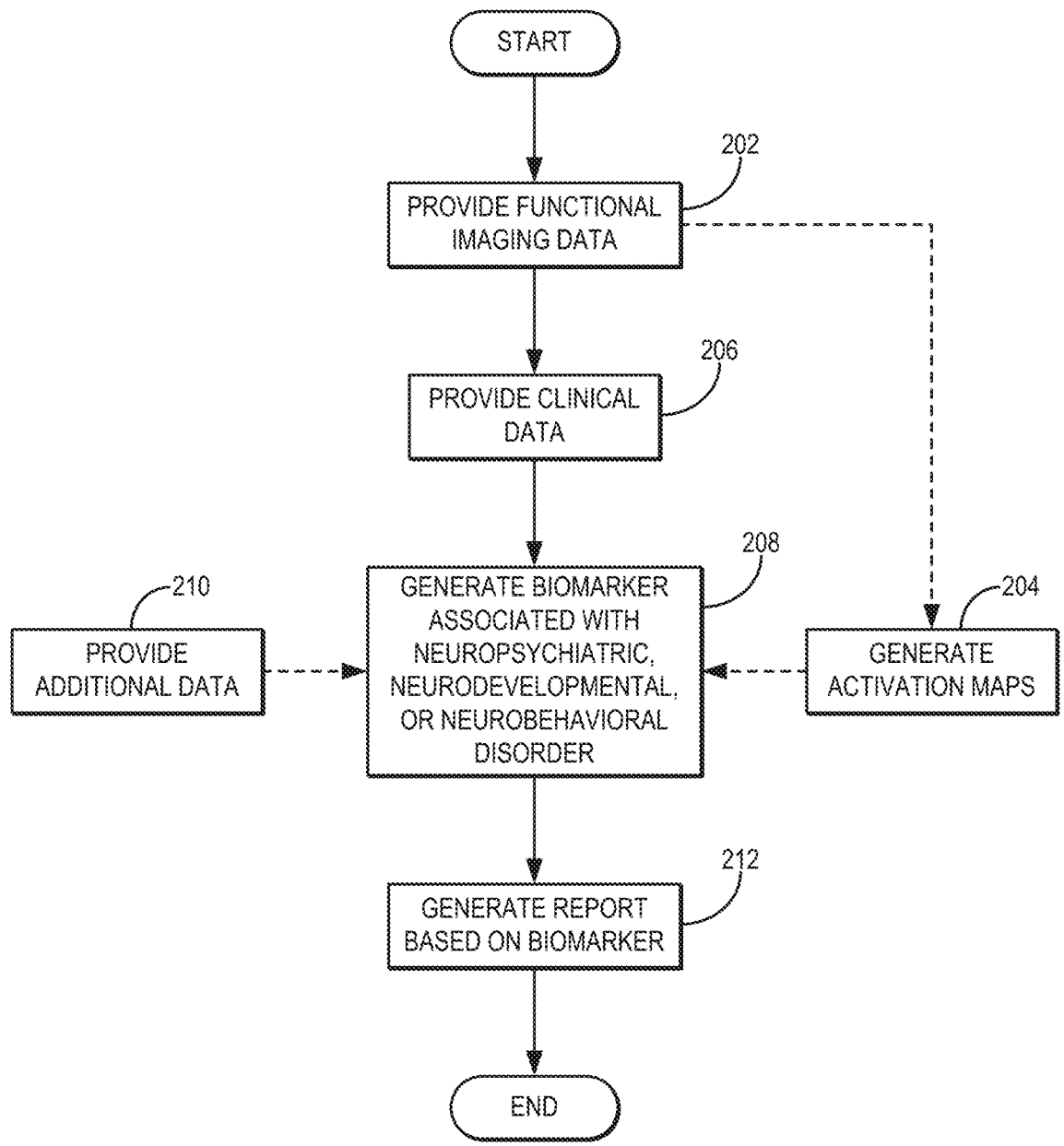
FIG. 2 is a flowchart setting forth the steps of an example method for generating a biomarker associated with a particular neuropsychiatric, neurodevelopmental, neurobehavioral, or other neurological disorder based on functional imaging data acquired from a subject's brain and based on associated clinical data acquired from the subject.

Referring now to FIG. 2, a flowchart is illustrated as setting forth the steps of an example method for generating a biomarker based on clinical data and functional imaging data obtained from a subject, where the biomarker is associated with a particular neuropsychiatric, neurodevelopmental, neurobehavioral, or other neurological disorder.

As one example, the biomarker can indicate a subject's response to a particular treatment. Such a biomarker is advantageous because it provides insight into changes in both the neural signatures of the subject and the behavioral and clinical characterizations of the subject. For instance, it would be advantageous to know that a particular treatment alters a subject's neural signatures without beneficially altering their behavioral and clinical characterizations. Likewise, it would be advantageous to know how a subject's neural signatures are altered when a particular treatment is effective at treating a subject's behavioral and clinical characterizations. Such information could be useful for understanding the mechanisms underlying treatment, which can supplement the design of new treatment regimens, or the adjustment of a treatment administered to a subject.

As another example, the biomarker can provide diagnostic information pertaining to the neuropsychiatric, neurodevelopmental, neurobehavioral, or other neurological disorder. In some embodiments, the biomarker can be used to subtype a particular neuropsychiatric, neurodevelopmental, neurobehavioral, or other neurological disorder. In some other embodiments, the biomarker can be used to classify a particular neuropsychiatric, neurodevelopmental, neurobehavioral, or other neurological disorder.

As another example, the biomarker can provide prognostic information pertaining to the neuropsychiatric, neurodevelopmental, neurobehavioral, or other neurological disorder. In some embodiments, the biomarker can be used to predict the response of a subject to a particular treatment regimen. For instance, the biomarker can provide useful information about the likelihood of effective treatment using a particular treatment regimen to treat a particular neuropsychiatric, neurodevelopmental, neurobehavioral, or other neurological disorder, or symptoms associated with such disorders, based on the neural signatures and behavioral and clinical characterization of the subject. In some instances, the biomarker can provide a probability on whether relapse is likely to occur following a particular treatment regimen.

Referring still to FIG. 2, the method includes providing functional imaging data, as indicated at step 202. As one example, the functional imaging data can be provided by retrieving the functional imaging data from a database or data storage. As another example, the functional imaging data can be provided by acquiring the functional imaging data with an appropriate imaging system.

As described above, the functional imaging data can include functional magnetic resonance images or functional magnetic resonance data acquired with an MRI system. Such functional magnetic resonance images or data can be acquired from a subject while the subject is performing a functional task (i.e., activation-based data) or while the subject is in a resting state (i.e., resting state data). For activation-based data, the functional task performed by the subject is preferably associated with the underlying neuropsychiatric, neurodevelopmental, neurobehavioral, or other neurological disorder.

In some embodiments, the functional imaging data can include activation maps, including activation-based maps, resting-state maps, or both. When the functional imaging data does not include previously generated activation maps, the method can include generating one or more activation maps from the functional imaging data, as indicated at step 204.

Examples of data processing and data analysis pipelines that can be implemented for acquiring, processing, and analyzing functional imaging data are described below in more detail. It will be appreciated by a person having ordinary skill in the art, however, that conventional data acquisition, processing, and analysis techniques can also be implemented to acquire, process, and analyze functional imaging data.

Clinical data associated with the subject are also provided, as indicated at step 206. As an example, the clinical data can be provided by retrieving the data from a database or data storage. As described above, the clinical data generally includes data associated with a clinical or behavioral assessment or characterization of the subject. As such, the clinical data generally provides information about the symptoms or behavior exhibited in the subject and associated with a particular neuropsychiatric, neurodevelopmental, neurobehavioral, or other neurological disorder.

The one or more activation maps and associated clinical data can then be processed to generate a biomarker associated with a neuropsychiatric, neurodevelopmental, neurobehavioral, or other neurological disorder, as indicated at step 208. In general, the biomarker correlates the clinical and/or behavioral assessment or characterization of a subject with the neural signature represented by the neuronal activity depicted in the activation maps based on a correlation computed using a multivariate classifier. In some embodiments, the activation maps and associated clinical data are combined in a matrix before being processed to generate the biomarker. For instance, the matrix can be formed such that the rows of the matrix correspond to particular regions in the brain and such that the columns correspond to the various data types (e.g., data from the activation maps and the clinical data).

As one example, the biomarker can include covariance patterns or co-varying traits expressed in the form of interregional correlation or association matrices, which can be analyzed to extract qualitative and quantitative summaries, characteristics, or indices of interaction patterns in brain network organization (i.e., interactome or connectome mapping). Complex network-based analyses are thus used to reveal hierarchical modularity in functional and structural brain activity and connectivity across neuropsychiatric, neurodevelopmental, neurobehavioral, or other neurological disorders and across subsets of valenced conditions (e.g., functional tasks). Biomarkers generated in this manner provide the ability to define organizational and disorganizational principles for human mental disease networks, to determine the interconnections or interactions among classically defined psychiatric diagnosis classes, and to develop a logical basis for a novel systems approach to psychiatric disease classification.

In some embodiments, principal component analysis, or similar statistical analyses, can be used to produce a first-degree approximation for examining brain-wise extensive interregional co-varying patterns across subjects and conditions. These analyses can generate group level spatial component images. The loading scores of individual subjects for a particular component (i.e., an index of how much each subject contributes to a particular component) are tested via that particular component's correlation with other psychological or physiological factors of interest (e.g., factors derived from the provided clinical or additional data). This testing infers the functionality of the connectivity pattern depicted in the component image associated with the tested component. These group level spatial component images, or metrics derived or computed therefrom, can constitute a biomarker associated with a particular neuropsychiatric, neurodevelopmental, neurobehavioral, or other neurological disorder.

Figure 3A:
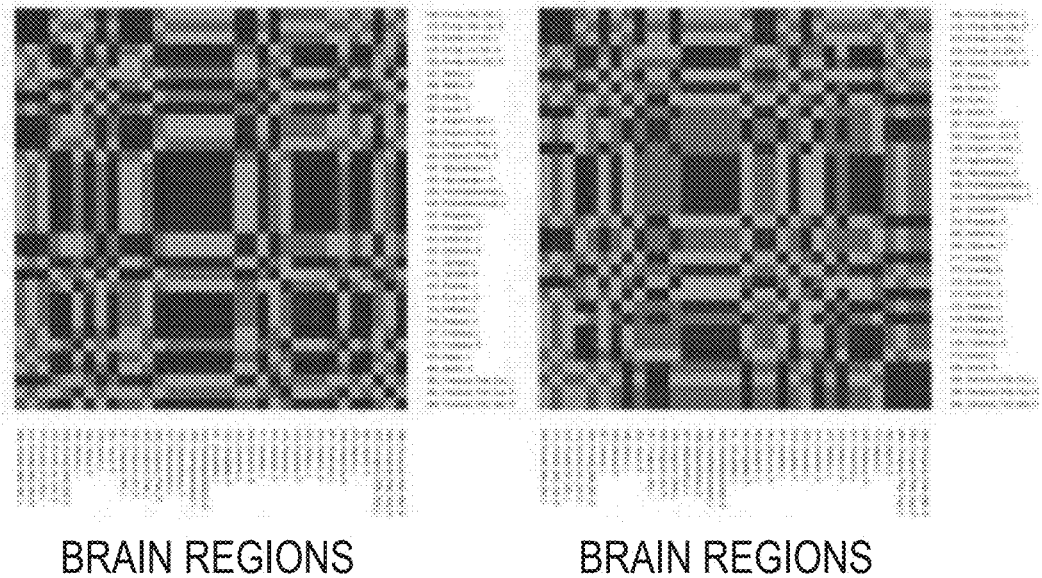
FIGS. 3A and 3B illustrate example outputs from a thresholding correlation analysis performed on data acquired from paranoid schizophrenic patients and from healthy controls.
Figure 3B:
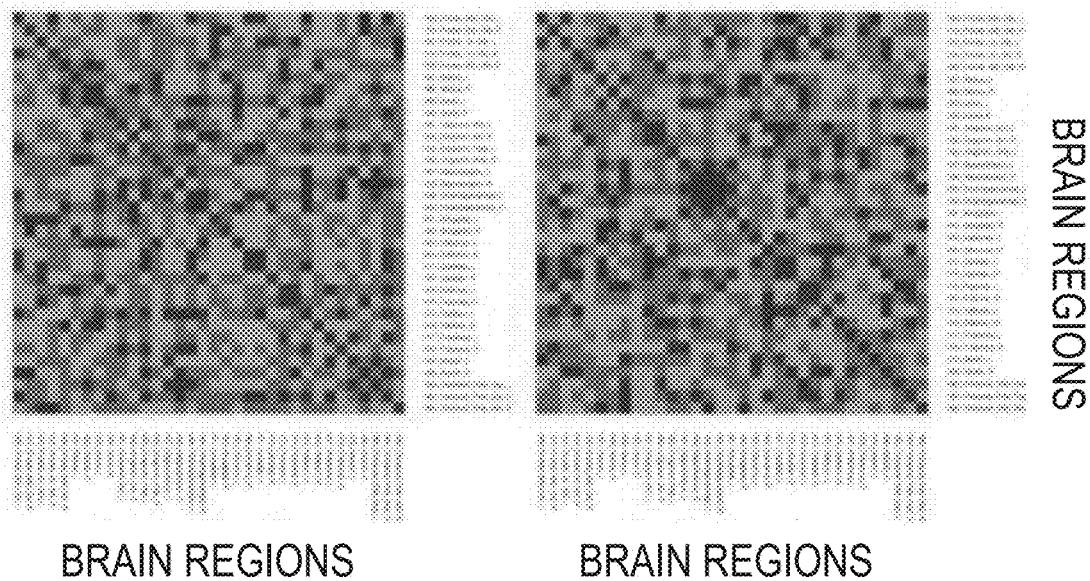

In some embodiments, thresholding correlation analysis is performed to detect brain-wise focal interregional co-varying traits across subjects and conditions. One example of thresholding correlation analysis includes a seed analysis. The thresholding correlation analysis produces group level interregional correlation maps, or images, that can be used for graph theory-based connectome mapping. These group level interregional correlation maps, or metrics derived or computed therefrom, can constitute a biomarker associated with a particular neuropsychiatric, neurodevelopmental, neurobehavioral, or other neurological disorder. Examples of group level interregional correlation maps generated for paranoid schizophrenic patients and healthy controls are illustrated in FIG. 3A and FIG. 3B, respectively.

Figure 4:
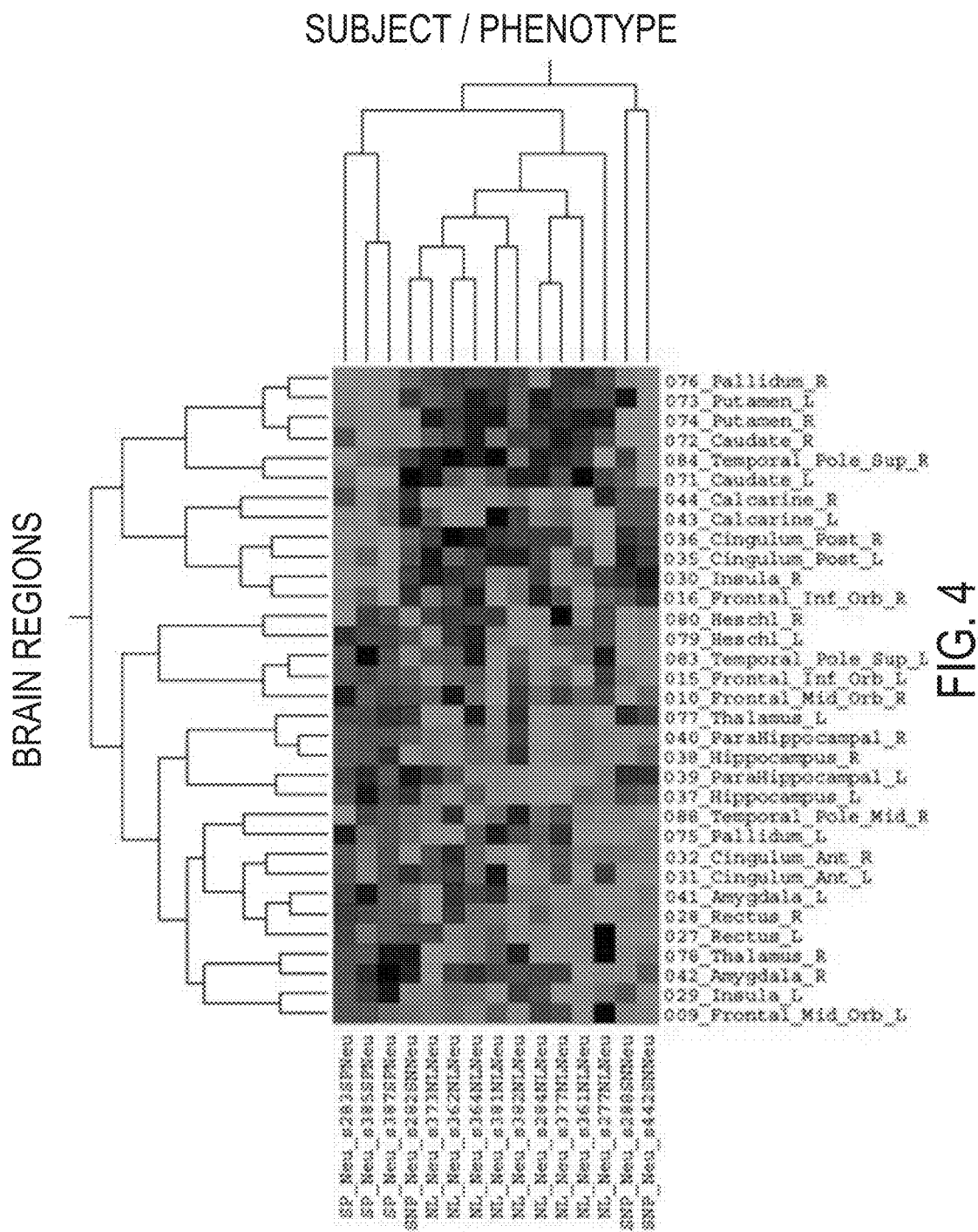
FIG. 4 illustrates an example output from a two-way hierarchical clustering analysis.

In some embodiments, hierarchical clustering analysis is performed to group brain regions with similar activation levels across subsets of valenced conditions (e.g., functional tasks) into clusters or networks. This analysis reveals linearly separable co-varying patterns across neuropsychiatric, neurodevelopmental, neurobehavioral, or other neurological disorders. As one example, the output of the hierarchical clustering analysis can include results projected in a derived multidimensional space of latent dimensions. This output, or metrics derived or computed therefrom, can constitute a biomarker associated with a particular neuropsychiatric, neurodevelopmental, neurobehavioral, or other neurological disorder. It should be appreciated that other suitable clustering algorithms can also be implemented to generate biomarkers. An example output of a hierarchical clustering algorithm, which can be referred to as a cluster map, is illustrated in FIG. 4.

In some embodiments, feature extraction can be used to induce complex hidden dimensions of brain-wide activity and connectivity levels across valenced conditions to define various phenoclusters of brain regions and modules in health and in the diseased brain. These hidden dimensions might not be linearly separable, but are contemplated to have much closer correlations with neuropsychiatric symptom measures. In some other embodiments, dimensionality reduction techniques based on machine learning algorithms, pattern recognition techniques, or both, can be used to induce these complex hidden dimensions. Example machine learning algorithms include those based on neural networks and support vector machine techniques. The output of these analyses, or metrics derived or computed therefrom, can constitute a biomarker associated with a particular neuropsychiatric, neurodevelopmental, neurobehavioral, or other neurological disorder.

In some embodiments, the machine learning algorithm can be trained on a database that includes on or more of the following: relevant functional imaging data, relevant other imaging data, relevant physiological data, relevant clinical data, relevant genetic data, and relevant epigenetic data. Such data can be relevant when they are associated with the particular neuropsychiatric, neurodevelopmental, neurobehavioral, or other neurological disorder, or with symptoms associated with the particular disorder.

In some embodiments, algorithms for estimating graph theory-based network organizational measures based on derived structural magnetic resonance imaging and fMRI regional measures (e.g., resting state and under valenced conditions), can be used to reveal topological features in brain connectome patterns across dimensional domains. The output of these analyses, or metrics derived or computed therefrom, can constitute a biomarker associated with a particular neuropsychiatric, neurodevelopmental, neurobehavioral, or other neurological disorder.

In still other embodiments, the biomarker can be generated by performing combinations of the analysis techniques described above. For instance, the biomarker can be generated by first performing feature extraction or dimensionality reduction, as described above, and then performing a classification analysis on the resulting output. As an example, the classification analysis can include implementing a multivariate classifier, such as the hierarchical clustering of thresholding correlation analysis described above.

Referring again to FIG. 2, the generation of the biomarkers described above can be supplemented with other system-level biological measures, which can be provided in additional functional imaging data, other imaging data, physiological data, genetic data, or epigenetic data. Thus, in some embodiments, the biomarkers can also be generated in dependence on additional data that can be provided, as indicated at step 210. Examples of additional data include other imaging data, physiological data, additional clinical data, genetic data, and epigenetic data. When using multiple different data types to generate the biomarker, appropriate multivariate analyses are implemented, such as those described above.

A report can then be generated, as indicated at step 212, based on the generated biomarker. As one example, the report can include displaying the biomarker on a display. As another example, generating the report can include displaying or outputting other information, such as data plots or other reports based on biomarkers generated by processing the received data.

In some embodiments, the biomarkers that are generated in step 208 can also be used to evaluate the functional imaging experiment or paradigm based on prediction performance estimations. The functional imaging experiment or paradigm can then be suitably updated for improved performance, whether for imaging the same subject again of for imaging of future subjects. Examples of prediction performance estimations include Bayes risk lower bound estimates by k-nearest-neighbor, bench mark performance estimates by discriminant analysis methods, and real-world performance estimates by machine learning methods.

Figure 5:
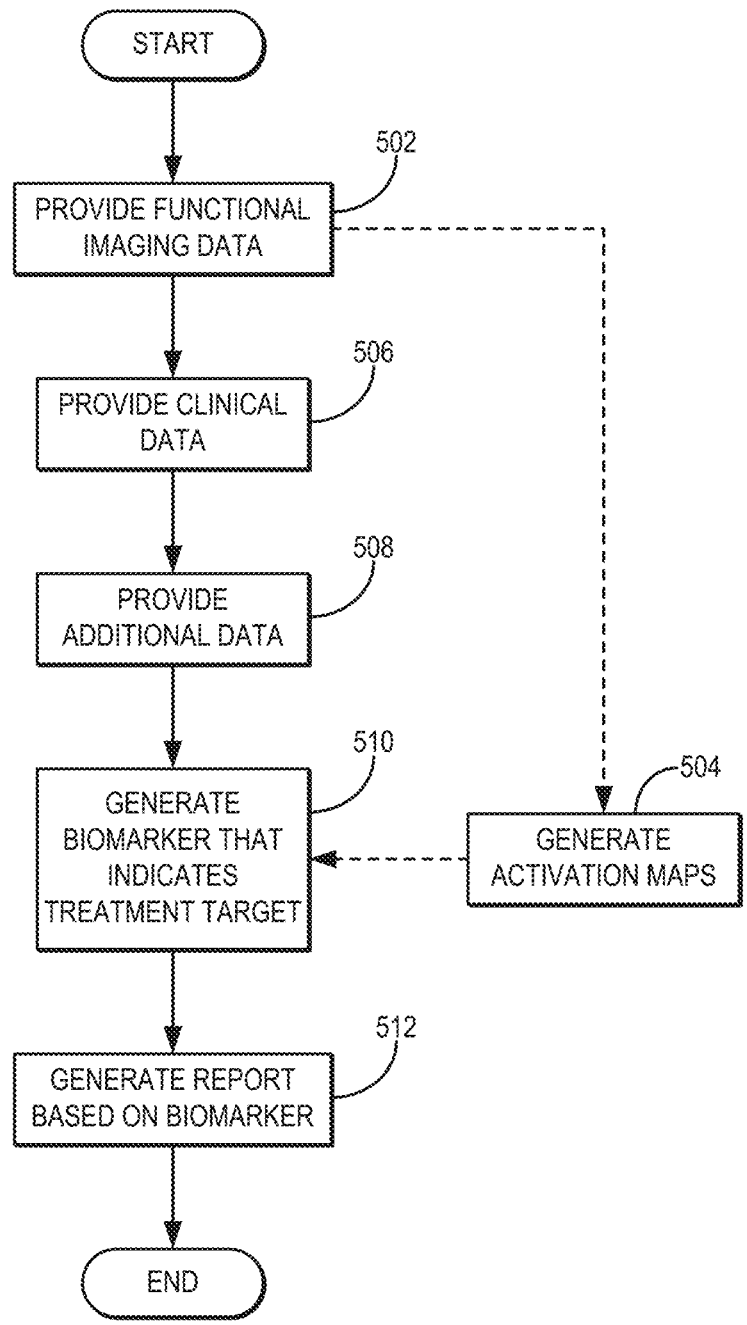
FIG. 5 is a flowchart setting forth the steps of an example method for generating a biomarker that indicates a treatment target for a particular neuropsychiatric, neurodevelopmental, neurobehavioral, or other neurological disorder based on functional imaging data acquired from a subject's brain and based on associated clinical data and additional data acquired from the subject.

Referring now to FIG. 5, a flowchart is illustrated as setting forth the steps of an example method for generating a biomarker that indicates a treatment target. The biomarker is generally based on multiple different data types that include at least functional imaging data and clinical data.

In one aspect, the treatment target can be a functional treatment target, in which the biomarker identifies transdiagnostic signatures associated with a particular neuropsychiatric, neurodevelopmental, neurobehavioral, or other neurological disorders, or with symptoms thereof. Such a biomarker is useful for identifying different indications for an existing therapeutic.

In another aspect, the treatment target can be an anatomical treatment target, whereby the biomarker identifies regions in the brain associated with a particular neuropsychiatric, neurodevelopmental, neurobehavioral, or other neurological disorder, or with symptoms thereof. Such a biomarker is useful for identifying anatomical regions or related neural signatures that can be targeted for treatment, such as by deep brain stimulation ("DBS") or the like.

The method includes providing functional imaging data, as indicated at step 502. As one example, the functional imaging data can be provided by retrieving the functional imaging data from a database or data storage. As another example, the functional imaging data can be provided by acquiring the functional imaging data with an appropriate imaging system.

As described above, the functional imaging data can include functional magnetic resonance images or functional magnetic resonance data acquired with an MRI system. Such functional magnetic resonance images or data can be acquired from a subject while the subject is performing a functional task (i.e., activation-based data) or while the subject is in a resting state (i.e., resting state data). For activation-based data, the functional task performed by the subject is preferably associated with the underlying neuropsychiatric, neurodevelopmental, neurobehavioral, or other neurological disorder.

In some embodiments, the functional imaging data can include activation maps, including activation-based maps, resting-state maps, or both. When the functional imaging data does not include previously generated activation maps, the method can include generating one or more activation maps from the functional imaging data, as indicated at step 504.

Examples of data processing and data analysis pipelines that can be implemented for acquiring, processing, and analyzing functional imaging data are described below in more detail. It will be appreciated by a person having ordinary skill in the art, however, that conventional data acquisition, processing, and analysis techniques can also be implemented to acquire, process, and analyze functional imaging data.

Clinical data associated with the subject are also provided, as indicated at step 506. As an example, the clinical data can be provided by retrieving the data from a database or data storage. As described above, the clinical data generally includes data associated with a clinical or behavioral assessment or characterization of the subject. As such, the clinical data generally provides information about the symptoms or behavior exhibited in the subject and associated with a particular neuropsychiatric, neurodevelopmental, neurobehavioral, or other neurological disorder.

Additional data associated with the subject are also provided, as indicated at step 508. Examples of additional data include other imaging data, physiological data, additional clinical data, genetic data, and epigenetic data. When using multiple different data types to generate the biomarker, appropriate multivariate analyses are implemented.

The one or more activation maps and associated clinical and additional data that have been provided can then be processed to generate a biomarker that indicates a treatment target associated with a particular neuropsychiatric, neurodevelopmental, neurobehavioral, or other neurological disorder, or with symptoms or behaviors associated with such disorders, as indicated at step 510. In general, the biomarker correlates the neural signature represented by the neuronal activity depicted in the activation maps with the clinical and/or behavioral assessment or characterization of a subject represented by the clinical data and the set of system-level biological measures represented by the additional data.

A report can then be generated, as indicated at step 512, based on the generated biomarker. As one example, the report can include displaying the biomarker on a display. As another example, generating the report can include displaying or outputting other information, such as data plots or other reports based on biomarkers generated by processing the received data.

The biomarker indicative of a treatment target can be generated using one or more of the analytical techniques described above with respect to FIG. 2. As one example, a feature extraction or dimensionality reduction analysis can be performed first followed by a classification analysis, such as a classification analysis based on a machine learning algorithm or other classifier.

Figure 6A:
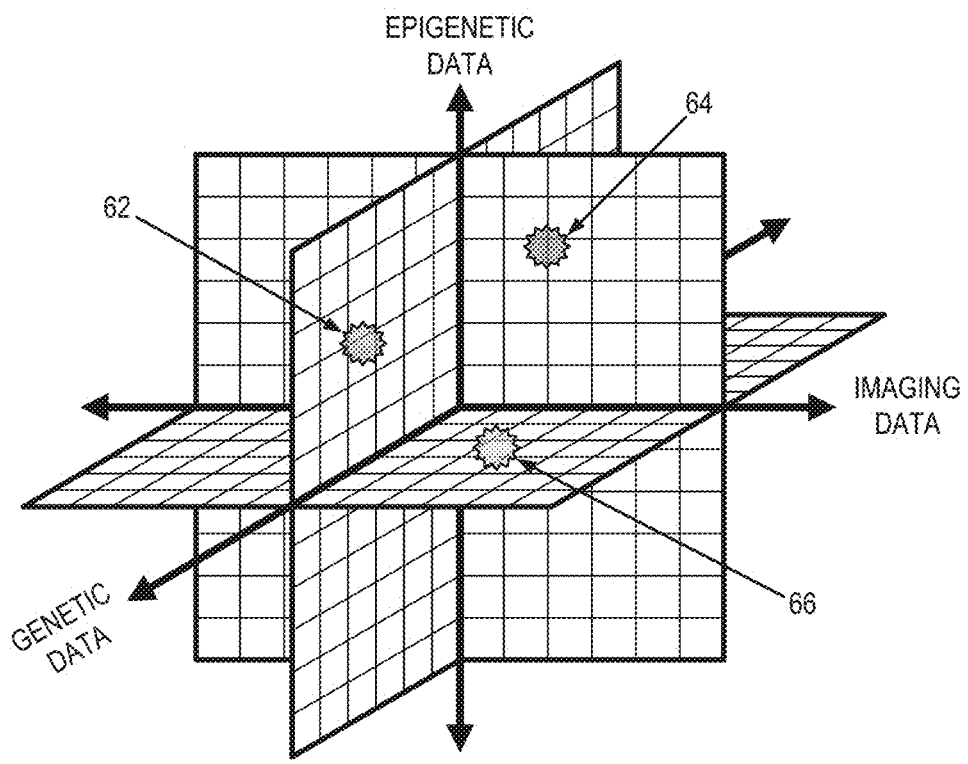
FIG. 6A illustrates an example multidimensional parametric space that can be used to define biomarkers that indicate functional or anatomical targets for treating a particular neuropsychiatric, neurodevelopmental, neurobehavioral, or other neurological disorder.

An example output is shown in FIG. 6A, which illustrates a multidimensional parametric space that, in this example, is associated with imaging data, genetic data, and epigenetic data. Based on the analyses for generating the treatment target biomarker, correlated disorders and symptoms will be clustered at certain locations in this multidimensional parametric space.

For example, data points clustered near region 62 may be associated with bipolar disorder with mania, data points clustered near region 64 may be associated with major depression with anhedonia, and data points clustered near region 66 may be associated with geriatric depression with memory loss. Accordingly, the clustering of data points (based on a particular subject's functional imaging, clinical, and additional data) in the multidimensional parametric space defines a biomarker that indicates targeting for neuropsychiatric, neurodevelopmental, neurobehavioral, or other neurological disorder treatment.

These biomarkers can be used to identify targets for therapeutics. In one aspect, the biomarkers provide transdiagnostic signatures of neuropsychiatric, neurodevelopmental, neurobehavioral, or other neurological disorders. Based on these transdiagnostic signatures, a therapeutic developed for one indication could be identified as having therapeutic utility in other indications. For instance, the biomarkers can be used to identify neural circuits associated with particular neuropsychiatric, neurodevelopmental, neurobehavioral, or other neurological disorders or with symptoms thereof. In some other aspects, the biomarkers provide information about anatomical targets, such as regions of the brain that are associated with particular neuropsychiatric, neurodevelopmental, neurobehavioral, or other neurological disorders, or with symptoms thereof.

Figure 6B:
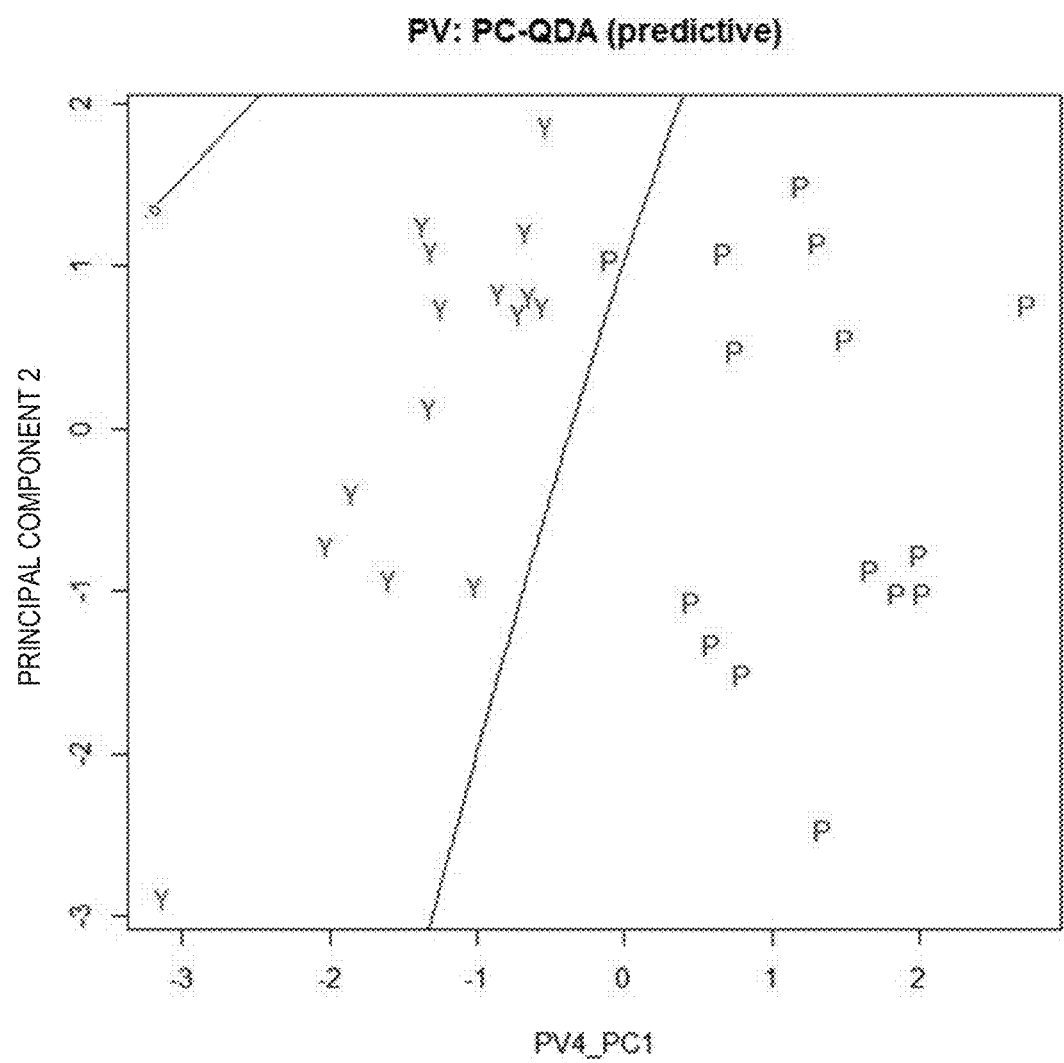
FIG. 6B illustrates an example classifier map based on a two-dimensional parametric space, and in which groups of individuals are classified based on the performance of two different functional tasks.

FIG. 6B illustrates an example classifier map that can be generated using the systems and methods described here. In this particular example, the classifier map depicts data classified into two different groups ("Y" and "P"). It will be appreciated by those skilled in the art that while FIG. 6B illustrates a simple parametric space, classification can occur in larger multidimensional spaces, such as the multidimensional space illustrated in FIG. 6A.

In the example illustrated in FIG. 6B, the classifier map was generated using a support vector machine multivariate classifier algorithm via 10-fold cross-validation using a random partition of the effect size estimates of the desired comparison contrast at multiple regions-of-interest extracted from each subject's individual statistical model. In this example, the two groups correspond to two different functional tasks presented to the same 15 healthy normal controls; however, the groups can also represent other classifications, including groups of correlated functional imaging data, clinical data, and additional data.

In this particular example shown in FIG. 6B, the effect size estimates of each stimulus type ("Y" and "P") at four ROIs were extracted from each subject's individual statistical model and entered into a multivariate pattern analysis ("MVPA") procedure, and the effect size samples were standardized and dimensionality-reduced via a PCA, before being entered into the SVM-based classification analysis. In an implementation for assess treatment of patients with BPD, however, the effect size estimates of the desired comparison contrast (e.g., [Negative Words vs. Neutral Words]×[No-Go vs Go]) at several ROIs (e.g., ventral medial orbital frontal cortex, amygdala) can be extracted from each subject's individual statistical model and entered into an MVPA, or other suitable procedure, and the effect size samples are standardized and dimensionality-reduced via a PCA, before entered into a SVM-based classification analysis, or other suitable multivariate classifier.

As one example, a classifier map can be generated based on functional imaging data, clinical data, and possibly additional data to classify a group of patients having a particular disorder before and after receiving a particular treatment. This type of classifier map can depict groups of individuals who positively responded to the treatment and groups of individuals who did not positively response to the treatment. Using this classifier map as a priori information, an individual patient with the same disorder can then have their data mapped onto the classifier map using a suitable multivariate classifier.

Based on the location of the individual's data relative to the centers of mass for the different groups, an indication of the patient's treatment response can be achieved. Using this approach, quantitative metrics can be derived from classifier maps obtained from a subject over a period of time during which the subject was treated with a particular therapeutic or other treatment regimen and used to evaluate the efficacy of that therapeutic or treatment.

Figure 6C:
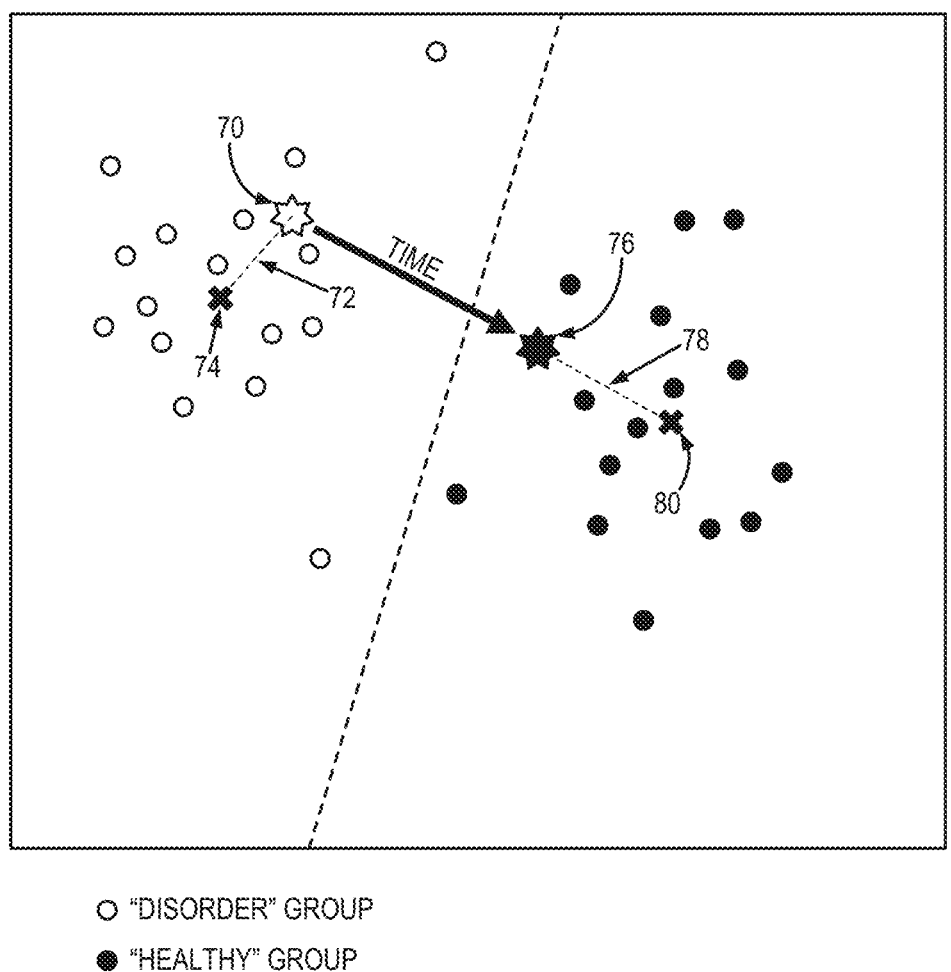
FIG. 6C illustrates an example classifier map, in which correlated data for groups of individuals have been classified based on having a particular disorder or not, and in which an individual's correlated data is mapped onto the classifier map before and after receiving an example treatment.

For example, as illustrated in FIG. 6C, an individual's correlated data may be initially mapped to a location 70 associated with a group of patients with the same disorder as the individual. This initial location 70 can be quantified based on a distance 72 from a center-of-mass 74 for the "disorder" group. Following treatment, the individual's correlated data may change such that the correlated data are now mapped to a location 76 that is associated with a group of healthy controls. This follow-up location 76 can be quantified based on a distance 78 from a center-of-mass 80 of the "healthy" group. The distance between initial location 70 and the follow-up location 76 can also be computed and used to evaluate the efficacy of the treatment. As such, the cluster maps can be used to evaluate the degree of efficacy for a particular treatment and can be used in translational studies to evaluate the treatment over a period of time and across various different individuals and disorders.

Figure 6D:
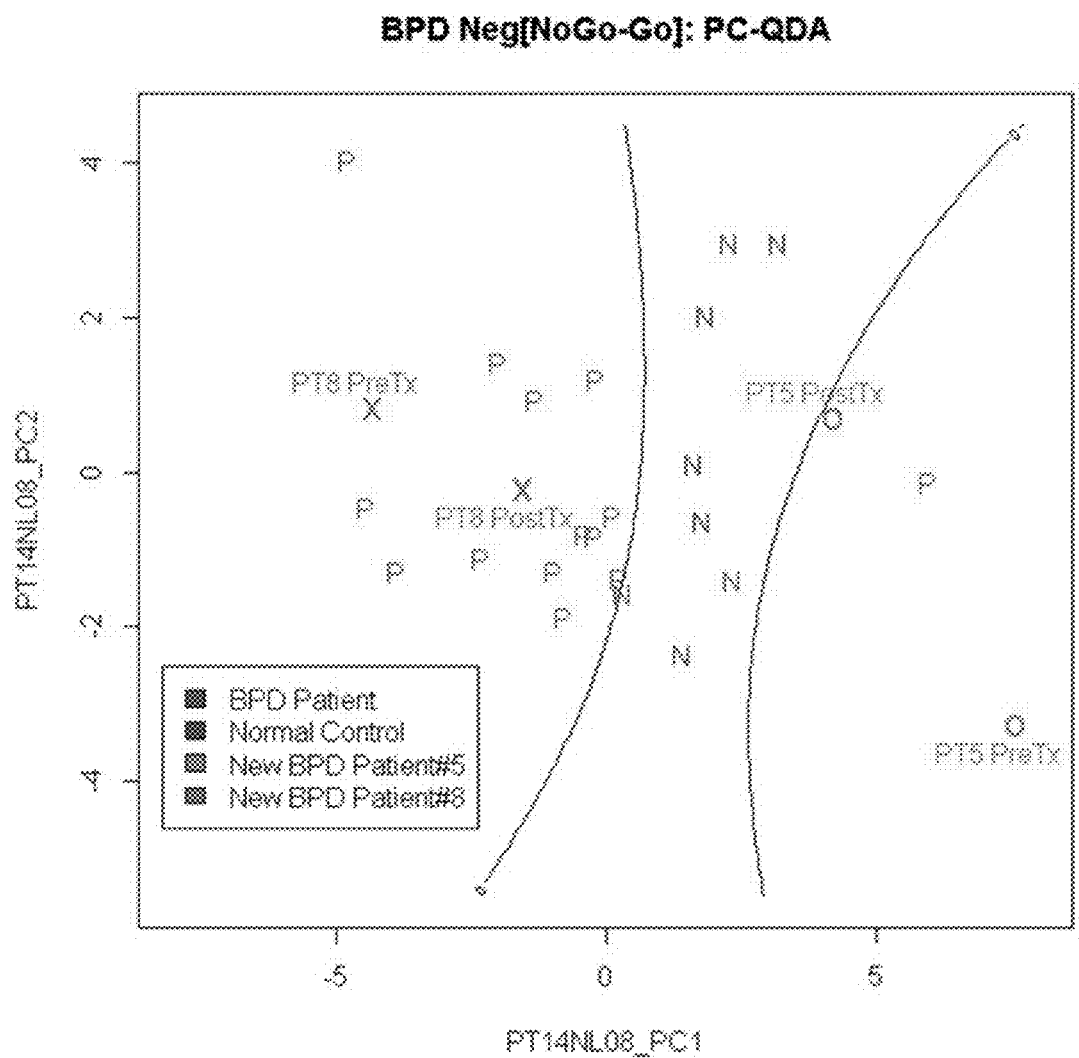
FIG. 6D illustrates another example classifier map, in which correlated data for groups of individuals have been classified as having BPD or not, and in which two patients' correlated data are mapped onto the classifier map before and after receiving treatment.

Another example of using a classifier map to evaluate treatment response, or to otherwise monitor one or more patients over time, is illustrated in FIG. 6D. In this example, the classifier map depicts groups of correlated data that have been classified as corresponding to patients with BPD ("P") or to normal controls ("N"). The correlated data includes functional imaging data that were acquired while the individuals were performing an emotional Go/No-Go task. The classifier map depicted in FIG. 6D was generated using a Support Vector Machine (SVM) algorithm via 10-fold cross-validation using random partitions of the given sample of the effect size estimates of the key comparison contrast (Negative Words [NoGo vs Go]) at 17 ROIs from each subject's individual statistical model. The effect size estimates of the key comparison contrast (Negative Words [NoGo vs Go]) at 17 ROIs (ventral medial orbital frontal cortex, amygdala, etc.) were extracted from each subject's individual statistical model and entered into a Multivariate Pattern Analysis (MVPA) procedure, and the effect size samples were standardized and dimensionality-reduced via a PCA, before being entered into the SVM-based classification analysis. The two new BPD patient's pre-treatment ("PreTx") and post-treatment ("PostTx") data were processed using the same PCA projection defined by the groups of BPD patients and normal subjects, such that their treatment-related effects can be evaluated as shown in the classifier map.

Advantageously, such classifier maps can also be used to define a patient population to monitor in clinical trials for new therapeutics. For instance, a classifier map can identify a group of patients with similarly correlated data that would be enriched for monitoring particular biomarkers based on related symptoms or other correlated data.

Having described examples of methods for generating biomarkers in accordance with various aspects of the present invention, a discussion of various data processing and data analysis pipelines that can be implemented for processing and analyzing functional imaging data and other imaging data is now provided.

Figure 7:
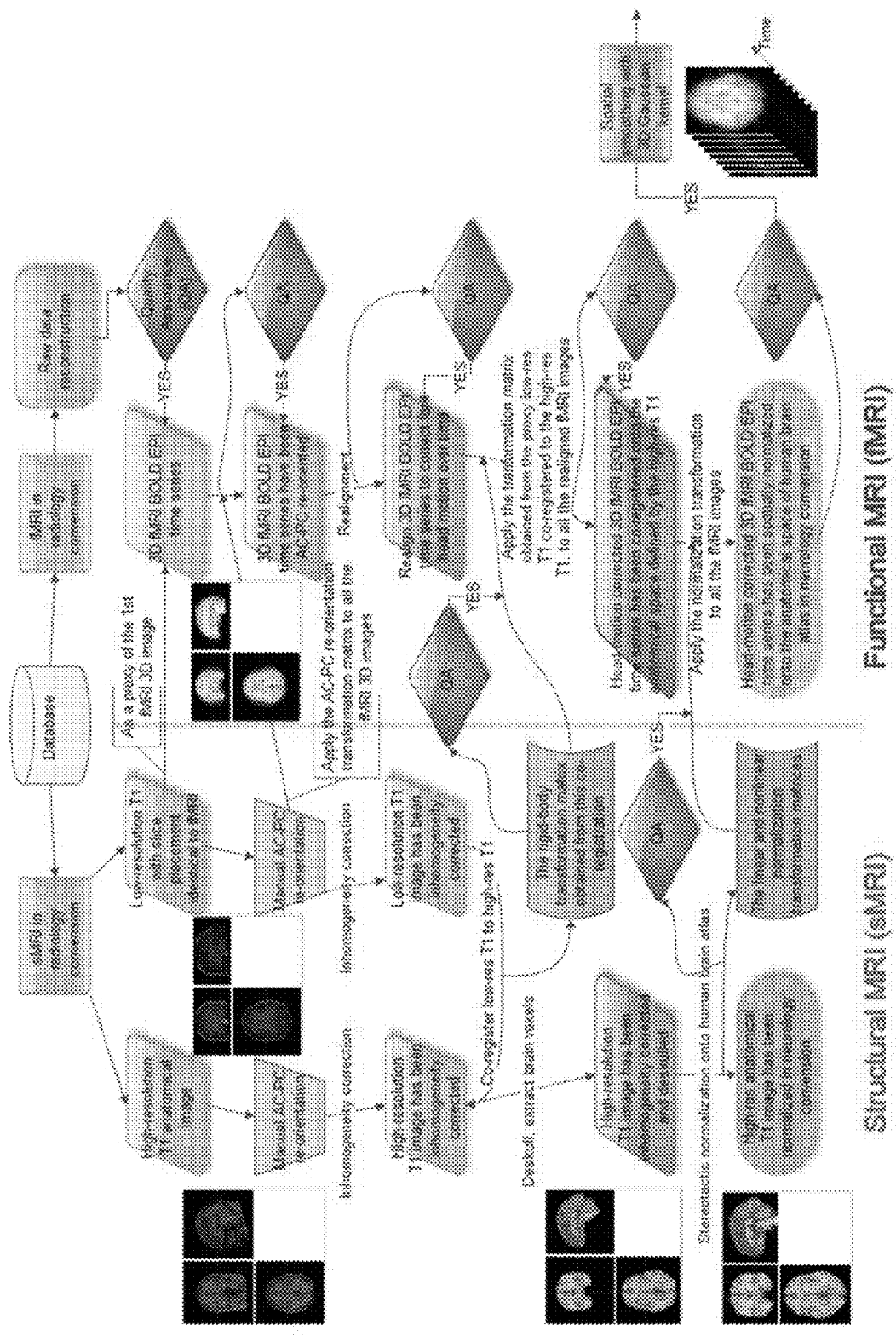
FIG. 7 illustrates an example of data processing pipelines with optimized algorithms for processing functional and structural imaging data prior to performing fMRI data analyses.

FIG. 7 illustrates an example of data processing pipelines with optimized algorithms for processing functional and structural imaging data prior to performing fMRI data analyses. As one example, the data processing pipelines can include implementing algorithms to define brain regions for blood-oxygen-level dependent ("BOLD") image realignment calculations based on intracranial voxels.

In some embodiments, the data processing pipelines are coupled with specifically designed and tailored scanning protocols or pulse sequences using BOLD measures. For instance, the pulse sequences used to acquire the functional imaging data can be designed to compensate for susceptibility artifacts. The pulse sequences can also be designed to maximize spatial and temporal signal-to-noise ratios for reliably detecting brain activity at the base of the brain and medial temporal lobes. In some instances, the acquisition of functional imaging data with an MRI system can include implementing techniques for z-shimming to reduce susceptibility artifacts resulting in signal void and local distortions in BOLD contrast. These methods can advantageously improve imaging structures such as the amygdala and orbitofrontal cortex, which are implicated in multiple psychiatric disorders.

Figure 8:
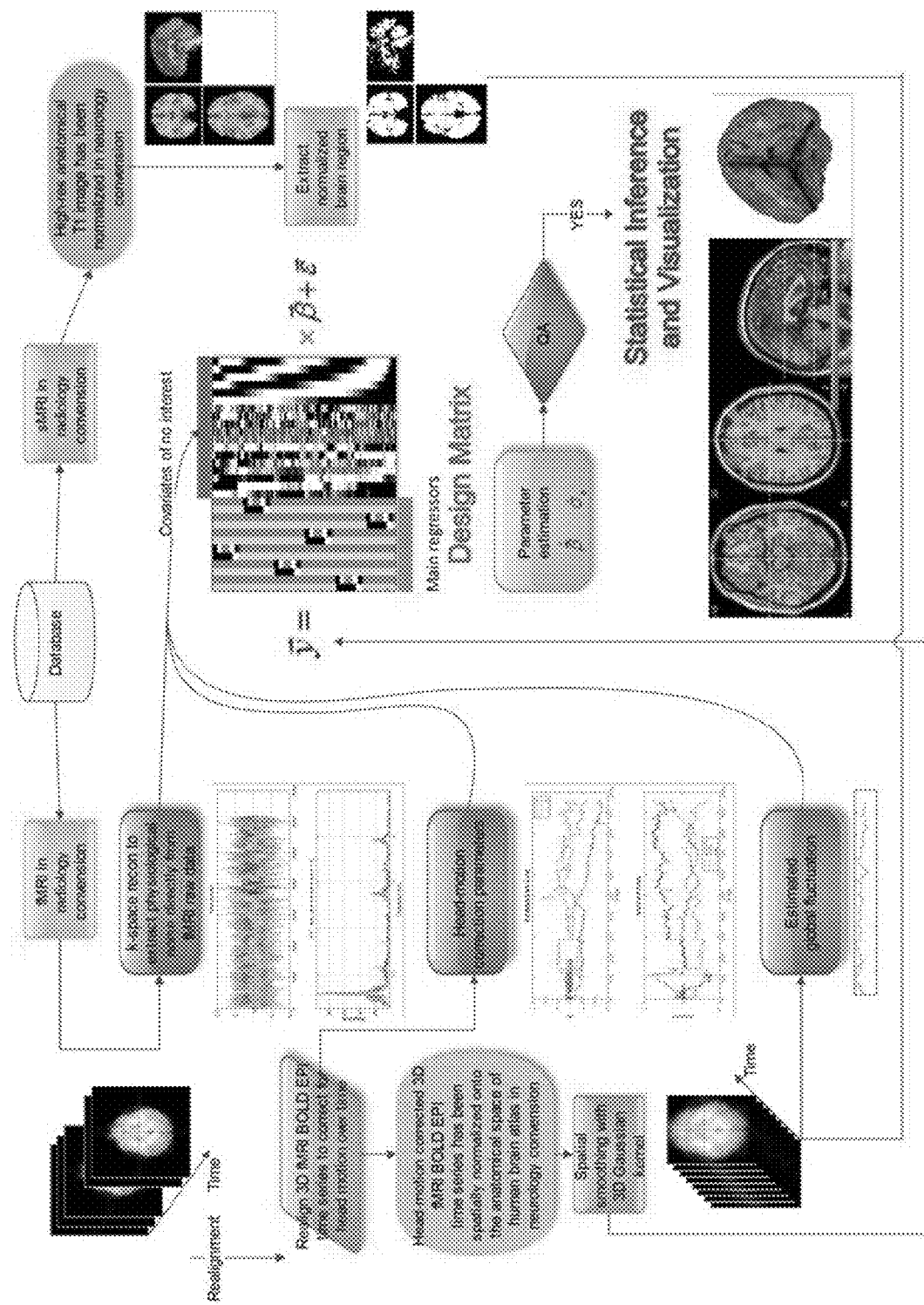
FIG. 8 illustrates an example of an fMRI data analysis pipeline with optimally tailored usage of standardized routines, and enhanced or modified subroutines and modules, that can be implemented to produce a variety of functional measures.

FIG. 8 illustrates an example of an fMRI data analysis pipeline with optimally tailored usage of standardized routines, and enhanced or modified subroutines and modules, that can be implemented to produce a variety of functional measures. As one example, the data analysis pipeline can be used to extract the estimated brain-wide activity and connectivity levels across valenced conditions and during the resting state. As another example, the data analysis pipeline can be used to derive summarized fMRI measures, structural MRI measures, or both, for probing network connectivity endophenotypes of brain circuits (i.e., localizome mapping). Quality assurance ("QA") can be performed at every stage to ensure integrity of the data.

The example fMRI data analysis pipeline illustrated in FIG. 8 can include algorithms to extract physiological noise directly from raw functional imaging data (e.g., BOLD imaging data). The example fMRI data analysis pipeline illustrated in FIG. 8 can also include algorithms to define brain regions and to estimate temporal global fluctuations in four-dimensional ("4D") fMRI time series. As described below, the fMRI data analysis pipeline can also include implementing advanced statistical models, such as multi-level mixed-effects models with structured residual variance functions, to provide reduced estimation bias and improved prediction performance compared to the existing state-of-art data analysis techniques.

A variety of known statistical methods can be implemented to generate activation maps; however, in accordance with some embodiments activation maps can be generated with advanced statistical methods that improve statistical prediction performance and significantly reduce estimation biases.

Thus, in some embodiments, activation maps can be generated using a multi-level mixed-effects model, $$y_{ikt}=f(d_{ikt},\phi)+\varepsilon_{ikt} \quad (1);$$

where $y_{ikt}$ is the adjusted hemodynamic signal at a voxel of the $i^{th}$ subject at the $k^{th}$ trial and the time, t; $d_{ikt}$ is the time of the $t^{th}$ scan of the $k^{th}$ trial on the $i^{th}$ subject; $\phi$ is the set of parameters, $\varepsilon_{ikt}$ is the residuals, and, $$f(\cdot;\cdot)=\phi_{0i}+\phi_{1ik}HRF+\phi_{2ik}HRF' \quad (2);$$

where $\phi_{0i}$ is the baseline parameter for the $i^{th}$ subject, $\phi_{1ik}$ is the magnitude of the principal regressor of the $k^{th}$ trial on the $i^{th}$ subject, $\phi_{2ik}$ is the magnitude of the first derivative of the principal regressor of the $k^{th}$ trial on the $i^{th}$ subject, HRF is the principal regressor defined based on a hemodynamic response function, and HRF' is the first derivative of the HRF with respect to time.

In some embodiments, the multi-level mixed-effects model can also include a nested random-effects structure, with the fixed ($\beta$) and random (b) effects selected via model a selection procedure. As one example, the multi-level mixed-effects model can be defined by, $$\phi_{0i}=\beta_0+b_{0i} \quad (3);$$

$$\phi_{1ik}=\beta_1+b_{1i}+b_{2ik} \quad (4);$$

$$\phi_{2ik}=\beta_2+b_{2i}+b_{2ik} \quad (5);$$

$$b_i=(b_{0i},b_{1i},b_{2i})^T \sim N_3(0,\Psi_1) \quad (6);$$

$$\Psi_1=\text{diag}(\psi_{10},\psi_{11},\psi_{12}) \quad (7);$$

$$b_{ik}=(b_{1i,k},b_{2i,k})^T \sim N_2(0,\Psi_2) \quad (8);$$

$$\Psi_2=\text{diag}(\psi_{21},\psi_{22}) \quad (9);$$

where $\beta_0$ is the fixed effect of the baseline, $b_{0i}$ is the random effect of the baseline for the $i^{th}$ subject, $\beta_1$ is the fixed effect of the magnitude of the principal regressor, $b_{1i}$ is the random effect of the magnitude of the principal regressor for the $i^{th}$ subject, $b_{1i,k}$ is the random effect of the magnitude of the principal regressor for $k^{th}$ trial within the $i^{th}$ subject, $\beta_2$ is the fixed effect of the derivative of the principal regressor, $b_{2i}$ is the random effect of the derivative of the principal regressor for the $i^{th}$ subject, $b_{2i,k}$ is the random effect of the derivative of the principal regressor for the $k^{th}$ trial within the $i^{th}$ subject. The parameter vector of the subject level random effect, $b_i$, follows a normal distribution, $N_3(0,\Psi_1)$, of a zero mean vector, 0, and a diagonal covariance matrix, $\Psi_1$, where $\Psi_{10}$ is the variance of $b_{0i}$, $\psi_{11}$ is the variance of $b_{1i}$, and $\psi_{12}$ is the variance of $b_{2i}$. Likewise, the parameter vector of the trial level random effect within the $i^{th}$ subject, $b_{ik}$, follows a normal distribution, $N_2 (0,\Psi_2)$, of a zero mean vector, 0, and a diagonal covariance matrix, $\Psi_2$, where $\psi_{21}$ is the variance of $b_{1ik}$, and $\psi_{22}$ is the variance of $b_{2ik}$.

In some embodiments, the multi-level mixed-effects model can also include, with or without the nested random-effects structure, an intra-subject power variance function and an autoregressive correlation structure for modeling heteroscedastic and correlated intra-subject residuals, $$\text{cov}(\varepsilon_{ik}) = \sigma^2 G(\phi,\delta)^{1/2} \Gamma(\alpha) G(\phi,\delta)^{1/2} \quad (10);$$

$$G(\phi,\delta) = \text{diag}(\ldots, g^2(\mu_{ikt},\delta_i), \ldots) \quad (11);$$

$$g(\mu_{ikt},\delta_i) = \mu_{ikt}^{\delta_i} \quad (12);$$

$$\mu_{ikt} = f(d_{ikt},\phi) \quad (13);$$

$$\delta = (\delta_1, \ldots, \delta_M)^T \quad (14);$$

$$\Gamma(\alpha) = \text{corr}(\varepsilon_{ik}) = [\text{corr}(\varepsilon_{ikt_1},\varepsilon_{ikt_2})] = [\alpha^{(t_1-t_2)}] \quad (15).$$

The residuals are assumed to follow a normal distribution of a zero mean vector and a covariance matrix in Eqn. (10), where $\varepsilon_{ik}$ is the residuals; $\sigma^2$ is the common variance; $G(\phi,\delta)$ is the diagonal matrix of a power variance function; $\Gamma(\alpha)$ is the autoregressive ("AR") correlation matrix; $g^2$ is the power variance function; $\mu_{ikt}$ is the signal level predicted by the model; $\delta_i$ is the power variance function parameter for the $i^{th}$ subject; and $\alpha$ is the first order AR parameter.

FIG. 9A illustrates a comparison of advanced (top row) versus conventional (bottom row) data analysis methods from an fMRI study investigating the systems-level neuropathophysiology of premenstrual dysphoric disorder ("PMDD"). The results shown are in a single subject with PMDD, performing an emotional Go/No-Go task, and the activation maps (t-maps) represent the interaction contrast of luteal versus follicular stage of the menstrual cycle in the Negative No-Go versus the Neutral No-Go conditions. The advanced method shows significantly higher statistical detection power, which is able to provide significantly less biased estimates and significantly improved prediction performance compared to the statistical methods typically employed in existing state-of-the-art software.

FIG. 9B illustrates coverage probabilities, based on 95% confidence intervals, for the observed values using the advanced and conventional statistical analysis methods. The coverage probabilities (red bars; red crosses are the predicted values) for the observed values (blue circle dots) are 96.77% for the advanced method (left plot), which has achieved the target estimation performance level, and only 74.75% or lower for the conventional method (right plot), which is significantly below the target level of desirable statistical performance.

FIG. 9C illustrates the mean estimation bias measured via a cross-validation z-score. In the advanced data analysis (left plot), the mean estimation bias is 0.71, which is less than 1 standard deviation unit. Using the advanced data analysis techniques described above, all estimation bias points are close to zero. In the conventional data analysis (right plot), the mean estimation bias is 1.91, which is close to two standard deviation units.

Having described examples of methods for generating biomarkers in accordance with various aspects of the present invention, and various data processing and data analysis pipelines that can be implemented for processing and analyzing functional imaging data and other imaging data, an example computer system that can implement these methods is now described.

Figure 10:
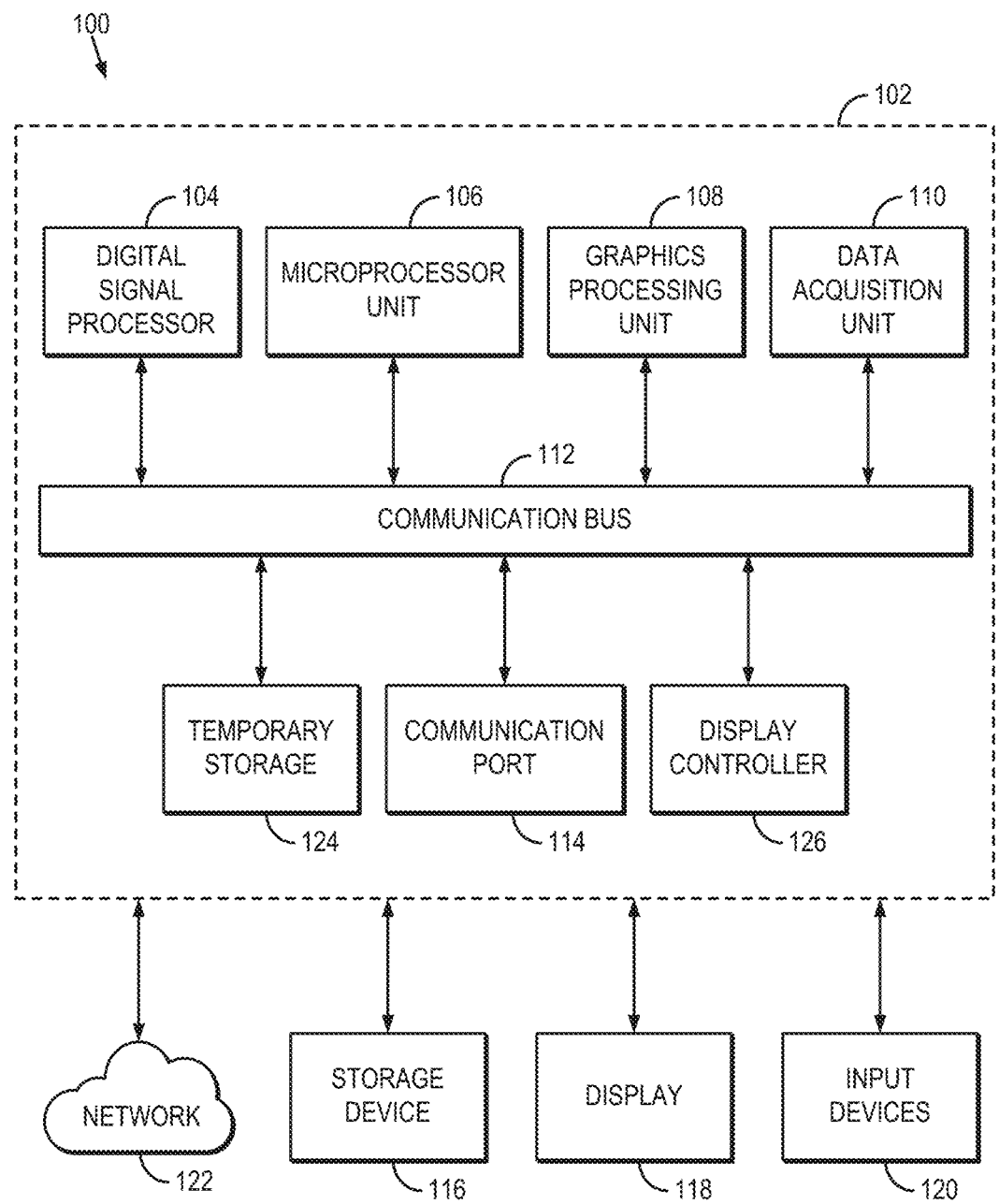
FIG. 10 is a block diagram of an example computer system that can implement the data analysis and biomarker generation methods described herein.

Referring now to FIG. 10, a block diagram shows an example computer system 100 that can be configured to generate biomarkers associated with a particular neuropsychiatric, neurodevelopmental, neurobehavioral, or other neurological disorder, or that indicate a treatment target for such disorders, as described above. The data to be processed (e.g., functional imaging data, clinical data, other imaging data, physiological data, genetic data, epigenetic data) can be provided to the computer system 100 from a database or data storage device, and are received in a processing unit 102.

In some embodiments, the processing unit 102 can include one or more processors. As one non-limiting example, the processing unit 102 may include one or more of a digital signal processor ("DSP") 104, a microprocessor unit ("MPU") 106, and a graphics processing unit ("GPU") 108. The processing unit 102 can also include a data acquisition unit 110 that is configured to electronically receive data to be processed, which may include functional imaging data, clinical data, other imaging data, physiological data, genetic data, and epigenetic data. The data acquisition unit 110 and the one or more processors in the processing unit 102, which may include DSP 104, MPU 106, GPU 108, are all coupled to a communication bus 112. As an example, the communication bus 112 can be a group of wires, or a hardwire used for switching data between the peripherals or between any component in the processing unit 102.

The one or more processors in the processing unit 102 can be configured to receive and processes functional imaging data, clinical data, other imaging data, physiological data, genetic data, epigenetic data. For instance, the DSP 104 can be configured to receive and processes functional imaging data, clinical data, other imaging data, physiological data, genetic data, or epigenetic data. Furthermore, the MPU 106 and GPU 108 can also be configured to process the functional imaging data, clinical data, other imaging data, physiological data, genetic data, or epigenetic data in conjunction with the DSP 104. As an example, the MPU 106 can be configured to control the operation of components in the processing unit 102 and can include instructions to perform processing of the functional imaging data, clinical data, other imaging data, physiological data, genetic data, or epigenetic data on the DSP 104. As another example, the GPU 108 can be configured to process image graphics.

In some embodiments, the DSP 104 can be configured to process the functional imaging data, clinical data, other imaging data, physiological data, genetic data, epigenetic data received by the processing unit 102 in accordance with the algorithms described above. Thus, the DSP 104 can be configured to generate the biomarkers described above by using a multivariate classifier to compute correlations between functional imaging data and clinical data, or between functional imaging data, clinical data, and additional data.

The processing unit 102 preferably includes a communication port 114 in electronic communication with other devices, which may include a storage device 116, a display 118, and one or more input devices 120. Examples of an input device 120 include, but are not limited to, a keyboard, a mouse, and a touch screen through which a user can provide an input.

The storage device 116 is configured to store data and images, whether provided to or processed by the processing unit 102. The display 118 is used to display images, such as images that may be stored in the storage device 116, and other information. Thus, in some embodiments, the storage device 116 and the display 118 can be used for displaying images before and after processing and for outputting other information, such as data plots or other reports based on biomarkers generated by processing the received data.

The processing unit 102 can also be in electronic communication with a network 122 to transmit and receive data, including functional imaging data, clinical data, other imaging data, physiological data, genetic data, epigenetic data, and other information. The communication port 114 can also be coupled to the processing unit 102 through a switched central resource, for example the communication bus 112.

The processing unit 102 can also include a temporary storage 124 and a display controller 126. As an example, the temporary storage 124 can store temporary information. For instance, the temporary storage 124 can be a random access memory.

Example 1: Biomarker for Diagnosing Borderline Personality Disorder

In this example, 16 patients with borderline personality disorder (15 of them female; 15 of them right-handed; mean age=31.25 years, range=19-50 years) and 14 healthy comparison subjects (10 female; 12 right-handed; mean age=23.8 years, range=18-31 years) were studied. Borderline diagnoses were confirmed with the International Personality Disorder Examination (criteria score range=5-9, dimensional score range=10-18; mean=14.9, SD=2.28). None of the participants had significant medical or neurological conditions. There was no significant difference in gender composition between the two groups, but there was a significant difference in age (p=0.012). Age was therefore incorporated, along with gender and handedness, as a covariate in the imaging data analysis.

The Multidimensional Personality Questionnaire was used to relate specific clinical symptom measures to functional neuroimaging results with a focus on negative emotion and on constraint. Negative emotion is a construct that taps proneness to experience anxiety, anger, and related states of negative engagement. Constraint is a construct reflective of control and harm avoidance; a high level of constraint reflects tendencies to inhibit and restrain impulse expression.

fMRI Paradigm

Participants underwent scanning while they performed an emotional linguistic go/no-go task developed to investigate neurocircuitry underlying the interaction between emotion and motor inhibition, with verbal stimuli containing themes salient for individuals with borderline personality disorder. Behavioral response was based on orthographically based cues: participants were instructed to perform a right-index-finger buttonpress immediately after (silently) reading a word appearing in normal font (go trial) and to inhibit this response after reading a word in italicized font (no-go trial). Button-press responses and reaction times were recorded. A total of 192 distinct linguistic stimuli were used (64 negative, 64 positive, 64 neutral). Words were balanced across all valence conditions for frequency, word length, part of speech, and imageability.

The task was presented in a block design that included 24 blocks (six blocks per run, four runs total). The six blocks per run represented the six main conditions (neutral go, neutral no-go, negative go, negative no-go, positive go, positive no-go), the presentation of which was counterbalanced to control for order and time effects across runs. Go blocks contained 16 go trials (100% go trials), and no-go blocks contained 10 go trials (62.5% go trials) and six no-go trials (37.5% no-go trials), presented in pseudorandomized order to establish prepotent motor response yet have ample no-go trials. Each word was presented individually in white letters on a dark background for 1.5 sec followed by a 0.75-sec interstimulus interval (total block duration=36 sec). Each block was followed by a 20-sec rest period during which a fixation cross was displayed. A shortened practice run using different words preceded the experimental runs to ensure that participants understood and could follow the task instructions.

When the scanning was completed, participants were removed from the scanner and instructed to perform a word recognition task. They were given a list of the 192 stimulus words (targets) randomly interspersed with 48 distractor words (divided equally into negative, positive, and neutral categories, balanced for the same linguistic qualities as targets) and asked to circle the words they believed they saw during the scanning session. They were then given a word valence rating task, which was also made up of both target and distractor words, and asked to rate the valence of each word on a 7-point Likert-like scale (−3=very negative, 0=neutral, +3=very positive).

Image Acquisition

Structural images were acquired with a three-dimensional high-resolution T1-weighted spoiled gradient-recalled acquisition sequence, and echo planar imaging ("EPI") was used to obtain BOLD functional MR images. After shimming to maximize homogeneity, a series of gradient echo fMRI scans was acquired with a z-shimming algorithm to reduce susceptibility artifacts at the base of the brain. A reference T1-weighted anatomical image with the same slice placement and thickness was acquired immediately before the EPI acquisition.

Image Processing and Data Analysis

Prior to data analysis, functional EPI scans were realigned based on intracranial voxels, functional images were coregistered to the corresponding high-resolution anatomical image based on the transformation of the reference anatomical image to the latter for each individual subject, stereotactic normalization was performed to Montreal Neurological Institute ("MNI") space based on the high-resolution anatomical image, and spatial smoothing was performed with an isotropic Gaussian kernel (full width at half maximum=7.5 mm).

A two-stage general linear model was used to examine the effect sizes of the key group/condition contrasts. First, a voxelwise multiple linear regression model was used at the individual subject level. This model included the principal regressors of interest, which included the stimulus onset times convolved with a prototypical hemodynamic response function, and the covariates of no interest, which included the temporal first-order derivative of the principal regressors, global fluctuations, realignment parameters, and scanning periods. The temporal global fluctuation estimated as the mean intensity within brain of each volume was removed through proportional scaling. Temporal filtering was performed to counter the effects of baseline shifts and higher-frequency noise, and a first-order autoregressive model of the time course was used to accommodate temporal correlation in residuals. Effects at every brain voxel were estimated by a least squares algorithm, and the effect images for each condition were then combined in a series of linear contrasts to be entered into the second-stage, group-level analysis.

Second, at the group level, a random-effects model was used, which accounts for intersubject variability and allows population-based inferences to be drawn. The within- and between-group effects of the hypothesis-driven contrasts were estimated using a least squares algorithm with demographic variables (age, gender, and handedness) incorporated as covariates in the context of an analysis of covariance. These group-level effect estimates generated t-statistic maps, and their statistical significance was evaluated based on random field theory. The statistical inferences were thresholded at a voxelwise p-value and cluster extent ($p<0.005$, uncorrected for multiple comparisons, and a cluster extent of four voxels with a voxel volume of 27 mm$^3$).

Based on a priori hypotheses, regions of interest were the amygdala, the (subgenual) anterior cingulate gyrus, and the medial orbitofrontal cortex. These regions were defined on the basis of previously reported functional imaging studies concerned with impulse control and negative affect regulation. Regions of interest were examined by correcting the voxelwise p-value at the local maximum of the nearest cluster. Behavioral data (e.g., response times, error rates, recognition rates, and valence ratings) were analyzed using repeated measures analysis of variance and subsequent Wilcoxon signed rank-sum tests to focus on marked performance differences across groups and conditions.

Results

Figure 11:
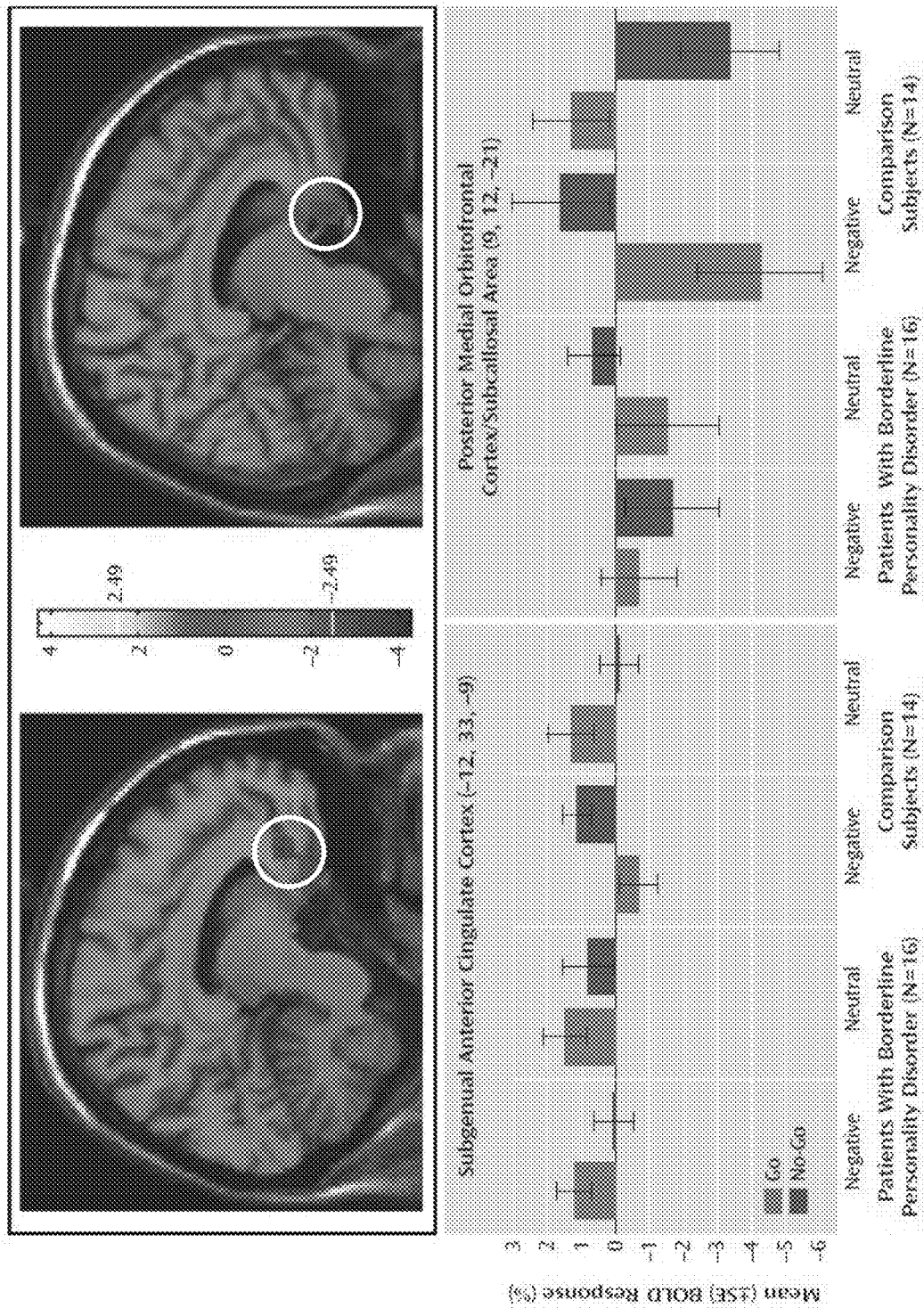
FIG. 11 shows comparisons of neuronal activity between patients with borderline personality disorder (N=16) and healthy comparison subjects (N=14) for the interaction effect between negative (versus neutral) emotional and no-go (versus go) conditions (Neg−Neu×No-Go−Go)

FIG. 11 illustrates BOLD activity changes thresholded at a voxelwise p-value of 0.01 (uncorrected) with a cluster extent of 108 mm$^3$ for the purpose of visualization. Borderline patients showed decreased activity relative to comparison subjects in the subgenual anterior cingulate cortex (left panel; Montreal Neurological Institute [MNI] space, x=−9) and the posterior medial orbitofrontal cortex (right panel; MNI space, x=9). Bar plots show summary values for individual conditions by group in each of the two areas to indicate directionality of BOLD changes driving the interaction effects.

Figure 12:
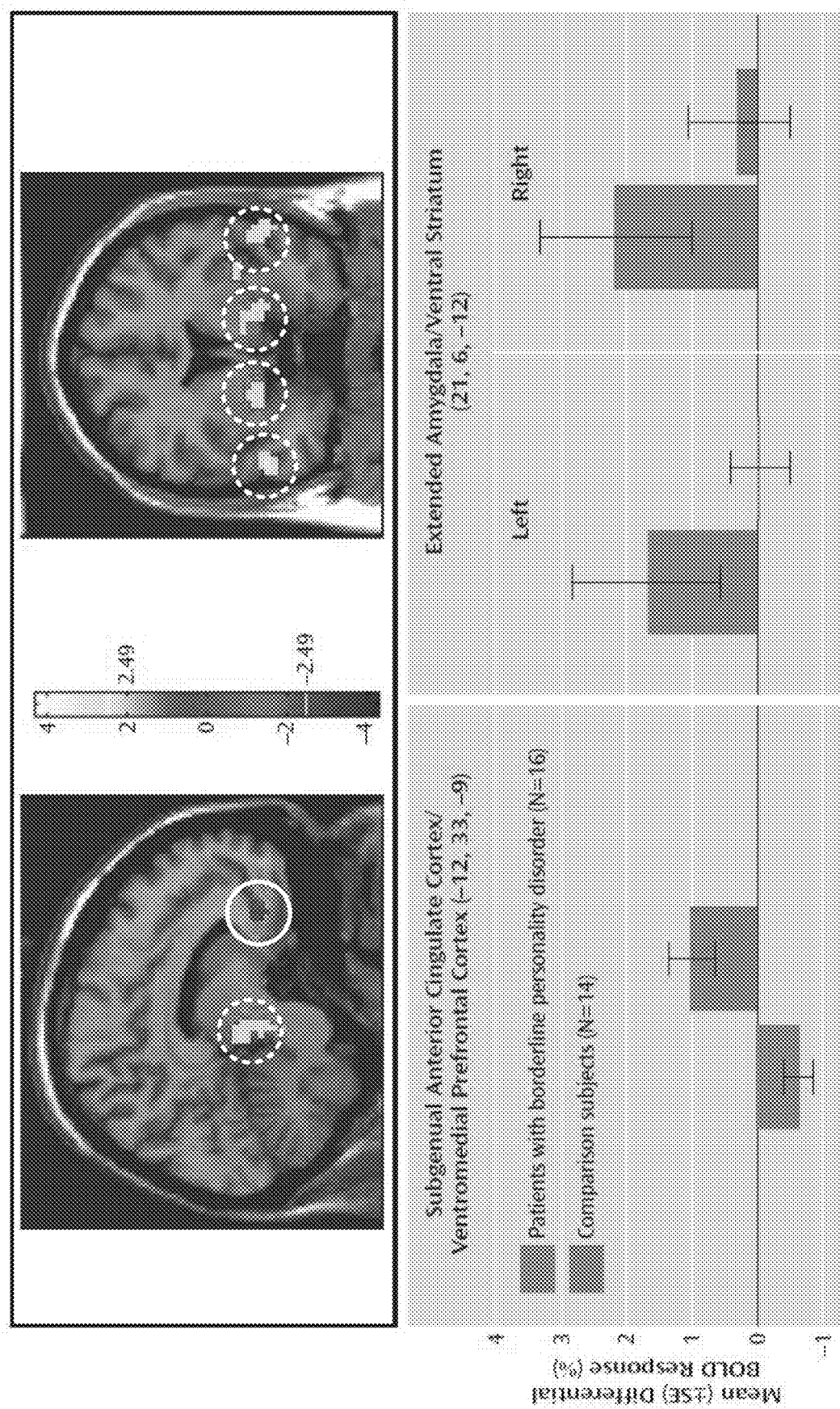
FIG. 12 shows comparisons of neuronal activity between patients with borderline personality disorder (N=16) and healthy comparison subjects (N=14) for the contrast of behavioral inhibition versus no inhibition in the context of negative emotion (Neg[No-Go−Go])

FIG. 12 illustrates BOLD activity changes are thresholded at a voxelwise p-value of 0.01 (uncorrected) with a cluster extent of 108 mm$^3$ for the purpose of visualization. Borderline patients showed decreased activity relative to comparison subjects in the subgenual anterior cingulate cortex (left panel; Montreal Neurological Institute [MNI] space, x=−9), decreased activity in the posterior medial orbitofrontal cortex (not shown), and increased activity in the left and right extended amygdala and ventral striatum, (right panel; MNI space, y=3). Bar plots show summary values for differential BOLD response at the statistical maxima of the subgenual anterior cingulate cortex and extended amygdale.

Summary

As seen in FIGS. 11 and 12, the example study described above illustrated that patterns of neuronal activity can be used as a biomarker for aiding in the diagnosis of borderline personality disorder. Using the methods described above, these patterns of neuronal activity can be implemented in a multivariate classifier to identify individuals as belonging to a population consistent with the neural signatures associated with borderline personality disorder. To this end, the methods described here can be utilized to provide diagnostic information about whether a patient is likely to have borderline personality disorder.

Example 2: Biomarker for Diagnosing Schizophrenia

In this example, 26 right-handed subjects (6 female, 20 male; mean age=29.85, range 20-44) participated in a study to assess patterns of neuronal activity in patients with schizophrenia. Participants were diagnosed with schizophrenia (n=22) or schizoaffective disorder (n=4) based on the Structured Clinical Interview for the Diagnostic and Statistical Manual of Mental Disorders IV Axis I Disorders. All subjects were receiving anti-psychotic medications [typical (n=4), atypical (n=18), typical and atypical (n=4)], with antipsychotic doses converted to a mean daily dose equivalence of chlorpromazine for each subject (mean=553.19 mg, SD=270.69 mg). Subjects were also taking the following psychotropic medications: mood stabilizers; antidepressants; benzodiazepines; and anti-cholinergic medications. Inclusion criteria included the following: presence of only minimal negative symptoms and cognitive impairment, no history of electroconvulsive therapy within the past year, English as first language or fully fluent in English, and capacity to provide informed consent.

Paranoid delusion severity was based on the persecution/suspiciousness item (P6) of the PANSS (mean=2.96, SD=1.45, P6=1-2 (n=9), P6=3 (n=8), P6=4-6 (n=9)); higher scores indicated increased perceived persecution and suspicious hypervigilance. Complete PANSS scores were available for 23 of 26 subjects (PANSS total mean=51.17, SD=17.40; PANSS positive subscale mean=12.17, SD=4.92; PANSS negative subscale mean=13.91, SD=5.28; PANSS general subscale mean=25.09, SD=9.54).

fMRI Paradigm

The scanning session included a "fear" condition, about which participants were told before the scanning session "an electrodermal stimulation can occur at any time" in conjunction with a specified colored square, and a "safety" condition for which participants were verbally instructed before the scanning session that they would not receive any electrodermal stimulations associated with a distinct colored square. Fear and safety conditions were signified by the presentation of easily-distinguishable blue or yellow colored squares via an MR-compatible screen.

Pairing of colors with conditions was counterbalanced across participants. Each color appeared for 12 s followed by 18 s of rest (30-s condition period). There were five pseudo-randomly ordered periods of each color per scanning run (each run was preceded by a 20-s rest period), and two scanning runs per study session. No motor response was required. Participants did not actually receive any electrodermal stimulation during scanning.

In a second fMRI paradigm, participants read 48 printed words, 24 of which were selected for their threatening content and negative valence so as to be particularly relevant to individuals with paranoid delusions (e.g., "persecute," "threat," "spy"). The remaining 24 words were selected for their emotionally neutral content (e.g., "arrange," "rotate," "folder"). The two word categories were counterbalanced for the possible confounding variables of word length, frequency within the lexicon and part of speech. Subjects were instructed to read each word silently and then to immediately press a button under their right index finger. The stimuli were presented in a block design that included four blocks of six threat (T) words each and four blocks of six neutral (N) words each. The blocks were intermixed in a pseudorandom order (NTTNNTNT). Each word appeared for 2 s with an interstimulus interval jittered based on a uniform distribution on the range [1.8, 3.8] (average of 2.8 s), for a total of 28.8 s per block. Each block was followed by 24 s of rest, with the paradigm as a whole preceded and followed by two 12-s rest periods. During rest periods, subjects were instructed to look at a dash at the center of the screen.

Immediately after imaging was completed, subjects were removed from the scanner and their memory for the specific stimuli seen in the scanner was tested with a list consisting of the 48 stimuli seen during scanning (targets) and 24 novel words (distractors) with which the targets were interspersed. Distractors were divided equally into threat and neutral words and balanced for the same qualities as the target words. The subjects were instructed to read each word and to indicate those words that they believed they had seen in the scanner. Following this task, subjects rated the emotional valence of each word on a seven-point Likert scale (−3=strongly negative, 0=neutral, +3=strongly positive). The order of the instructed-fear/safety and emotional word paradigms was counterbalanced across subjects.

Image Acquisition

Following a standard T1-weighted localizer scan, a high-resolution T1-weighted anatomical image data were acquired using a spoiled gradient recalled acquisition sequence. Echo planar imaging (EPI) was used to obtain BOLD functional MR images. After shimming to maximize homogeneity, a series of gradient echo fMRI scans were acquired with a z-shimming algorithm to reduce susceptibility artifacts at the base of the brain. A reference T1-weighted anatomical image with the same slice placement and thickness was acquired immediately before the EPI acquisition.

Image Processing and Data Analysis

Data processing generally included the following: reconstruction of functional EPI images; manual anterior commissure-posterior commissure re-orientation of all anatomical and EPI images; realignment to correct for slight head movement between scans based on intracranial voxels (data sets with head movement of greater than ⅓ voxel over the study session were excluded); extraction of physiological fluctuations, such as cardiac and respiratory cycles from EPI image sequences; co-registration of functional EPI images to the corresponding high-resolution anatomical images based on the rigid body transformation parameters of the reference anatomical image to the latter for each individual subject; stereotactic normalization to a standardized coordinate space (e.g., MNI space) based on the high-resolution anatomical image to normalize for individual differences in brain morphology; and spatial smoothing with an isotropic Gaussian kernel (full width at half-maximum=7.5 mm) to increase signal-to-noise ratio.

For image data analyses, a two-level voxel-wise linear fixed-effects model was constructed using customized software in an ANCOVA setting. First, at the individual subject level, a whole-brain voxel-wise multiple linear regression model was employed. This was composed of the regressor of interest, which included the stimulus onset times convolved with a prototypical hemodynamic response function, and the covariates of no-interest, which included the temporal first order derivative of the principal regressors (to compensate for slight latency differences in individual hemodynamic response from the prototypical response function), global fluctuations, physiological fluctuations, realignment parameters, and scanning periods. Temporal filtering was performed to counter the effects of baseline shifts and higher frequency noise, and a first order autoregressive model of the time course was used to accommodate temporal correlation in consecutive scans.

Effects at every brain voxel were estimated using an expectation maximization algorithm, and regionally specific effects were then compared using linear contrasts. That is, for each subject, the effect image and its standard error image for each condition were calculated, and these were also combined in a series of linear contrasts entered into the second stage group-level correlation analysis. At the group level, the within-group effects of the hypothesis-driven contrasts were examined for their association with the P6 item score via a multiple regression model, with the P6 score as the main regressor, and age, sex, and mean daily dose equivalent of chlorpromazine as covariates of no-interest.

For the instructed-fear/safety data, only planned contrasts were examined: (1) instructed-fear vs. safety; (2) instructed-fear vs. baseline; and (3) instructed-safety vs. baseline. For the emotional word data, only planned contrasts were examined: (A) threat vs. neutral words; (B) threat words vs. baseline; and (C) neutral words vs. baseline. These group-level correlation effect estimates generated statistical maps of the t-statistic, and the statistical significance of the t-maps was then evaluated in the final step of inference. The statistical inference is based on random field theory, where the t-statistical maps were thresholded initially at a voxel-wise two-tailed p-value less than 0.01 (based on which cluster sizes of activated/deactivated areas were reported), and the group-level correlation effect of interest at a peak coordinate was considered significant if the corrected p-value less than 0.05, which was based on family-wise error rate correction of the voxel-wise p-values over the entire brain. Peak coordinates and sub-maxima were specifically reviewed for inclusion of the left human color area (V4) (x: −20 to −38; y: −70 to −90; z: −8 to −15; MNI coordinates) in the instructed-fear/safety contrasts and at the visual word form area (VWFA) (x: −42±5; y: −58±8; z: −17±6; MNI coordinates) in the emotional word contrasts.

Post-scan behavioral test data recognition rates and valence ratings were analyzed using repeated-measures ANCOVA. Recognition memory performance was assessed by calculating a discrimination index d' per word valence type for each individual based on signal detection theory, estimated by the z-score of the false alarm rate minus the z-score of the hit rate. Also, for the behavioral data analysis, subjects were stratified into three subgroups of non-paranoid (P6 score: 1-2), mildly paranoid (P6 score: 3), and paranoid (P6 score: 4-6) for statistical testing of persecutory delusion severity as a group factor. Age, sex and mean daily dose equivalence of chlorpromazine were entered as covariates of no-interest.

Results: Instructed-Fear/Safety Paradigm

Analyses were performed on 22 subjects (18 male, 4 female; mean age=28.13, range 20-43; mean P6 score=2.78, SD=1.48, P6=1-2 (9), P6=3 (7), P6=4-6 (6) to assess the correlation between P6 scores and BOLD activations during (1) instructed-fear vs. safety; (2) instructed-fear vs. baseline; and (3) instructed-safety vs. baseline.

FIGS. 13A-13C illustrate lateral orbitofrontal cortex and V4 color area activations correlated to persecutory delusion severity in the instructed-fear/safety paradigm. Neural activations correlated with persecutory delusion severity (P6 score) were studied in patients with schizophrenia using an instructed-fear/safety paradigm. Fear and safety cues were distinguished by delivery of different colored squares. Statistical parametric maps show blood-oxygen-level-dependent (BOLD) neural activation changes thresholded at a voxelwise p-value of 0.001 for visualization purposes. In the scatter plots, light blue indicates schizophrenia subjects, dark blue schizoaffective subjects.

FIG. 13A shows that positive correlation was observed between P6 scores and left and right lateral orbitofrontal cortex (OFC) in the instructed-fear vs. safety contrast. FIG. 13B shows that negative correlation was observed between P6 scores and left and right lateral OFC activations in the instructed-safety vs. baseline contrast. FIG. 13C shows that left V4 color area activation correlated with P6 scores in the instructed-fear vs. safety contrast, while reduced V4 color area activation correlated with P6 scores in the instructed-safety vs. baseline contrast.

FIGS. 14A-14D illustrate salience network activations correlated to persecutory delusion severity in the instructed-fear/safety paradigm. Statistical parametric maps show blood-oxygen-level-dependent (BOLD) neural activation changes thresholded at a voxelwise p-value of 0.001 for visualization purposes. In the scatter plots, light blue indicates schizophrenia subjects, dark blue schizoaffective subjects.

Figures 14A, 14B, 14C, 14D:
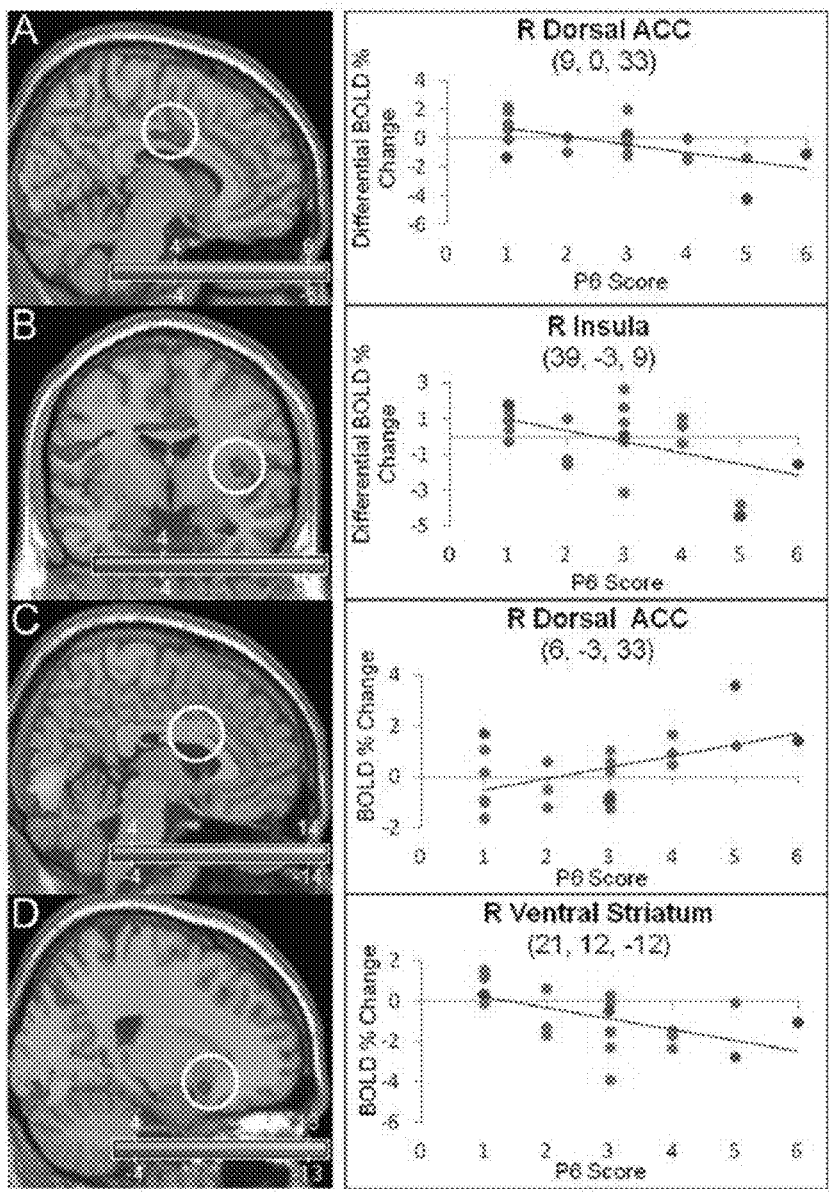
FIGS. 14A-14D illustrate salience network activations correlated to persecutory delusion severity in the instructed-fear/safety paradigm.

FIGS. 14A and 14B show that in the instructed-fear vs. safety contrast, decreased activations in the right posterior-dorsal anterior cingulate cortex (ACC) and insula correlated with P6 scores (persecutory delusion severity). FIGS. 14C and 14D show that in the instructed-safety vs. baseline contrast, P6 scores correlated positively with increased activations in the right posterior-dorsal ACC and insula, and correlated negatively with decreased right ventral striatum activations.

With the contrast instructed-fear vs. safety, P6 scores correlated positively with activations in visual processing areas (bilateral calcarine cortices, lingual gyri (including left V4 color area), left fusiform gyrus), bilateral lateral OFC/inferior frontal gyri, and left frontopolar cortex. P6 scores correlated negatively with activations in paralimbic areas (bilateral posterior-dorsal ACC, right insula) and default mode network (DMN) regions (right precuneus, supramarginal, angular gyri).

For instructed-fear vs. baseline, P6 scores correlated positively with activations in visual processing regions (bilateral calcarine, lingual and fusiform cortices), lateral OFC/inferior frontal gyri, and right anterior hippocampus. P6 scores correlated negatively with activations in paralimbic regions (right posterior-dorsal ACC, middle insula, left rostral ACC), visual processing regions (bilateral middle/inferior occipital, left lingual, right cuneus gyri), and DMN regions (right posterior cingulate cortex/precuneus, left angular gyrus).

For instructed-safety vs. baseline, P6 scores correlated positively with activations in visual processing regions (bilateral calcarine, fusiform, superior occipital cortices, right middle occipital, lingual gyri) and paralimbic areas (bilateral dorsal ACC, anterior insula). P6 scores correlated negatively with activations in visual processing regions (bilateral calcarine, lingual (including left V4 color area), inferior occipital gyri, right cuneus, left middle occipital, fusiform gyri) and limbic/paralimbic areas (bilateral lateral OFC/inferior frontal gyrus, right ventral striatum).

Results: Emotional Word Paradigm

Analyses were performed on 23 subjects (19 male, 4 female; mean age=30.22, range 20-44; mean P6 score=3.05, SD=1.42, P6=1-2 (n=7), P6=3 (n=7), P6=4-6 (n=9) to assess the correlation between P6 scores and BOLD activations during (1) threat words vs. neutral words; (2) threat words vs. baseline; and (3) neutral words vs. baseline.

FIGS. 15A-15D illustrate anterior language network and visual word form area activations correlated to persecutory delusion severity in the emotional word paradigm. Statistical parametric maps show blood-oxygen-level-dependent (BOLD) neural activation changes thresholded at a voxelwise p-value of 0.001 for visualization purposes. In the scatter plots, light blue indicates schizophrenia subjects, dark blue schizoaffective subjects.

Figures 15A, 15B, 15C, 15D:
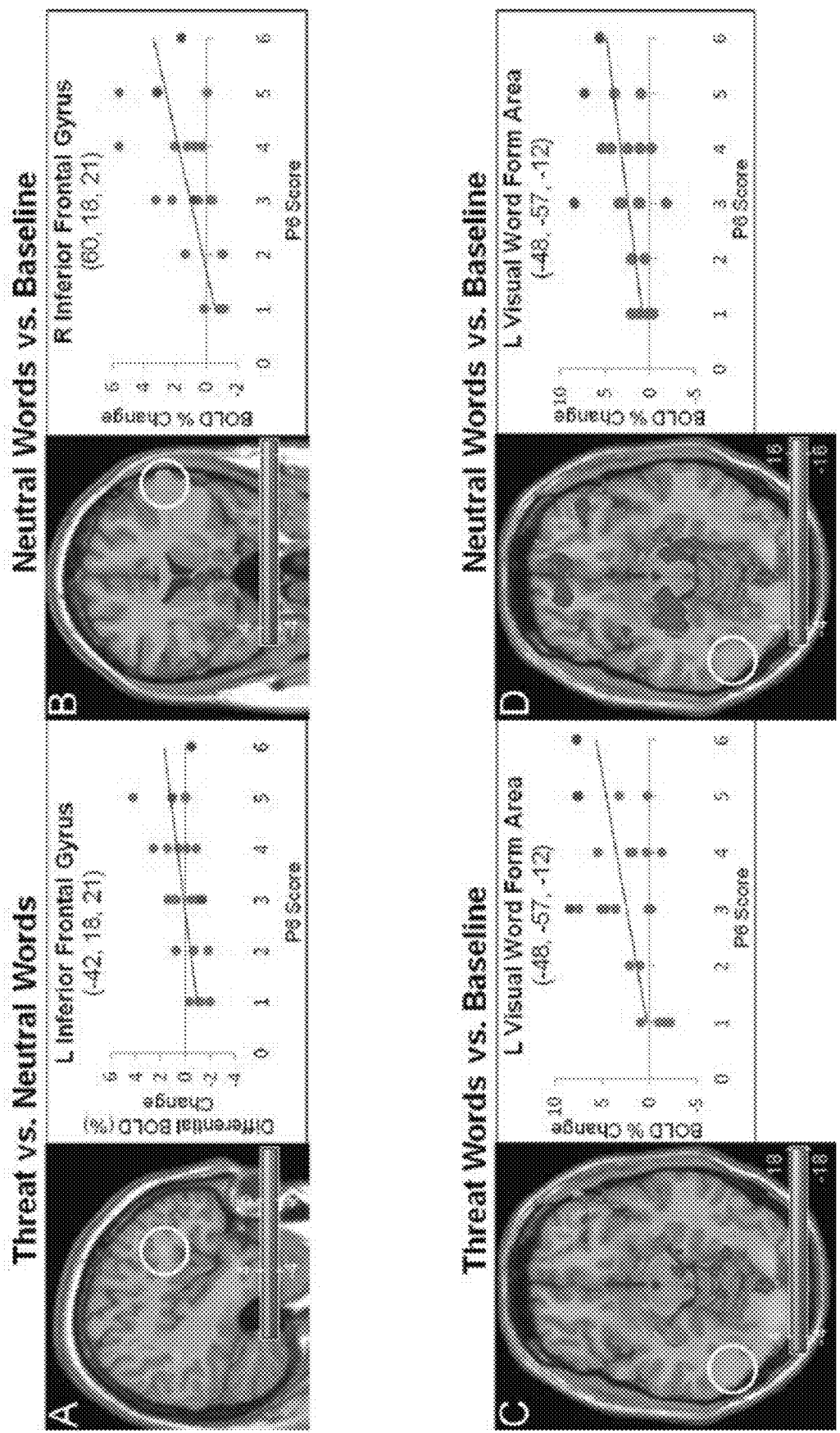
FIGS. 15A-15D illustrate anterior language network and visual word form area activations correlated to persecutory delusion severity in the emotional word paradigm.

FIG. 15A shows that P6 scores (persecutory delusion severity) positively correlated with left inferior frontal gyrus, pars opercularis/triangularis activations in the threat word vs. neutral word contrast. FIG. 15B shows that P6 scores correlated positively with right and left inferior frontal gyri for the neutral word vs. baseline contrast. FIGS. 15C and 15D show that visual word form area activations positively correlated with P6 scores in both the threat word and neutral word vs. baseline contrasts.

FIGS. 16A-16D illustrate frontolimbic activations correlated to persecutory delusion severity in the threat word versus neutral word contrast. The statistical parametric maps show blood-oxygen-level-dependent (BOLD) neural activation changes thresholded at a voxelwise p-value of 0.001 for visualization purposes. In the scatter plots, light blue indicates schizophrenia subjects, dark blue schizoaffective subjects.

Positive correlations can be seen between P6 scores and (FIG. 16A) right ventromedial prefrontal cortex (vmPFC), (FIG. 16B) left parahippocampus, (FIG. 16C) left hippocampus, and (FIG. 16D) left amygdala.

With the contrast threat vs. neutral words, P6 scores correlated positively with activations in semantic processing regions (left lateralized inferior frontal, superior temporal gyri), limbic/paralimbic areas (bilateral vmPFC, left insula, parahippocampus, hippocampus, amygdala (trend)), and bilateral frontopolar cortices. P6 scores correlated negatively with activations in visual processing regions (left calcarine, cuneus), semantic processing regions (bilateral superior/middle temporal gyri, right inferior frontal gyrus), and the right inferior parietal lobule (an-gular/supramarginal gyri).

For threat words vs. baseline, P6 scores correlated positively with activations in visual ventral stream areas (bilateral middle occipital, cuneus, inferior temporal and fusiform gyri (VWFA), left calcarine, superior/middle occipital, right lingual gyri), semantic processing regions (left 4 right inferior frontal gyrus, bilateral superior/middle temporal gyri, opercular rolandic), and limbic/paralimbic areas (bilateral anterior-dorsal ACC, OFC, parahippocampal gyri, insula, left amygdala (trend)). P6 scores correlated negatively with activations in visual processing areas (bilateral calcarine, cuneus, right lingual and fusiform gyri), paralimbic regions (right rostral ACC, subgenual ACC, and OFC), DMN regions (bilateral angular gyri, precuneus, right temporoparietal junction/supramarginal and left posterior cingulate cortex), and bilateral frontopolar cortex.

For neutral words versus baseline, P6 scores correlated positively with activations in ventral visual stream processing areas (bilateral calcarine, superior occipital cortices, lingual, middle occipital, inferior temporal, fusiform gyri (VWFA), left inferior occipital gyrus), semantic processing regions (bilateral inferior frontal, superior/middle temporal gyri, left opercular rolandic), and paralimbic regions (bilateral anterior insula, right anterior-dorsal ACC, left mid-OFC). P6 scores correlated negatively with activations in visual processing areas (bilateral calcarine cortices, left cuneus, middle occipital, fusiform gyri, right inferior occipital and lingual gyri), limbic/paralimbic regions (bilateral posterior-medial OFC, vmPFC, parahippocampus, and left hippocampus), semantic processing regions (bilateral inferior frontal gyri, left middle temporal), bilateral frontopolar cortices, precuneus and left angular gyrus.

Summary

As seen in FIGS. 13A-13C, FIGS. 14A-14D, FIGS. 15A-15D, and FIGS. 16A-16D, the example study described above illustrated that patterns of neuronal activity can be used as a biomarker for aiding in the diagnosis of schizophrenia. Using the methods described above, these patterns of neuronal activity can be implemented in a multivariate classifier to identify individuals as belonging to a population consistent with the neural signatures associated with schizophrenia. To this end, the methods described here can be utilized to provide diagnostic information about whether an individual patient is likely to have schizophrenia.

Example 3: Biomarker for Diagnosing Post Traumatic Stress Disorder

In this example, participants included 8 subjects meeting DSM-IV criteria for panic disorder ("PD") (mean age=37 years, range=24-50); 8 subjects meeting DSMIV criteria for post traumatic stress disorder ("PTSD") (mean age=42 years, range=37-50); and 8 healthy comparison subjects (mean age=35 years, range=24-49). PTSD and comparison subjects were a matched subset of larger groups. Each group includes 4 female and 4 male right-handed subjects. Among the patients, there were current secondary diagnoses of generalized anxiety disorder, social phobia, specific phobia, major depressive disorder, dysthymia, and personality disorders. Otherwise, all participants were free of other psychiatric diagnoses, substance abuse, and significant neurological or medical disorders. No subjects were on psychiatric medication, except one PD subject (sertraline, bupropion).

fMRI Paradigm

Prior to scanning, subjects determined the level of electrodermal stimulation to be received during the scan via a standardized dialup procedure to a level of intensity experienced as "uncomfortable but not painful" to standardize subjective stimulus aversiveness across subjects. The scanning session consisted of a "Threat" condition, about which participants were told "an electrodermal stimulation can occur at any time", and a "Safe" condition during which participants were told they would receive no stimulations.

Threat and Safe were signified by the presentation of easily distinguishable colored squares via an MR-compatible screen. Pairing of colors with conditions was counterbalanced across participants. Each color appeared for a period of 12 s followed by a 18 s rest period. There were five pseudo-randomly ordered blocks of each color per scanning run, and two scanning runs (first run=early run; second run=late run) per study session. Participants did not receive any electrodermal stimulation during scanning.

Image Acquisition

Gradient echo echo-planar functional images sensitive to blood oxygen level-dependent (BOLD) signal were obtained. Images were acquired using a modified z-shimming algorithm to minimize susceptibility artifacts at the base of the brain. An identically sliced reference T1 weighted anatomical image was acquired to aid re-orientation and coregistration. A high-resolution T1 weighted anatomical image was acquired using a spoiled gradient recalled acquisition sequence.

Image Processing and Data Analysis

Data processing included manual AC-PC re-orientation of all anatomical and EPI images; realignment of EPI images to correct for slight head movement between scans and for differential spin excitation history based on intracranial voxels; extraction of physiological fluctuations such as cardiac and respiratory cycles from the EPI image sequence co-registration of functional EPI images to the corresponding high-resolution anatomical image based on the rigid body transformation parameters of the reference anatomical image to the latter for each individual subject; stereotactic normalization to a standardized coordinate space (Montreal MRI Atlas version of Talairach space) based on the high-resolution anatomical image; and spatial smoothing with an isotropic Gaussian kernel (FWHM=7.5 mm).

A two-stage voxel-wise linear mixed-effects model was utilized to examine the key Group/Condition contrasts of interest. First, a whole-brain voxel-wise multiple linear regression model was employed at the individual subject level which comprised the regressor of interest, the covariates of no interest (the first-order temporal derivative of the regressor of interest, global and physiological fluctuations, realignment parameters, scanning period means, and baseline drift up to the third order polynomials) and an AR(1) model of the residual time series to accommodate temporal correlation in consecutive scans.

Second, at the group level, a mixed-effects model was used, which accounts for intrasubject and intersubject variability, and allows for population-based inferences to be drawn. Age and gender were used as covariates of no interest in an analysis of covariance setting.

A voxel-wise inference at the group level was then drawn according to Gaussian random field theory. Initial uncorrected threshold was $p<0.001$; comparisons were considered significant at $p<0.05$ in either whole brain correction or in small volume correction in a priori regions of interest (amygdala, basal ganglia and vmPFC) selected based on previous results. BOLD activity t-maps are shown at voxel-wise p-values less than 0.01 for the purpose of presentation only.

Results

During debriefing all subjects indicated that they had expected to receive an electrodermal stimulation during the presentation of the Threat stimulus and that this expectation was associated with the feeling of fear which decreased with repeated presentations over time.

In healthy control subjects, significant activation was exhibited in the contrast of Threat versus Safety in bilateral anterior insula, bilateral basal ganglia and thalamus, bilateral dorsal anterior cingulate and bilateral dorsolateral prefrontal cortex. In the contrast of Safe versus Threat, increased activation was found in bilateral primary motor cortex, bilateral hippocampi/parahippocampi, bilateral posterior cingulate/precuneus and angular gyri as well as in bilateral medial and lateral orbitofrontal cortex from a larger sample.

Figure 17A:
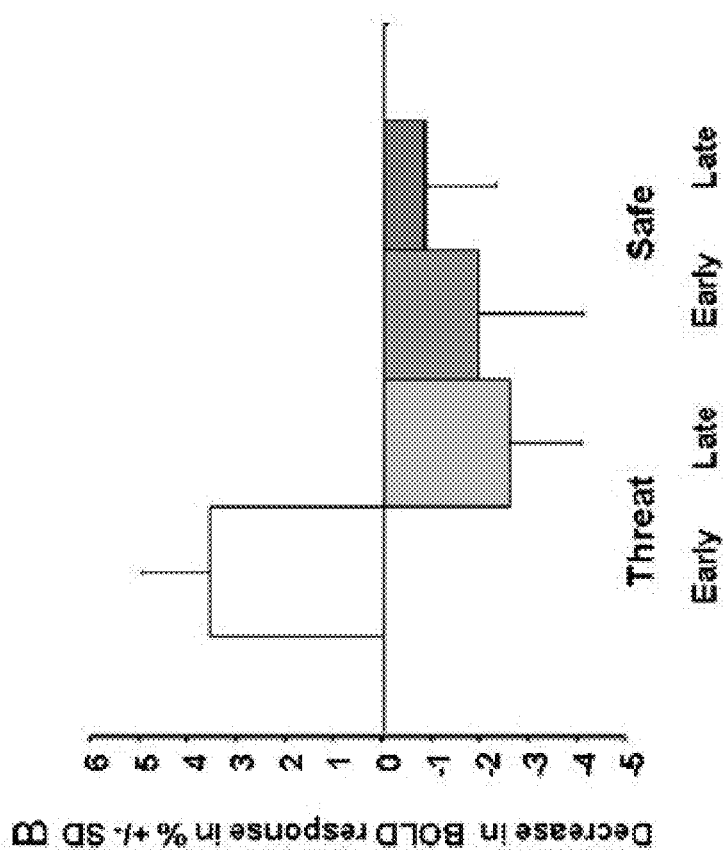
FIGS. 17A-17B illustrate increased amygdala activity and subgenual cingulate (Brodmann area 25) activity in early runs (parametric modeling of the Threat vs. Safe by Early vs. Late interaction) in Normal Control subjects (FIG. 17A), and a bar plot showing the BOLD response±SD (%) at the point showing maximum activity for the Threat vs. Safe by Early vs. Late interaction in the amygdala (FIG. 17B)
Figure 17B:
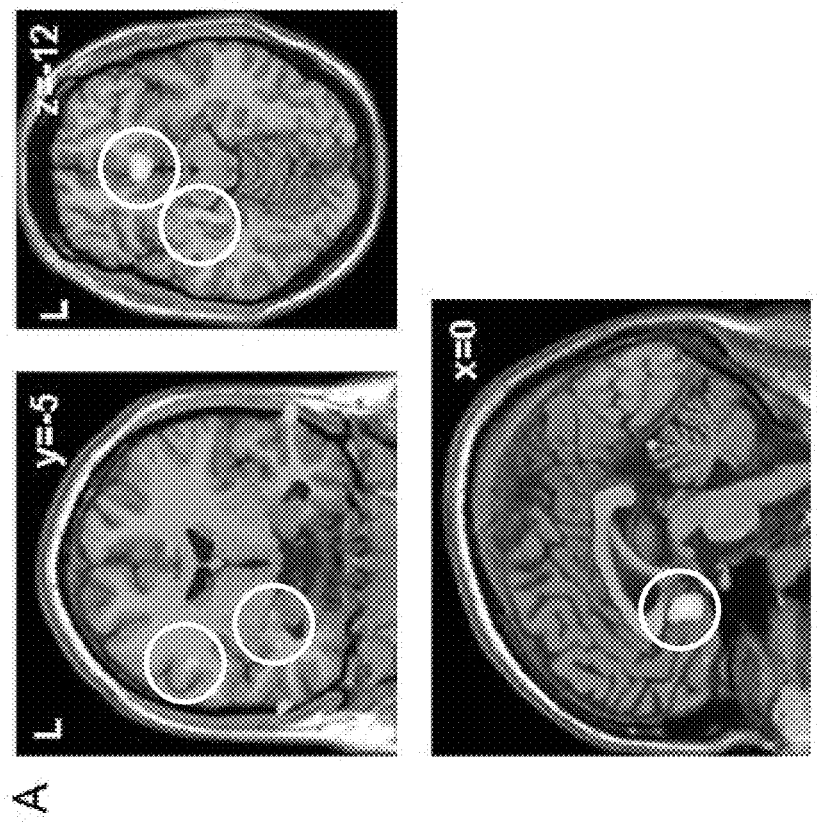

FIGS. 17A-17B illustrate coronal (y=−5), axial (z=−12), and sagittal (x=0) sections showing increased amygdala activity and subgenual cingulate (Brodmann area 25) activity in early runs (parametric modeling of the Threat vs. Safe by Early vs. Late interaction) in Normal Control subjects ($p<0.01$) (FIG. 17A), and a bar plot showing the BOLD response±SD (%) at the point showing maximum activity for the Threat vs. Safe by Early vs. Late interaction in the amygdala (MNI [−21, 0, −12]) (FIG. 17B). BOLD response is shown for Normal Controls, conditions [Threat, Safe], and study session [broken into Early and Late run] relative to a resting baseline.

Parametric modeling of trials over time revealed an initial decrease of amygdalar activation (FIG. 17A) which was mainly driven by the Threat condition (FIG. 17B) and accompanied by a co-variation in sgACC activity (FIG. 17A).

Figures 18A, 18B:
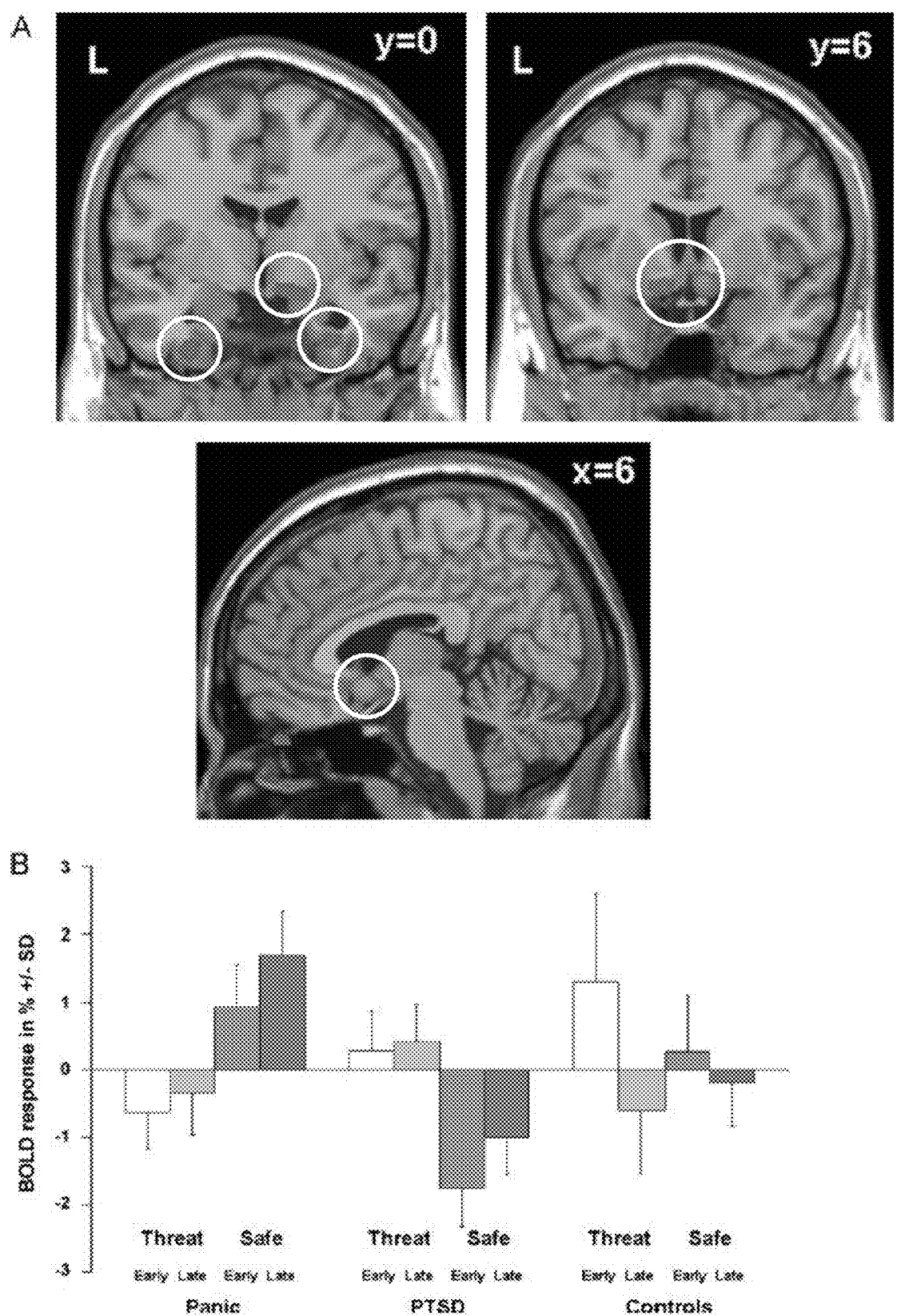
FIGS. 18A-18B illustrate decreased subgenual cingulate (Brodmann area 25), ventral striatum, and extended amygdala activity for the Threat vs. Safe condition in Panic vs. PTSD subjects (FIG. 18A), and a bar plot showing BOLD response±SD (%) at the point showing maximum activity for the Threat vs. Safe condition in Panic vs. PTSD subjects (FIG. 18B)

FIGS. 18A-18B illustrate coronal (y=0 and y=6) and sagittal (x=6) sections showing decreased subgenual cingulate (Brodmann area 25), ventral striatum, and extended amygdala activity for the Threat vs. Safe condition in Panic vs. PTSD subjects ($p<0.01$) (FIG. 18A). The bar plot shows BOLD response±SD (%) at the point showing maximum activity for the Threat vs. Safe condition in Panic vs. PTSD subjects [6, 12, −9] (FIG. 18B). This point is located in the subgenual anterior cingulate cortex. BOLD response is shown for groups [Panic, PTSD, Normal Controls], conditions [Threat, Safe], and study session [broken into Early and Late run] relative to a resting baseline.

The comparison of PD versus PTSD patients found less activation in the Threat versus Safe contrast in regions including the subgenual cingulate (Brodmann area 25), ventral striatum, and extended amygdala, with contrast maximum in the subgenual cingulate ([6, 12, −9], Z=−4.43, voxel-wise $p<0.0001$, $p<0.05$ [corrected]). These findings were due to an increase in activation to the Safe condition in PD patients, co-varying with an increased activity to the Threat condition in PTSD patients (FIG. 18B). When the study sessions were broken into Early (first run) and Late (second run) components, healthy control subjects activated this region most strongly in the Early Threat condition while PTSD subjects activate this region equivalently in the Early and Late Threat conditions (FIG. 18B).

Figures 19A, 19B:
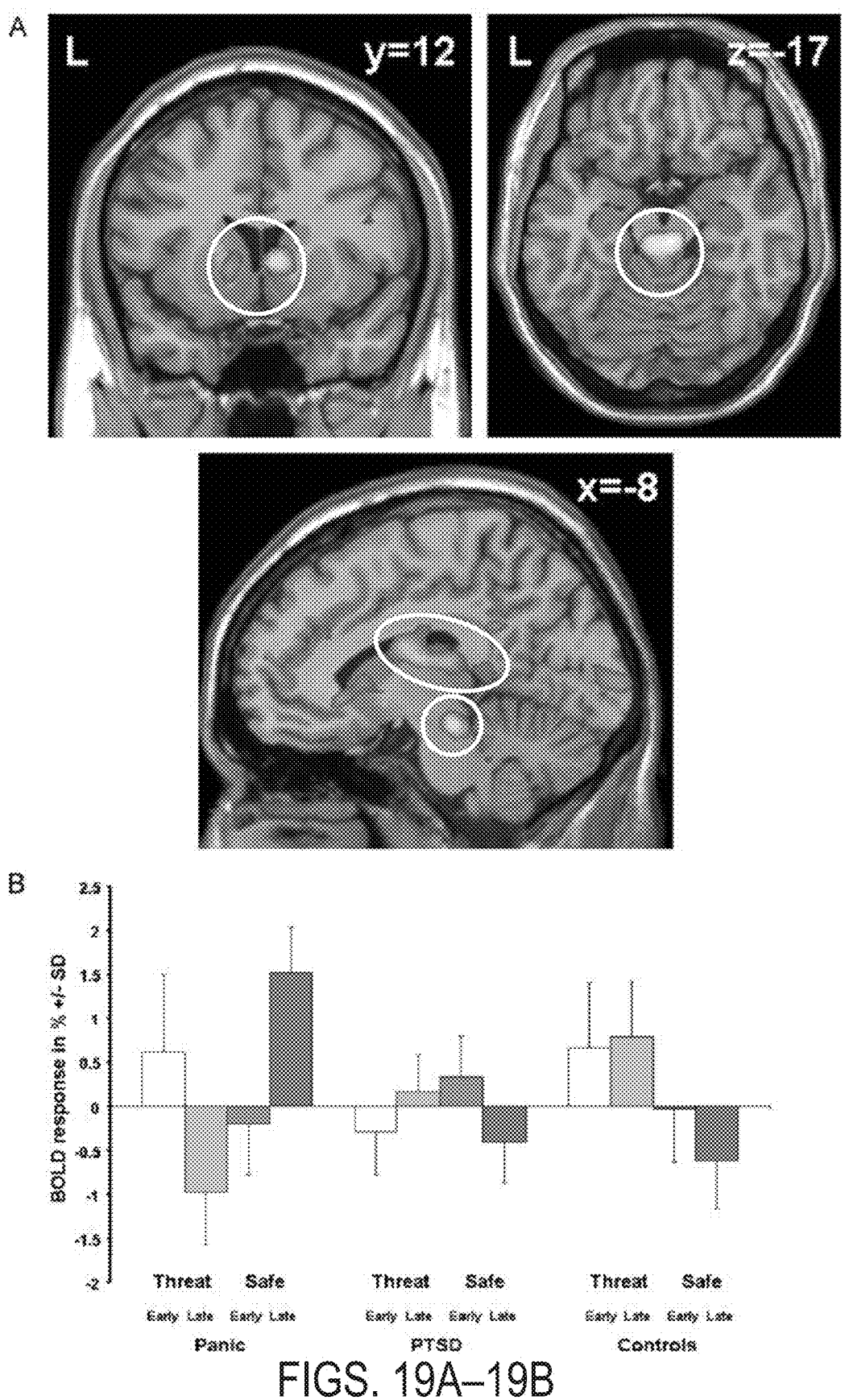
FIGS. 19A-19B illustrate increased dorsal midbrain/mesial periaquaeductal grey and (right) caudate for the Threat vs. Safe by Early vs. Late interaction in Panic vs. PTSD subjects (FIG. 19A), and a bar plot showing BOLD response±SD (%) at the point showing maximum activity for the Threat vs. Safe by Early vs. Late interaction in Panic vs. PTSD subjects MNI (FIG. 19B)

FIGS. 19A-19B illustrate coronal (y=12), axial (z=−17), and sagittal (x=−8) sections showing increased dorsal midbrain/mesial periaqueductal grey and (right) caudate for the Threat vs. Safe by Early vs. Late interaction in Panic vs. PTSD subjects ($p<0.01$) (FIG. 19A). The bar plot shows BOLD response±SD (%) at the point showing maximum activity for the Threat vs. Safe by Early vs. Late interaction in Panic vs. PTSD subjects MNI [6, −24, −18] (FIG. 19B). This point is located in the tegmental periaqueductal gray area. BOLD response is shown for groups [Panic, PTSD, Normal Controls], conditions [Threat, Safe], and study session [broken into Early and Late run] relative to a resting baseline.

The direct contrast of Early (first half) and Late (second half) components of the Threat versus Safe comparison revealed increased activity in PD versus PTSD patients, most prominently in the dorsal midbrain/mesial periaqueductal grey (MNI [6, −24, −18], Z=4.49, voxel-wise $p<0.0001$, $p<0.003$ [corrected]) (FIG. 19A) and right caudate (MNI [9, 12, 3], Z=3.72, voxel-wise $p<0.0001$, $p<0.045$ [corrected]) (FIG. 19A). Inspection of the BOLD responses in the dorsal midbrain/mesial periaquaedutal grey (MNI [6, −24, −18]) (FIG. 19B) revealed a time-by-condition interaction in PD patients with a marked response to the late Safe condition.

Summary

As seen in FIGS. 17A-17B, FIGS. 18A-18B, and FIGS. 19A-19B, the example study described above illustrated that patterns of neuronal activity can be used as a biomarker for aiding in the diagnosis of panic disorder or PTSD. Using the methods described above, these patterns of neuronal activity can be implemented in a multivariate classifier to identify individuals as belonging to a population consistent with the neural signatures associated with panic disorder or PTSD. To this end, the methods described here can be utilized to provide diagnostic information about whether a patient is likely to have panic disorder or PTSD.

Example 4: Biomarker for Indicating Likelihood of Treatment Response for Borderline Personality Disorder In this study, 10 female subjects with BPD (9 right-handed; mean age=27.8 years, range=23-32 years) were studied. BPD diagnoses were confirmed with the International Personality Disorder Examination25 (criteria score range=5-9, dimensional score range=10-18; mean=15.00, SD=2.45). None of the participants had significant medical or neurological conditions. Five patients reported ongoing psychotropic medication use during the pre-treatment scan (five, antidepressants; two, mood stabilizers; four, anxiolytics; two, stimulants; one, opiate). Two patients were also taking oral contraceptives. Post-treatment, a distinct sub-set of five patients reported ongoing psychotropic medication use (three, antidepressants; three, mood stabilizers; one, stimulant; one, opiate), and no patients were taking oral contraceptives.

Following initial assessment and pre-treatment scanning, patients participated in Transference-Focused Psychotherapy ("TFP") (average number of sessions attended=76.60, SD=8.28). TFP consisted of twice weekly individual, 50-minute sessions. Rating of adherence and competence were made by the supervisors on the TFP Adherence and Competence Rating Scale. Interrater reliability between two raters was high (intraclass correlation coefficient (ICC)=0.96).

All participants received the Multidimensional Personality Questionnaire (MPQ), the Affective Lability Scale (ALS), and the Overt Aggression Scale-Modified (OAS-M)

prior to therapy initiation and at follow-up scanning. The MPQ was used to relate the clinically relevant factor of constraint to functional neuroimaging results. A high level of constraint reflects tendencies to inhibit and restrain impulse expression. The ALS is a 54-item self-report instrument where subjects rate the tendency of their mood to shift between normal to affectively charged domains of anger, depression, elation and anxiety, as well as their tendency to shift between depression and elation and between depression and anxiety. OAS-M is a clinician-rated scale that characterizes aggressive behavior within the past week based on observation and self-report.

fMRI Paradigm

Participants underwent pre-treatment and post-treatment scanning (average interval period between scans=12.1 months; range=10-14 months) while they performed an emotional linguistic go/no-go task developed to investigate neurocircuitry underlying the interaction between emotional processing and motor inhibition, with verbal stimuli containing themes salient for BPD, similar to the functional paradigm described above with respect to Example 1.

Image Acquisition

Imaging data were acquired pre- and post-TFP. For both pre- and post-TFP scanning sessions, structural images were acquired with a three-dimensional high-resolution T1-weighted spoiled gradient (SPGR) recalled acquisition sequence. Before fMRI runs, a reference T1-weighted anatomical image with the same axial slice placement and thickness as the functional imaging was acquired with two slices centered within the amygdala. Echo planar imaging (EPI) was used to obtain BOLD functional MR images. After shimming to maximize homogeneity, a series of functional scans were collected using a gradient echo EPI sequence with a z-shimming algorithm to reduce susceptibility artifacts in ventral brain regions of interest.

Image Processing and Data Analysis

A two-level voxel-wise linear random-effects model was utilized to examine the effect sizes of the key Group/Condition contrasts in a three-way repeated-measures ANCOVA setting. Based on a priori hypotheses derived from prior studies, as well as theoretical considerations, regions-of-Interest ("ROIs") were selected to contain the bilateral posterior-medial OFC, ACC, and amygdale. These ROIs were defined from previously reported fMRI studies concerned with impulse control and negative affect regulation.

Planned contrasts-of-interest ("COIs") of BOLD signal patterns probing motor inhibitory control during negative versus neutral emotional processing, specifically selected on the basis of previously determined task-related differential activations in BPD versus healthy subjects, were examined (1) as a function of treatment [(post-treatment scan vs. pre-treatment scan)×(negative vs. neutral)×(nogo vs. go)], and (2) as predictors of treatment response [pretreatment scan: (negative vs. neutral)×(nogo vs. go)] via correlations with TFP-related changes in MPQ-constraint, ALS-total and OAS-M. The statistical significance of the group-level comparison/interaction was assessed based on Gaussian Random Field Theory. The group-level t-statistic map of a COI was initially thresholded at a voxel-wise p-value less than 0.01 and a spatial extent greater than 0.25 cc.

For a ROI, the predicted peaks were considered statistically significant if their initial voxel-wise p-value was less than 0.001 and family-wise-error-rate (FWE) corrected p-value was less than 0.05 over a sphere with a radius=6.2 mm which resulted in a search volume of one cc.

Results

The principal contrast of interest relevant to probing the neural substrates of the interaction of negative (versus neutral) emotional processing and behavioral inhibition as a function of longitudinal TFP treatment was identified as the three-way interaction term: [(post-treatment scan vs. pre-treatment scan)×(negative vs. neutral)×(no-go vs. go)]. In comparison to pre-treatment scans, BPD patients showed relative increased activations in cognitive control regions including right anterior-dorsal ACC, dlPFC, and FPC. Relative activation decreases were found in left ventrolateral PFC (vlPFC) [inferior frontal gyrus (pars orbitalis and triangularis)] and hippocampus.

FIGS. 20A-20D illustrate the three-way interaction between negative (versus neutral) emotional words and no-go (versus Go) conditions [(post-treatment scan vs. pre-treatment scan)×(negative vs. neutral)×(no-go vs. go)]. The statistical parametric maps characterizing BOLD neural activation changes are thresholded at a voxelwise p-value of 0.01 for the purpose of visualization. Following treatment with TFP, patients with borderline personality disorder demonstrated relative increased activations in the (FIG. 20A) right anterior-dorsal anterior cingulate cortex (peak z-score=3.19, voxel-wise p-value=0.001; corrected p-value=0.022) and the (FIG. 20B) right dorsolateral prefrontal cortex (peak z-score=3.12, voxel-wise p-value=0.001); relative activation decreases following treatment were noted in the (FIG. 20C) left inferior frontal gyrus (peak z-score=−3.57, voxel-wise p-value<0.001) and the (FIG. 20D) left hippocampus (peak z-score=−3.10, voxel-wise p-value=0.001).

Correlational analyses were employed to assess the association between clinical improvement in domains of interest following treatment and changes in neural activity during behavioral inhibition in the context of negative versus neutral emotional processing. With the three-way interaction contrast [(post-treatment scan vs. pre-treatment scan)× (negative vs. neutral)×(no-go vs. go)], improvements in MPQ-constraint scores correlated positively with left anterior-dorsal ACC activation. Improvements in ALS-total correlated positively with activation in left posterior-medial OFC/ventral striatum, and negatively with right amygdala/parahippocampal cortex activations.

Figures 21A, 21B, 21C, 21D:
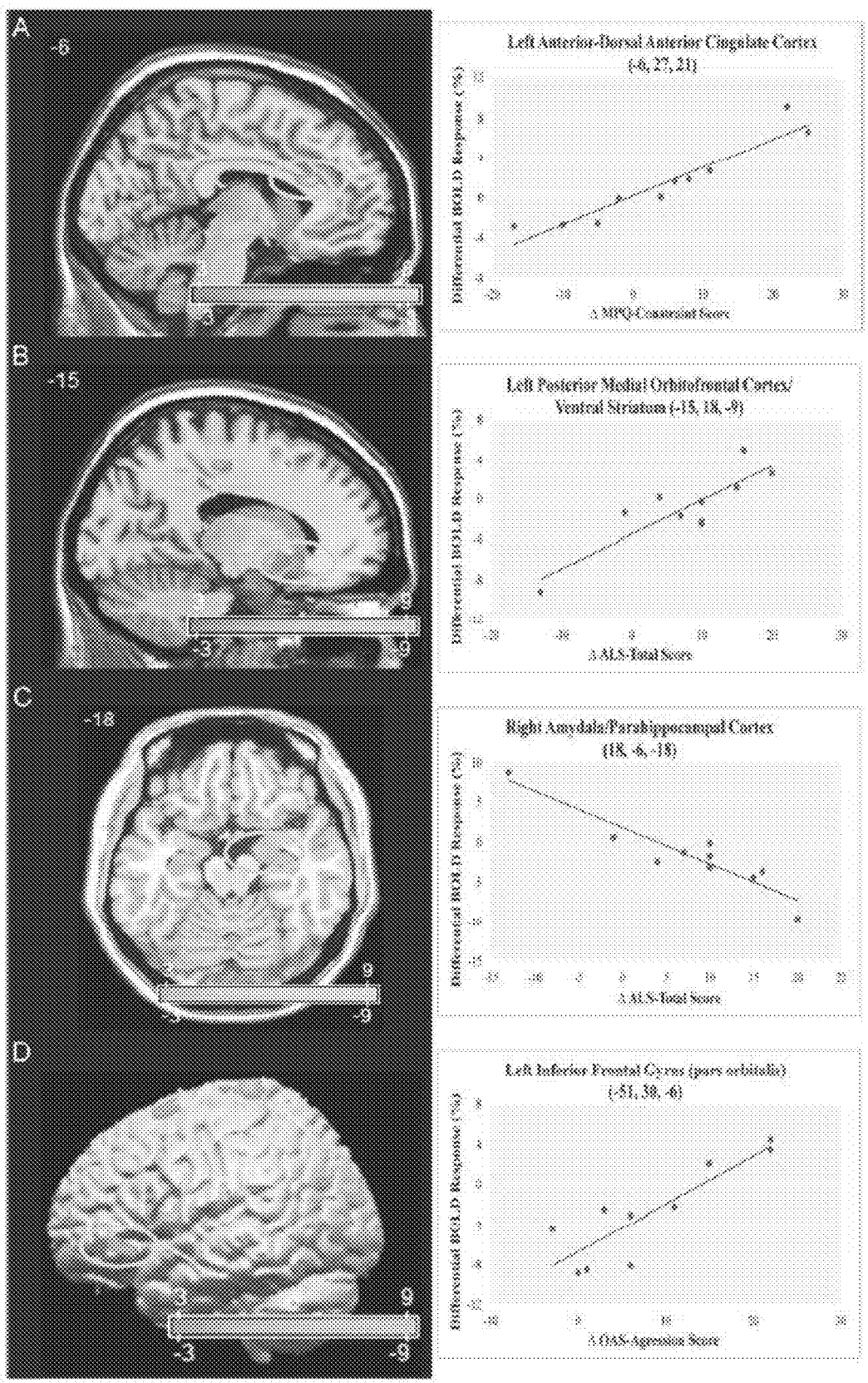
FIGS. 21A-21D illustrate correlational analyses of post vs. pre-treatment related effects on constraint, affective lability, and aggression for the three-way interaction between negative (versus neutral) emotional words and no-go (versus go) conditions [(post-treatment scan vs. pre-treatment scan)×(negative vs. neutral)×(no-go vs. go)]

FIGS. 21A-21D illustrate correlational analyses of post vs. pre-treatment related effects on constraint, affective lability, and aggression for the three-way interaction between negative (versus neutral) emotional words and no-go (versus go) conditions [(post-treatment scan vs. pre-treatment scan)×(negative vs. neutral)×(no-go vs. go)]. The statistical parametric maps characterizing BOLD neural activation changes are thresholded at a voxelwise p-value of 0.01 for the purpose of visualization. FIG. 21A shows a positive correlation between improvements in MPQ-Constraint score and relative increased activation in the left anterior-dorsal anterior cingulate cortex (peak z-score=4.14, voxel-wise p-value<0.001, corrected p-value=0.002). FIG. 21B shows a positive correlation between improvements in ALS-Total score and relative increased activation in the left posterior-medial orbitofrontal cortex/ventral striatum (peak z-score=3.14, voxel-wise p-value=0.001, corrected p-value=0.028). FIG. 21C shows a negative correlation between improvements in ALS-Total score and relative decreased activation in the right amygdala/parahippocampal cortex (peak z-score=3.87, voxel-wise p-value<0.001, corrected p-value=0.005). FIG. 21D shows a positive correlation between improvements in OAS-M aggression score and relative increased activation in the left inferior frontal gyrus (peak z-score=3.24, voxel-wise p-value=0.001). Note, the x-axes are formatted in FIGS. 21A-21D so that increasing values reflect clinical improvement in a given score.

Neural predictors of treatment response were examined by correlating pre-treatment neural activations to changes in clinical scores using the two-way contrast: [pre-treatment scan: (negative vs. neutral)×(no-go vs. go)]. Improvements in MPQ-constraint negatively correlated with pre-treatment right anterior-dorsal ACC activation. Improvement in ALS-total negatively correlated with left posterior-medial OFC/ventral striatum activation.

Figures 22A, 22B:
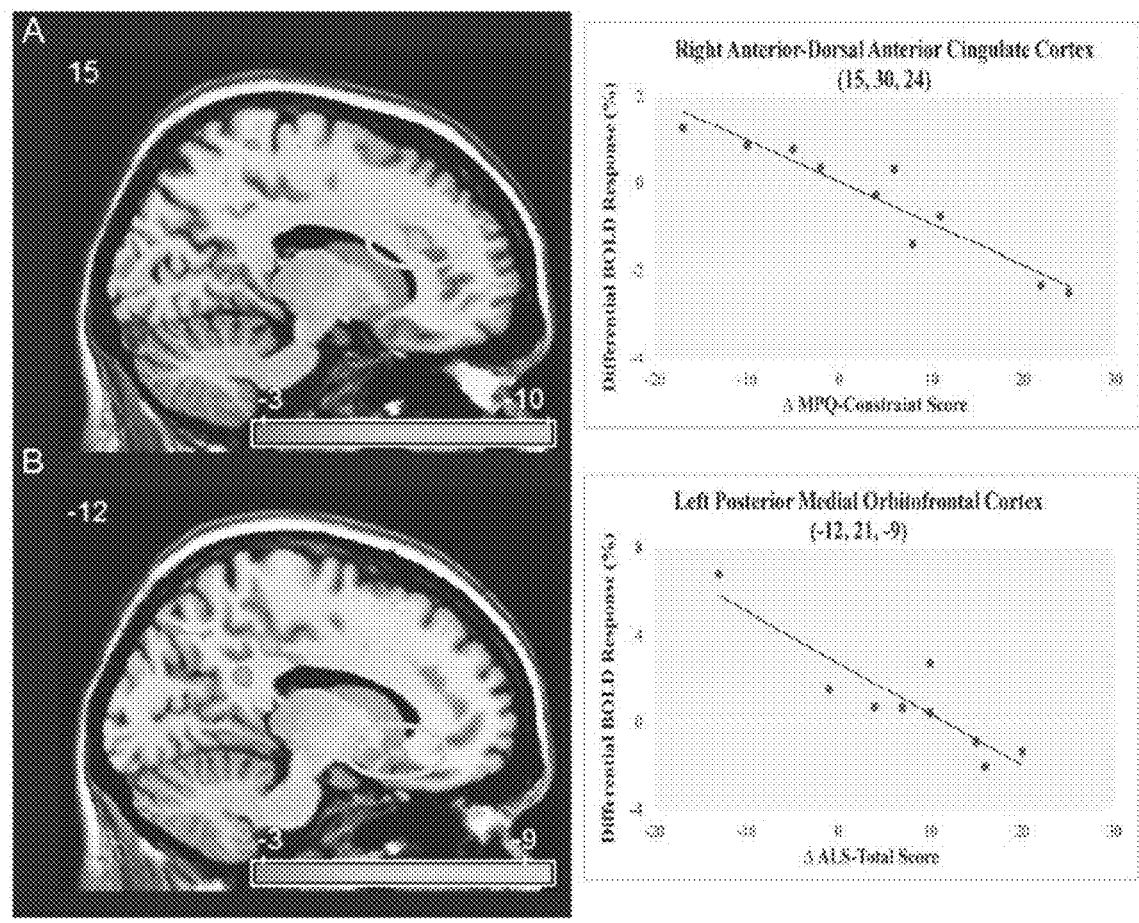
FIGS. 22A-22B illustrate correlational analyses of pre-treatment related effects on constraint and affective lability for the two-way interaction between negative (versus neutral) emotional words and no-go (versus go) conditions [pre-treatment scan: (negative vs. neutral)×(no-go vs. go)]

FIGS. 22A-22B illustrate correlational analyses of pre-treatment related effects on constraint and affective lability for the two-way interaction between negative (versus neutral) emotional words and no-go (versus go) conditions [pre-treatment scan: (negative vs. neutral)×(no-go vs. go)]. The statistical parametric maps characterizing BOLD neural activation changes are thresholded at a voxelwise p-value of 0.01 for the purpose of visualization. FIG. 22A shows an inverse correlation between pre-treatment activation in the right anterior-dorsal anterior cingulated cortex and post-treatment improvements in MPQ-Constraint score (peak z-score=−4.18, voxel-wise p-value<0.001, corrected p-value=0.002). FIG. 22B shows an inverse correlation between pre-treatment activation in the left posterior-medial orbitofrontal cortex/ventral striatum and post-treatment improvements in ALS-Total score (peak z-score=−3.47, voxel-wise p-value<0.001, corrected p-value=0.013). Note, the x-axes in FIGS. 22A and 22B are formatted so that increasing values reflect clinical improvement in a given score.

Summary

As seen in FIGS. 20A-20D, FIGS. 21A-21D, and FIGS. 22A-22B, the example study described above illustrated that patterns of neuronal activity can be used as a biomarker for indicating prognostic information related to treatment response in BPD. Using the methods described above, these patterns of neuronal activity can be implemented in a multivariate classifier to help classify individuals based on a predicted treatment response. To this end, the methods described here can be utilized to generate biomarkers that provide prognostic information about whether an individual patient is likely to have a particular treatment outcome.

Figure 23A:
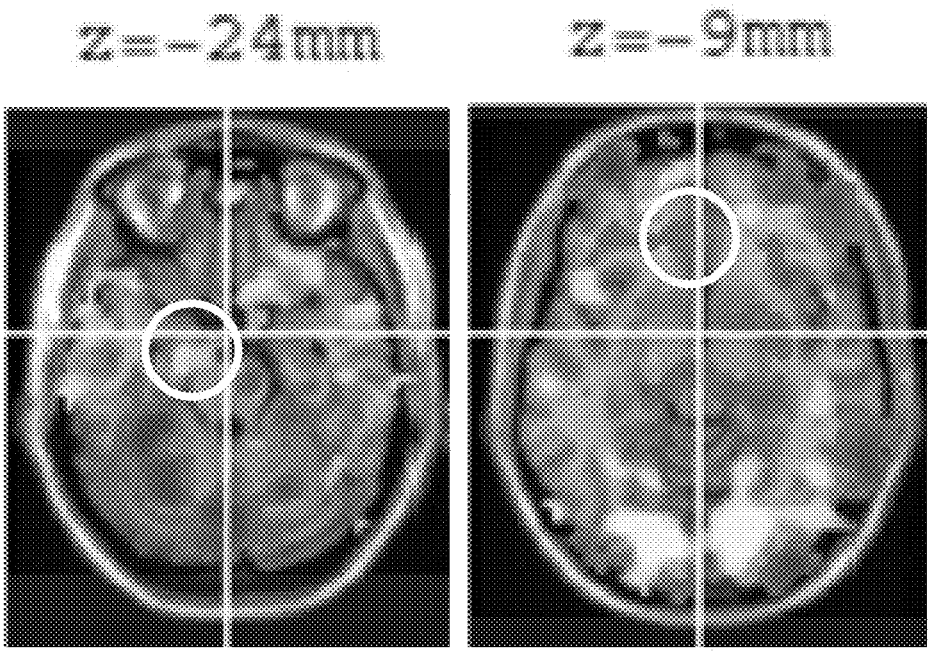
FIG. 23A illustrates patterns of neuronal activity in a pre-treatment profile for PTSD associated with subsequent treatment response as measured by the Clinician-Administered PTSD Scale (CAPS) in responders vs. non-responders.
Figure 23B:
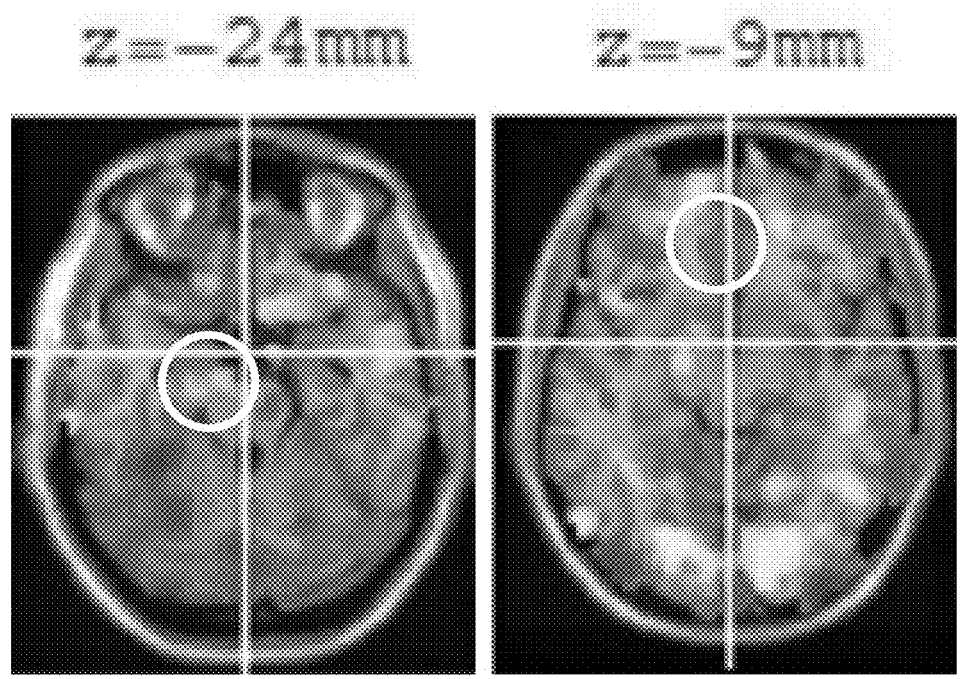
FIG. 23B illustrates patterns of neuronal activity in a pre-treatment profile for PTSD that correlates with diminution in symptom severity as measured by the CAPS.

Example 5: Biomarker for Indicating Likelihood of Treatment Response for Post Traumatic Stress Disorder As seen in FIGS. 23A and 23B, a pattern of neuronal activity including increased amygdalar and decreased ventromedial prefrontal activation in response to threat can be associated with PTSD. FIG. 23A illustrates a pre-treatment profile associated with subsequent treatment response as measured by the Clinician-Administered PTSD Scale (CAPS) in responders vs. non-responders, and FIG. 23B illustrates a pre-treatment profile that correlates with diminution in symptom severity as measured by the CAPS.

This example illustrates that patterns of neuronal activity can be used as a biomarker for aiding in the prognosis and treatment monitoring for PTSD. Using the methods described above, these patterns of neuronal activity can be implemented in a multivariate classifier to help classify individuals based on a predicted treatment response. To this end, the methods described here can be utilized to generate biomarkers that provide prognostic information about whether an individual patient is likely to have a particular treatment outcome.

Example 6: Biomarker for Evaluating Treatment Response in Borderline Personality Disorder As described in examples above, individuals with BPD, compared with healthy controls, displayed decreased activity in ventromedial prefrontal regions associated with inhibitory control and increased activity in extended amygdalar/ventral striatal regions associated with basic emotional processing in the context of a task involving behavioral inhibition in the setting of negative emotion. In addition, patients showed increased activity in prefrontal regions associated with more effortful control, possibly representing attempts to compensate for the deficit in lower level, automatic inhibitory function. The decreased prefrontal and increased peri-amygdalar activity seen in patients with BPD correlated highly, respectively, with clinical measures of decreased restraint and negative emotion. These findings represent a biomarker for treatment interventions.

Changes in brain activity in patients with BPD following treatment with transference-focused therapy, a treatment designed to decrease negative emotion and increase behavioral restraint, can be measured and analyzed to monitor treatment response. Preliminary analysis of data from the first few subjects reveals that those with the most marked improvement in symptoms following treatment demonstrated significantly increased medial prefrontal and decreased peri-amygdalar/limbic activity in the setting of a task involving behavioral inhibition in the setting of negative emotion, consistent with improved behavioral control and decreased negative emotionality; as well as significantly increased ventral striatal activity in tasks involving positive emotion, suggesting an enhanced appreciation of and response to positive stimuli.

Figure 24A:
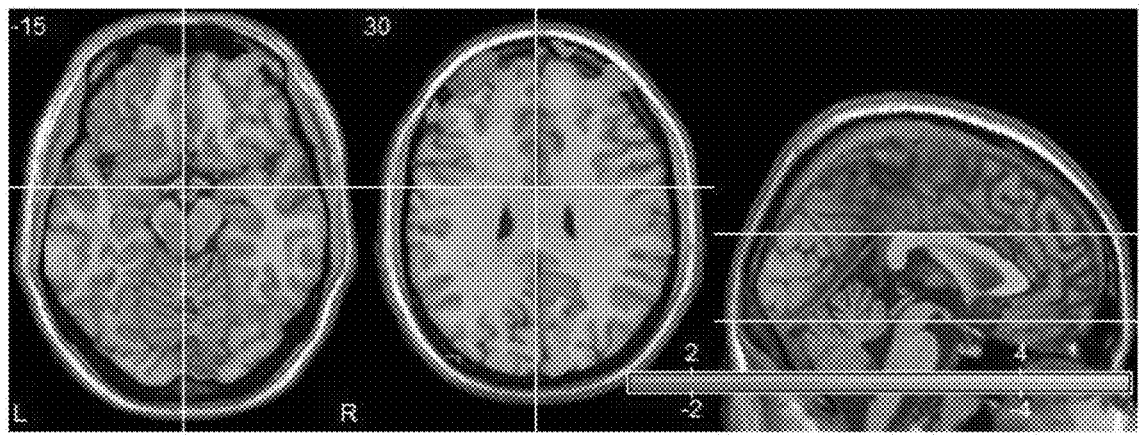
FIG. 24A illustrates patterns of neuronal activation following treatment of a patient with BPD, in which decreased limbic and increased medial prefrontal activation in the context of a task involving behavioral inhibition in the setting of negative emotion are shown.
Figure 24B:
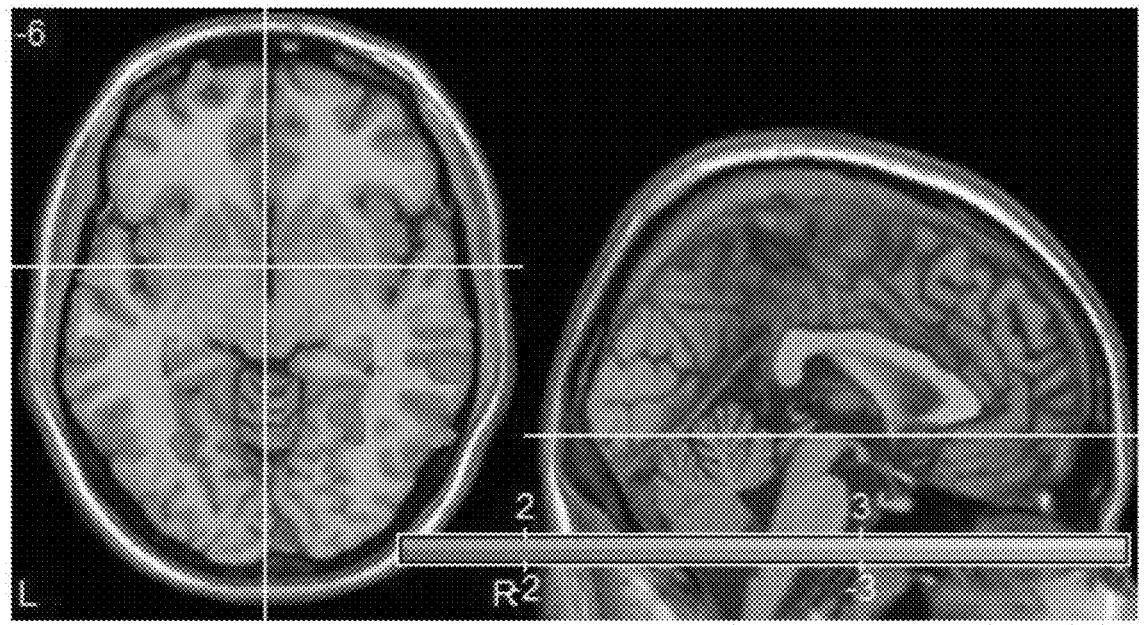
FIG. 24B illustrates patterns of neuronal activation following treatment of the same patient displayed in FIG. 24A, in which increased activation of ventral striatal regions in a task involving behavioral response to positively valenced stimuli is shown.

As illustrated in FIG. 24A, following treatment, one patient displayed decreased (blue) limbic and increased (orange) medial prefrontal activation in the context of a task involving behavioral inhibition in the setting of negative emotion, and as illustrated in FIG. 24B, following treatment this same patient displayed increased (orange) activation of ventral striatal regions in a task involving behavioral response to positively valenced stimuli.

Figure 25A:
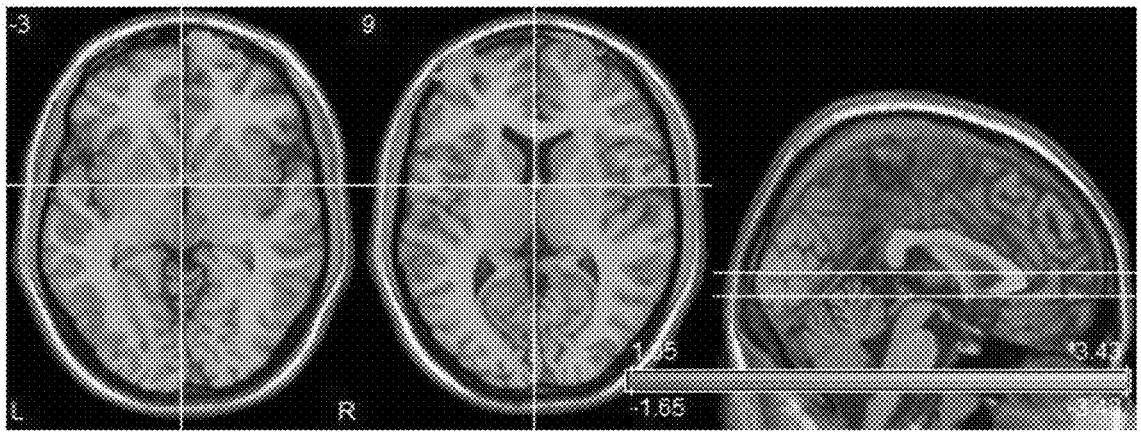
FIG. 25A illustrates patterns of neuronal activation following treatment of a patient with BOD, in which increased activation in prefrontal regions associated with inhibitory control is shown.
Figure 25B:
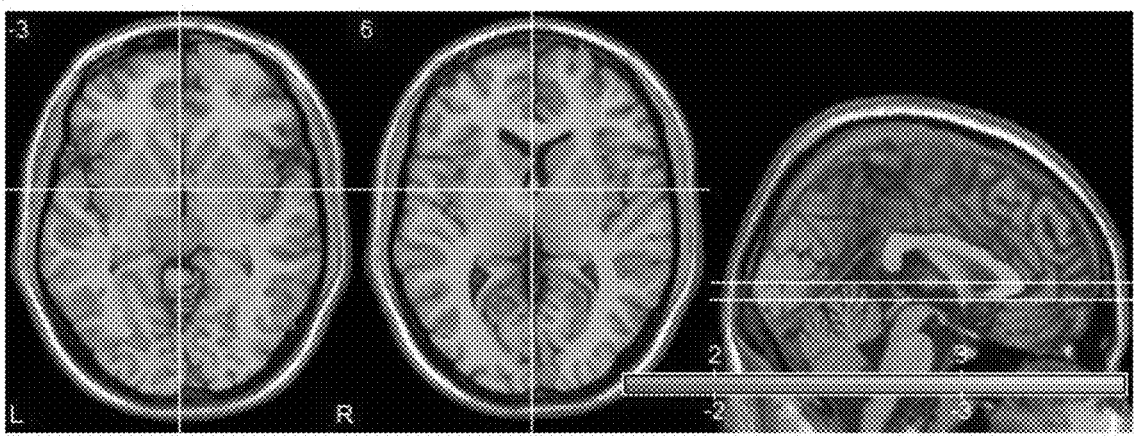
FIG. 25B illustrates patterns of neuronal activation following treatment of a patient with BOD, in which increased activation in prefrontal regions associated with inhibitory control is shown.
Figure 25C:
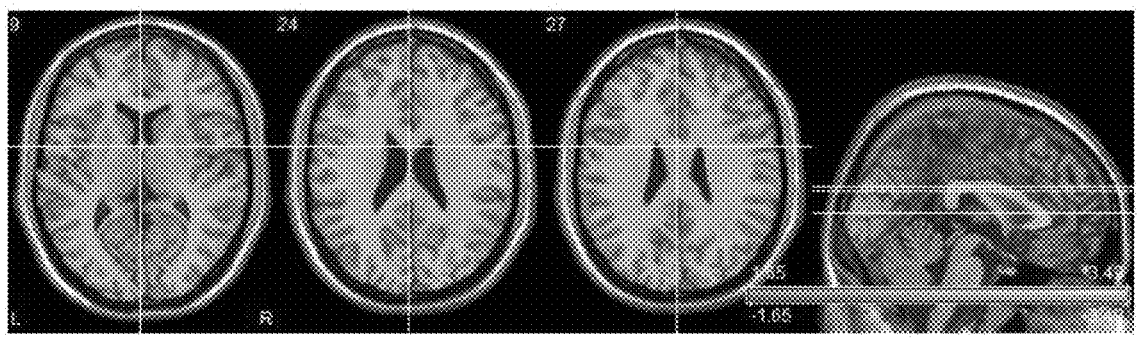
FIG. 25C illustrates patterns of neuronal activation following treatment of a patient with BOD, in which increased activation in prefrontal regions associated with self-monitoring in the context of a task involving behavioral inhibition in the setting of negative emotion is shown.
Figure 25D:
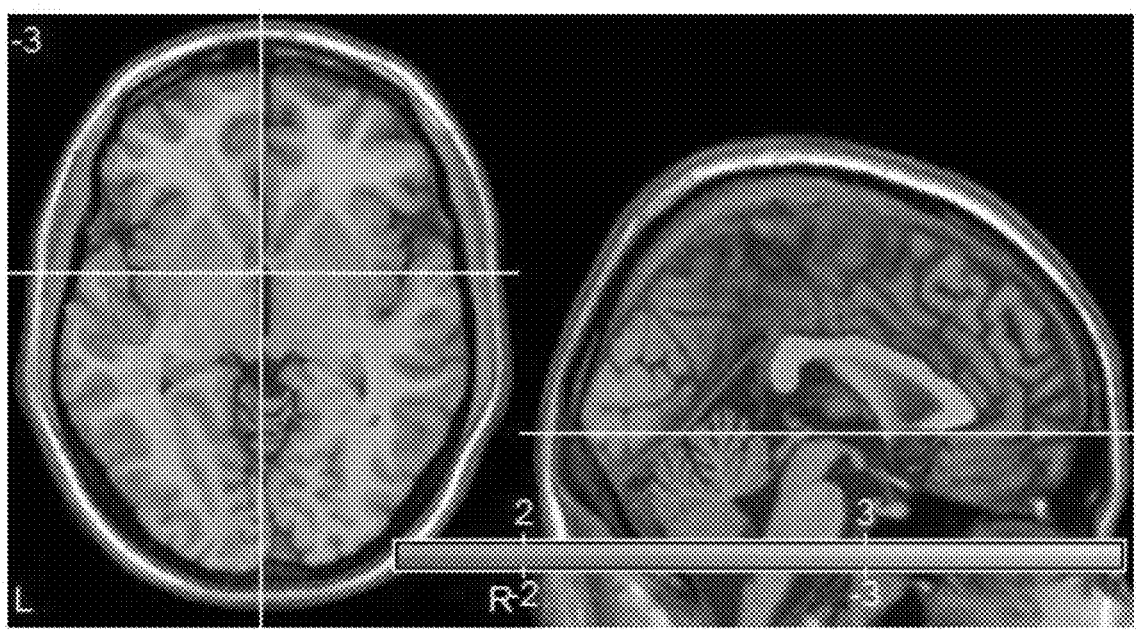
FIG. 25D illustrates patterns of neuronal activation following treatment of a patient with BOD, in which increased activation of ventral striatal regions in tasks involving positive stimuli is shown.

As illustrated in FIGS. 25A-25D, following treatment, another patient displayed increased (orange) activation in prefrontal regions associated with inhibitory control (FIGS. 25A and 25B) and self-monitoring (FIG. 25C) in the context of a task involving behavioral inhibition in the setting of negative emotion and increased (orange) activation of ventral striatal regions in tasks involving positive stimuli (FIG. 25D).

The example described above thus illustrates that patterns of neuronal activity can be used as a biomarker for aiding in the monitoring of treatment in patients with BPD. Using the methods described above, these patterns of neuronal activity can be implemented in a multivariate classifier to monitor and characterize neural signatures associated with treatment response in BPD. To this end, the methods described here can be utilized to monitor the response for particular treatments for BPD. In some embodiments, the multivariate classifier can be implemented to provide a quantitative measure, or to otherwise characterize, the efficacy of a particular treatment regimen.

Example 7: Biomarker for Evaluating Treatment Response in Schizophrenia

In this example, subjects included 24 adults ages 18-65 with the primary DSM-IV Schizophrenia and Schizoaffective disorder and drug-refractory persecutory delusions. Participants were randomly assigned to Paranoia-Focused Cognitive Behavioral Therapy ("PFCBT") or standard care. PFCBT lasted 15 weeks and included one group and one individual session weekly. The efficacy was evaluated using standardized measures at baseline, post-treatment, and at 6-months follow-up.

The Persecution Severity score on the PANSS was the primary outcome measure. Anticipatory Threat and Emotional Memory/Linguistic Threat fMRI paradigms were used to monitor brain circuitry changes associated with PFCBT (n=8).

Participants treated with PFCBT had significantly greater reduction in severity of paranoia, which they maintained at 6-months follow-up. PFCBT also resulted in significant changes in cognitive biases, and increases in insight. Responsiveness to PFCBT was associated with increased activation in Ventromedial Prefrontal Cortex, Anterior Cingulate Cortex, Dorsolateral Prefrontal Cortex, and decreased mesotemporolimbic activation.

Figure 26:
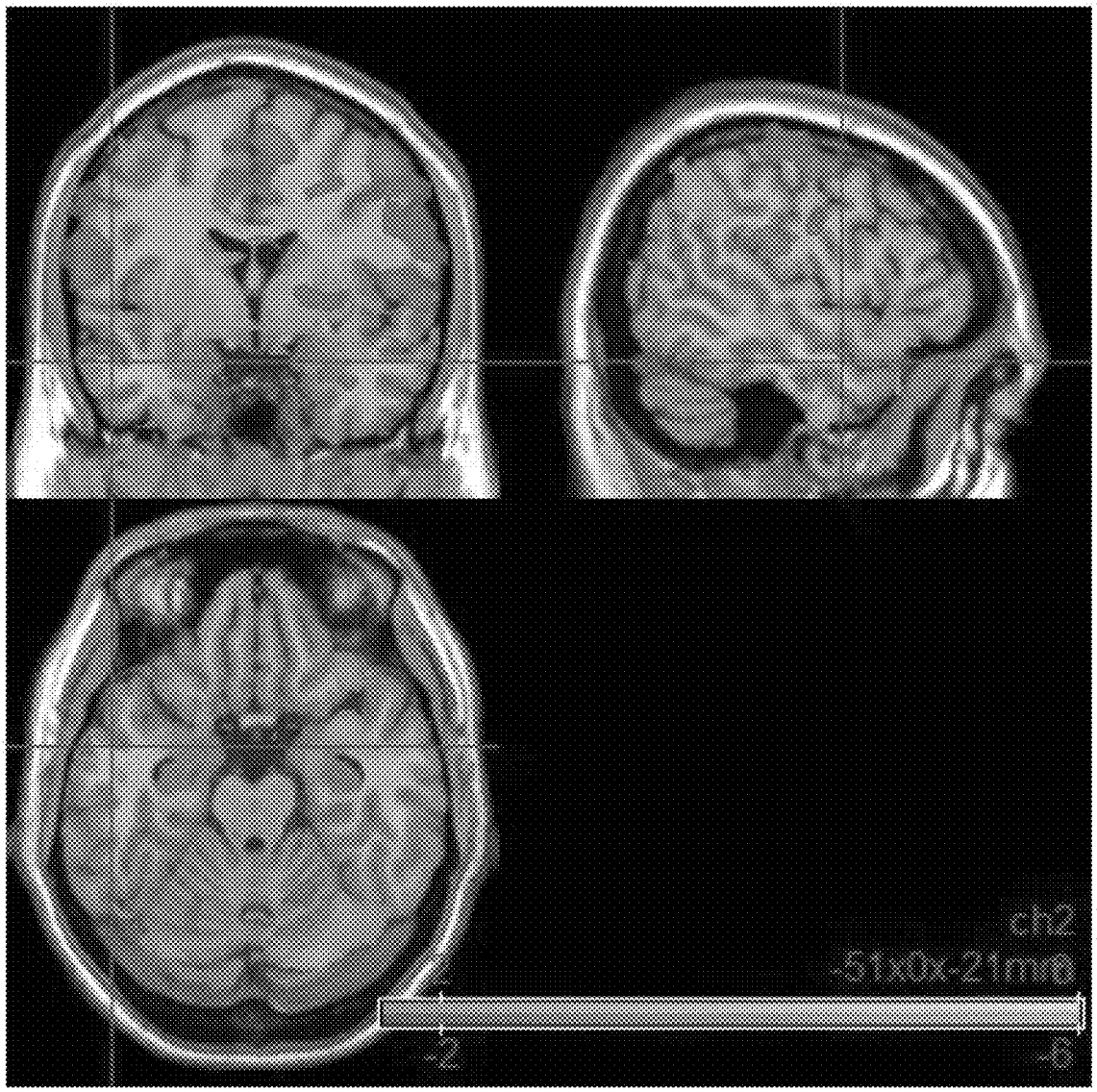
FIG. 26 illustrates correlation of the Beck BCIS Self-Certainty score with increased activations in amygdala, left frontal temporal areas, and decreased activations in dorsal lateral prefrontal regions under the condition of threat (controlled by neutral)

The Beck BCIS Self-Certainty score was also correlated with increased activations in amygdala, left frontal temporal areas, and decreased activations in dorsal lateral prefrontal regions under the condition of threat (controlled by neutral) (FIG. 26). This suggests increased emotional linguistic threat salience processing, and decreased high-order executive processing, which may have contributed to the clinical phenomenology.

The example described above thus illustrates that patterns of neuronal activity can be used as a biomarker for aiding in the monitoring of treatment in patients with schizophrenia. Using the methods described above, these patterns of neuronal activity can be implemented in a multivariate classifier to monitor and characterize neural signatures associated with treatment response in schizophrenia. To this end, the methods described here can be utilized to monitor the response for particular treatments for schizophrenia. In some embodiments, the multivariate classifier can be implemented to provide a quantitative measure, or to otherwise characterize, the efficacy of a particular treatment regimen.

Example 8: Biomarker for Evaluating Treatment Response in Schizophrenia

Figure 27:
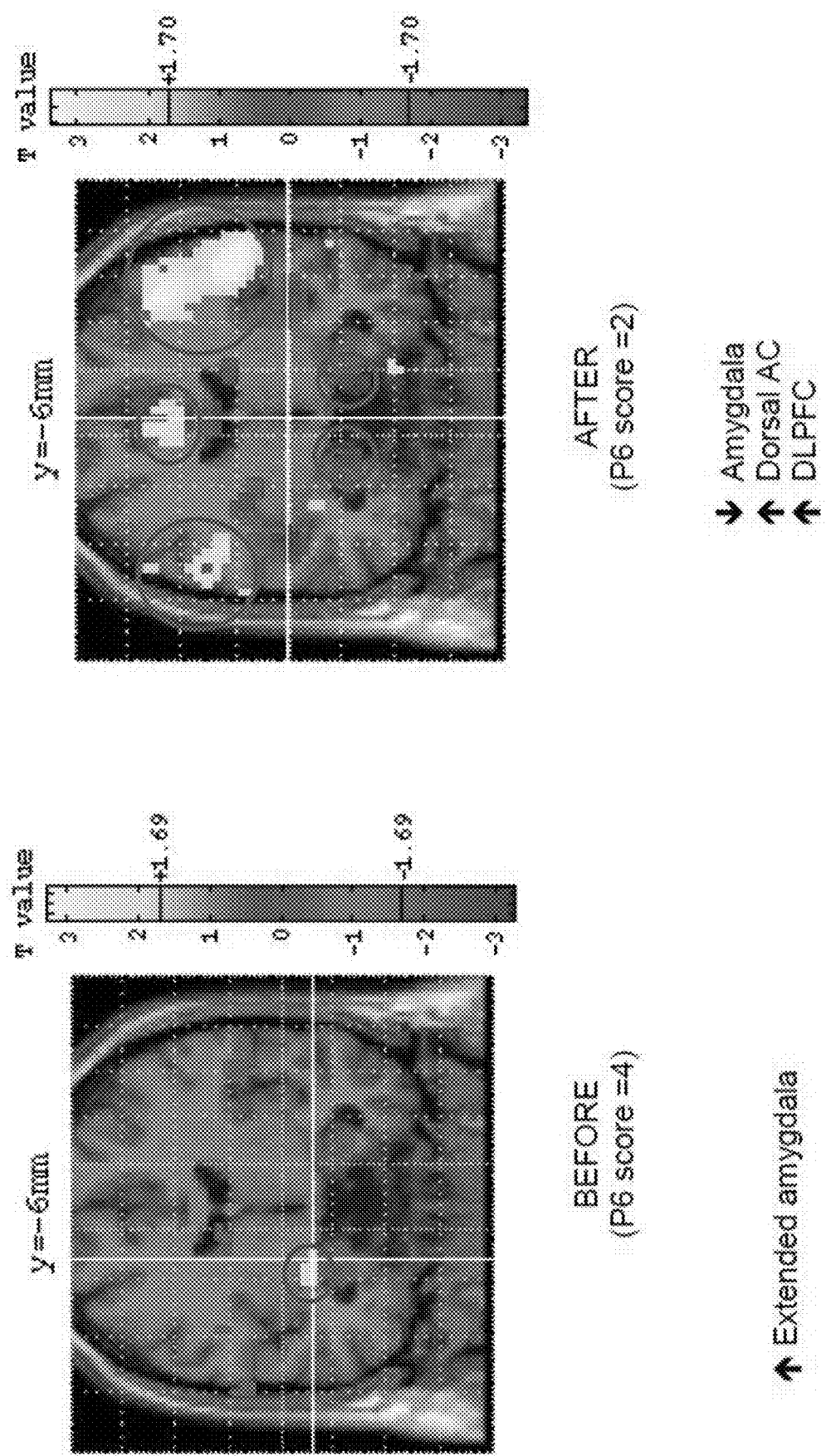
FIG. 27 illustrates decreased amygdalar reactivity with increased engagement of anterior cingulate and dorsolateral prefrontal cortices associated with treatment response (reduction in paranoid delusions as measured by the Positive and Negative Syndrome Scale (PANSS))

FIG. 27 illustrates results from another patient with schizophrenia scanned before and after cognitive behavioral therapy (CBT) with a threat/safety paradigm. The activation maps demonstrate decreased amygdalar reactivity with increased engagement of anterior cingulate and dorsolateral prefrontal cortices associated with treatment response (reduction in paranoid delusions as measured by the Positive and Negative Syndrome Scale (PANSS)).

This example further illustrates that patterns of neuronal activity can be used as a biomarker for aiding in the monitoring of treatment in patients with schizophrenia. Using the methods described above, these patterns of neuronal activity can be implemented in a multivariate classifier to monitor and characterize neural signatures associated with treatment response in schizophrenia. To this end, the methods described here can be utilized to monitor the response for particular treatments for schizophrenia. In some embodiments, the multivariate classifier can be implemented to provide a quantitative measure, or to otherwise characterize, the efficacy of a particular treatment regimen.

Example 9: Biomarker for Diagnosing Major Depression

Figure 28:
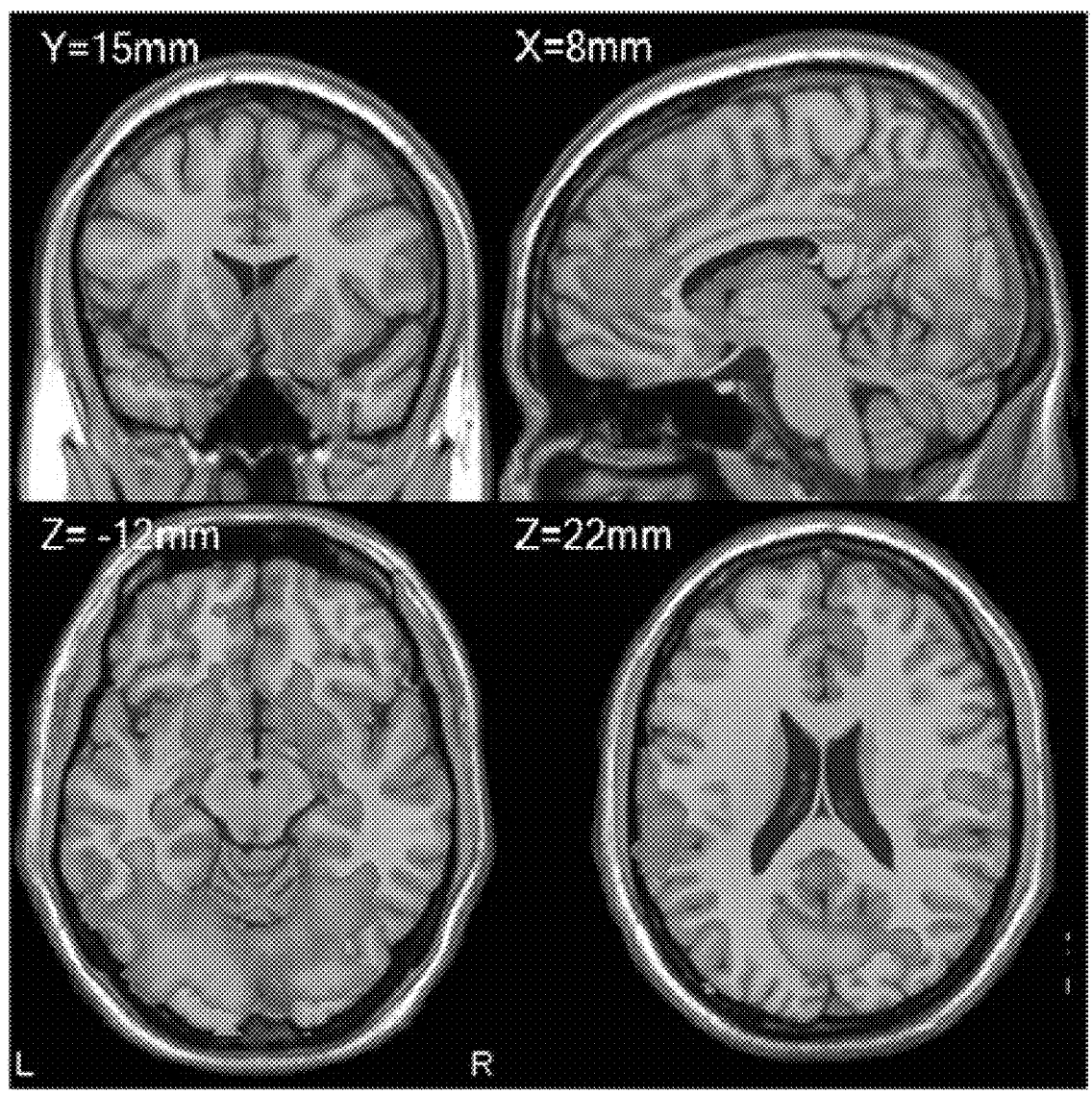
FIG. 28 illustrates patterns of brain activity during a positive emotional condition, which can be used to distinguish patients with major depression from healthy controls, with a data-driven, multivariate (e.g., PCA-based) analysis.

FIG. 28 illustrates results from a patient with major depression, which highlight emotional brain circuits and their interaction with cognitive circuits, perceptual circuits, and/or behavioral circuits. In particular, the activation maps illustrated in FIG. 28 depict patterns of brain activity during a positive emotional condition, which can be used to distinguish patients with major depression from healthy controls, with a data-driven, multivariate (e.g., PCA-based) analysis.

This example illustrates that patterns of neuronal activity can be used as a biomarker for aiding in the diagnosis of major depression. Using the methods described above, these patterns of neuronal activity can be implemented in a multivariate classifier to identify individuals as belonging to a population consistent with the neural signatures associated with major depression. To this end, the methods described here can be utilized to provide diagnostic information about whether a patient is likely to have major depression.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer-implemented method for generating a biomarker associated with a neuropsychiatric, neurodevelopmental, neurobehavioral, or other neurological disorder, the steps of the method comprising:
   (a) providing to a computer system, functional imaging data acquired from a subject's brain;
   (b) providing to the computer system, clinical data associated with the subject; and
   (c) generating with the computer system, a biomarker associated with the neuropsychiatric, neurodevelopmental, neurobehavioral, or other neurological disorder by computing a correlation between the functional imaging data and the clinical data using a multivariate classifier;
   (d) forming a matrix that includes matrix data that corresponds to regions in the subject's brain and the functional imaging data and the clinical data; and
   wherein the computer system is used to perform at least one of dimensionality reduction or feature extraction on the matrix before inputting the matrix to the multivariate classifier.

2. The method as recited in claim 1, wherein step (d) includes forming the matrix having rows that correspond to the regions in the subject's brain and having columns that correspond to the functional imaging data and the clinical data, and wherein computing the correlation between the functional imaging data and the clinical data includes inputting the matrix to the multivariate classifier.

3. The method as recited in claim 1, wherein the functional imaging data includes at least one of functional magnetic resonance images acquired from the subject while the subject was performing a functional task, or functional magnetic resonance images acquired from the subject while the subject was in a resting state.

4. The method as recited in claim 3, wherein step (a) includes generating from the functional magnetic resonance images and with the computer system, activation maps that depict neuronal activation patterns associated with at least one of the functional task or the resting state.

5. The method as recited in claim 4, wherein the activation maps are generated with the computer system by using a multi-level mixed-effects statistical model.

6. The method as recited in claim 5, wherein the multi-level mixed-effects statistical model includes a nested random-effects structure.

7. The method as recited in claim 6, wherein the multi-level mixed-effects statistical model further includes an intra-subject power variance function and an autoregressive correlation structure.

8. The method as recited in claim 1, further comprising providing to the computer system additional data associated with system-level biological measures of the subject, and wherein step (c) includes generating the biomarker by computing a correlation between the functional imaging data, the clinical data, and the additional data using the multivariate classifier.

9. The method as recited in claim 8, wherein the additional data includes at least one of other imaging data, physiological data, genetic data, or epigenetic data.

10. The method as recited in claim 1, wherein step (c) includes generating a classifier map using the computer system to map the correlation to a multidimensional parametric space having dimensions associated with the functional imaging data and the clinical data.

11. The method as recited in claim 10, wherein the biomarker includes a quantitative metric computed by the computer system from the classifier map, and wherein step (c) includes generating a report based on the quantitative metric.

12. The method as recited in claim 11, wherein the quantitative metric is a center-of-mass of correlated data associated with a particular classified group.

13. The method as recited in claim 11, wherein the quantitative metric is a distance of the subject's correlated data from a center-of-mass of correlated data associated with a particular classified group.

14. The method as recited in claim 1, wherein the biomarker indicates a degree of efficacy of a particular treatment, and steps (a)-(c) are repeated at a different time to evaluate the degree of efficacy of the particular treatment.

15. A computer-implemented method for generating a biomarker that indicates a target for treating a neuropsychiatric, neurodevelopmental, neurobehavioral, or other neurological disorder, the steps of the method comprising:
(a) providing to a computer system, functional imaging data acquired from a subject's brain;
(b) providing to the computer system, clinical data associated with the subject;
(c) providing to the computer system, additional data associated with system-level biological measures of the subject;
(d) forming a matrix using the computer system that includes matrix data that corresponds to regions in the subject's brain and the functional imaging data and the clinical data; and wherein the computer system is used to perform at least one of dimensionality reduction or feature extraction on the matrix; and
(e) generating with the computer system, a biomarker that indicates a target for treating a neuropsychiatric, neurodevelopmental, neurobehavioral, or other neurological disorder by computing a correlation between the functional imaging data, the clinical data, and the additional data using a multivariate classifier.

16. The method as recited in claim 15, wherein step (d) includes generating the biomarker by mapping with the computer system, the correlation to a multidimensional parametric space, in which data points mapped to a similar region of the multidimensional parametric space correspond to similar neural signatures and symptoms associated with the neuropsychiatric, neurodevelopmental, neurobehavioral, or other neurological disorder.

17. The method as recited in claim 16, wherein the multidimensional parametric space includes dimensions corresponding to the functional imaging data, the clinical data, and the additional data.

18. The method as recited in claim 16, wherein the biomarker indicates a functional target for treatment, in which the functional target represents symptoms correlated with the neuropsychiatric, neurodevelopmental, neurobehavioral, or other neurological disorder.

19. The method as recited in claim 18, wherein the functional target further represents patterns of neuronal activation correlated with the symptoms and the neuropsychiatric, neurodevelopmental, neurobehavioral, or other neurological disorder.

20. The method as recited in claim 16, wherein the biomarker indicates an anatomical target for treatment, in which the anatomical target represents brain regions associated with symptoms correlated with the neuropsychiatric, neurodevelopmental, neurobehavioral, or other neurological disorder.

* * * * *